United States Patent
Aono et al.

(10) Patent No.: US 6,420,375 B1
(45) Date of Patent: Jul. 16, 2002

(54) FUSED RING COMPOUNDS, PROCESS FOR PRODUCING THE SAME AND USE THEREOF

(75) Inventors: Tetsuya Aono, Nagaokakyo; Fumio Itoh, Toyonaka; Tomohiro Kaku, Nishinomiya; Masuo Yamaoka, Kobe, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/367,896

(22) PCT Filed: Feb. 19, 1998

(86) PCT No.: PCT/JP98/00688

§ 371 (c)(1),
(2), (4) Date: Aug. 18, 1999

(87) PCT Pub. No.: WO98/37070

PCT Pub. Date: Aug. 27, 1998

(30) Foreign Application Priority Data

Feb. 21, 1997 (JP) .............................................. 9-037927

(51) Int. Cl.⁷ .................... C07D 233/56; C07D 401/06; A61K 31/44; A61D 5/26

(52) U.S. Cl. ...................... 514/277; 514/307; 514/314; 514/336; 514/359; 514/383; 514/396; 514/397; 546/148; 546/176; 546/280.1; 546/282.7; 546/350; 548/255; 548/262.2; 548/267.8; 548/311.4; 548/346.1; 548/343.1

(58) Field of Search ........................... 548/311.4, 343.1, 548/346.1, 255, 262.2, 267.8, 347.1; 514/314, 337, 397, 277, 367, 336, 359, 383, 396, 392; 546/176, 148, 280.1, 282.7, 350

(56) References Cited

U.S. PATENT DOCUMENTS

| | | | | |
|---|---|---|---|---|
| 3,642,781 A | * | 2/1972 | Strandtmann et al. | 260/240 |
| 4,237,133 A | * | 12/1980 | Althuis et al. | 424/248.52 |
| 4,654,352 A | * | 3/1987 | Ray | 514/324 |
| 4,948,796 A | * | 8/1990 | Hiraiwa et al. | 514/254 |
| 5,124,473 A | * | 6/1992 | Shroot et al. | 560/56 |
| 5,273,977 A | * | 12/1993 | Glase et al. | 514/277 |
| 5,543,422 A | * | 8/1996 | Coutts et al. | 514/319 |
| 6,005,000 A | * | 12/1999 | Hopper et al. | 514/473 |

FOREIGN PATENT DOCUMENTS

| | | |
|---|---|---|
| JP | 64-85975 | 3/1989 |
| JP | 1-246272 | 10/1989 |
| JP | 6-239856 | 8/1994 |
| JP | 6-293640 | 10/1994 |
| JP | 7-173120 | 7/1995 |
| WO | WO 93/10113 | 5/1993 |
| WO | WO 95/09157 | 4/1995 |
| WO | WO 96/21644 | 7/1996 |
| WO | WO 96/23773 | 8/1996 |
| WO | WO 97/17321 | 5/1997 |
| WO | WO 97/20815 | 6/1997 |
| WO | WO 97/29079 | 8/1997 |
| WO | WO 97/33856 | 9/1997 |
| WO | WO 97/36864 | 10/1997 |
| WO | WO 98/01443 | 1/1998 |

OTHER PUBLICATIONS

Tarshits et al, (Khim. Geterotsikl. Soedin., 11, 1472–1475), 1988.*
Ravina et al, (Chim. Ther., 8(2), 185–187), 1973.*
Areshka et al, (Chim. Ther., 5(6), 331–334), 1966.*
Arcadi et al, (Tetrahedron Lett., 52(11), 3997–4012), 1996.*
Wilkens et al, (Tetrahedron., 43(14), 3237–3246), 1987.*
Dax et al, (Bioorg. Med. Chem. Lett., 6(7), 797–802). 1996.*
Boyfield et al, (J. Med. Chem., 39(10), 1946–1948), 1988.*
Blechert et al, (Tetrahedron Lett., 33(44), 6621–6624), 1992.*
Porszasz et al (Acta Phys Chem., 10, 41–56), 1964.*
Glase et al (J. Med. Chem., 39(16), 3179–3187), 1996.*
Bardamova et al (Khim. Geterotsikl. Soedin., 11, 1457–1460), 1972.*
G. Cristalli et al., "Platelet Aggregation Inhibitory Activity of . . . " *Nucleosides & Nucleotides*, 14(3–5), 449–453 (1995).
R. Li et al., "In Vitro Antimalarial Activity of Chalcones . . . " *J. Med. Chem.* 1995, 38, 5031–5037.
R. Alaimo, "Anthelmintic 1–Cinnamamido–2, 4–imidazolidinediones" *J. Med. Chem.* 1976, 19(2), 349–350.
J. Hoffman et al, "Synthesis and Evaluation of 2–Pyridinone Derivatives . . . " *J. Med. Chem.*, 1993, 36, 953–966.
G. Martinez et al, "3,4–Dihydroquinolin–2(1H)–ones as . . . " *J. Med. Chem.* 1992, 35, 620–628.

* cited by examiner

*Primary Examiner*—Richard L. Raymond
*Assistant Examiner*—Thomas McKenzie
(74) *Attorney, Agent, or Firm*—Mark Chao; Elaine M. Ramesh

(57) ABSTRACT

To provide a novel compound of the formula:

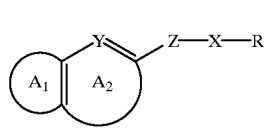

(I)

[wherein $A_1$ ix a 5 or 6-membered ring which may be substituted by a group not containing a cyclic group, $A_2$ is an aromatic ring which may be substituted, X is a divalent group, Y is a nitrogen atom or a methine group, Z is an ethenylene which may be substituted or ethynylene, R is a heterocyclic group which may be substituted, provided that 3,4-dihydro-6-[3-(1H-imidazol-1-yl)-1-propenyl]-2(1H)-quinolone and 2-[3-[5-ethyl-6-methyl-2-(benzyloxy)-3-pyridyl]-1-propenyl]benzoxazole are excluded.], or a salt thereof which has steroid $C_{17,20}$-lyase inhibitory activity, and is useful for preventing and treating mammals suffering from, for example, primary cancer of malignant tumor, its metastasis and recurrence thereof.

19 Claims, No Drawings

FUSED RING COMPOUNDS, PROCESS FOR PRODUCING THE SAME AND USE THEREOF

This application is the National Stage of International Application No. PCT/JP98/00688, filed on Feb. 19, 1998.

TECHNICAL FIELD

The present invention relates to a medicine, especially to novel fused ring compound having steroid $C_{17,20}$-lyase inhibitory activity, or its production and pharmaceutical compositions containing the same.

BACKGROUND ART

Steroid $C_{17,20}$-lyase converts 17-hydroxypregnenolone and 17-hydroxyprogesterone derived from cholesterol to androgen. Therefore, a medicine having steroid $C_{17,20}$-lyase inhibitory activity suppresses the formation of androgen and estrogen which is produced from androgen, and is useful for the preventing and treating diseases whose exacerbation factor is androgen or estrogen. As the diseases whose exacerbation factor is androgen or estrogen, there may be mentioned, for example, prostate cancer, prostatic hypertrophy, virilism, hirsutism, male pattern alopecia, precocious puberty, breast cancer, uterine cancer, mastopathy, uterus myoma, endometriosis, etc.

It has been already known that some steroid type compounds and some non-steroid type compounds inhibit steroid $C_{17,20}$-lyase. The steroid type compounds are disclosed in, for example, WO 92/15404, WO 93/20097, EP-A 288053, EP-A 413270, etc. As non-steroid type compounds, for example, (1H-imidazol-1-yl)methyl-substituted benzimidazole derivatives are shown in Japanese Published Unexamined Patent Application No.85975/1989, carbazole derivatives are shown in WO94/27989 and WO96/14090, azole derivatives are shown in WO95/09157, and 1H-benzimidazole derivatives are shown in U.S. Pat. No. 5,491,161.

Heretofore, steroid $C_{17,20}$-lyase inhibitors which can actually be used as medicine have not been known. Thus, the early development of steroid $C_{17,20}$-lyase inhibitors which are useful as medicine has been highly anticipated.

DISCLOSURE OF INVENTION

The present inventors have done extensive studies so as to find superior androgen synthetase inhibitors, especially steroid a $C_{17,20}$-lyase inhibitors, and found that a compound having the formula (I)

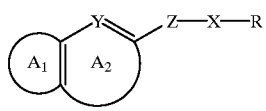

has superior steroid $C_{17,20}$-lyase inhibiting activity because of its specific structure and that the compound has less toxicity and has good properties as medicine. The present invention has been accomplished by these findings.

The present invention relates to:
(1) A compound of the formula:

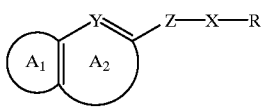

[wherein $A_1$ is a 5 or 6-membered ring which may be substituted by a group not containing a cyclic group, $A_2$ is an aromatic ring which may be substituted, X is a divalent group, Y is a nitrogen atom or a methine group, Z is an ethenylene which may be substituted or ethynylene, R is a heterocyclic group which may be substituted, provided that 3,4-dihydro-6-[3-(1H-imidazol-1-yl)-1-propenyl]-2(1H)-quinolone and 2-[3-[5-ethyl-6-methyl-2-(benzyloxy)-3-pyridyl]-1-propenyl]benzoxazole are excluded.], or a salt thereof, (2) A compound as shown in the above item (1), wherein R is a 5 or 6-membered nitrogen-containing heterocyclic group which may be substituted, (3) A compound as shown in the above item (1), wherein R is an imidazolyl, a triazolyl or a pyridyl which may be substituted, (4) A compound as shown in the above item (1), wherein R is an imidazolyl which may be substituted, (5) A compound as shown in the above item (1), wherein the ring:

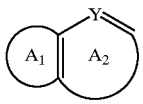

is naphthalene or tetraline, (6) A compound as shown in the above item (1), wherein the ring:

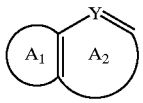

is benzothiophene or benzofuran, (7) A compound as shown in the above item (1), wherein the ring:

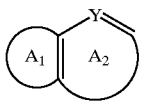

is benzothiophene, (8) A compound as shown in the above item (1), wherein Z is an ethenylene which may be substituted, (9) A compound as shown in the above item (1), wherein Z is an ethenylene which may be substituted by methyl or fluorine,

(10) A compound as shown in the above item (1), wherein Z is unsubstituted ethenylene,

(11) A compound as shown in the above item (1), wherein X is a divalent hydrocarbon group which may be substituted.

(12) A compound as shown in the above item (1), wherein X is a methylene which may be substituted,

(13) A compound as shown in the above item (1), wherein X is unsubstituted methylene,

(14) A compound as shown in the above item (1), which is 1-[(E)-3-(2-naphthyl)-2-propene-1-yl]-1H-imidazole or a salt thereof,

(15) A compound as shown in the above item (1), which is 1-[(E)-3-(2-naphthyl)-2-butene-1-yl]-1H-imidazole or a salt thereof,

(16) A compound as shown in the above item (1), which is 1-[(E)-3-(5-fluoro-3-methylbenzo[b]thiophene-2-yl)-2-propene-1-yl]-1H-imidazole or a salt thereof,

(17) A compound as shown in the above item (1), which is 4-[(E)-3-(5-fluoro-3-methylbenzo[b]thiophene-2-yl)-2-propene-1-yl]-1H-imidazole or a salt thereof,

(18) A compound as shown in the above item (1), which is 4-[-(E)-3-(5-methoxy-3-methylbenzo[b]thiophene-2-yl)-2-propene-1-yl]-1H-imidazole or a salt thereof,

(19) A pharmaceutical composition containing a compound as shown in the above item (1),

(20) A steroid $C_{17,20}$-lyase inhibitory composition containing a compound of the formula:

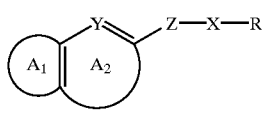

(I')

[wherein $A_1$ is a 5 or 6-membered ring which may be substituted by a group not containing a cyclic group, $A_2$ is an aromatic ring which may be substituted, X is a divalent group, Y is a nitrogen atom or a methine group, Z is an ethenylene which may be substituted or ethynylene, R is a heterocyclic group which may be substituted.]or a salt thereof,

(21) An antitumor composition which contains a compound of the formula (I') or salt thereof,

(22) An antitumor composition containing a compound of the formula (I') or salt thereof as shown in the above item (21), wherein the antitumor composition is treating or preventing agent for breast cancer or prostate cancer,

(23) A method for treating mammal suffering from diseases whose exacerbation factor is androgen or estrogen, which comprises administering an effective amount of a compound of the formula (I) or a salt thereof;

(24) A method as shown in the above item (23) wherein the diseases whose exacerbation factor is androgen or estrogen is prostate cancer, prostatic hypertrophy, virilism, hirsutism, male pattern alopecia, precocious puberty, breast cancer, uterine cancer, mastopathy, uterus myoma, endometriosis;

(25) Use of a compound of the formula (I') or salt thereof for the production of an antitumor composition for treating diseases whose exacerbation factor is androgen or estrogen;

(26) Use as shown in the above item (25) wherein the diseases whose exacerbation factor is androgen or estrogen is prostate cancer, prostatic hypertrophy, virilism, hirsutism, male pattern alopecia, precocious puberty, breast cancer, uterine cancer, mastopathy, uterus myoma, endometriosis; and

(27) A process for producing a compound of the above item (1), which comprises reacting a compound of the formula:

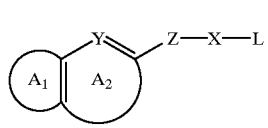

(II)

[wherein L is a leaving group, and each of the other symbols has the meanings as defined in the above item (1).] or a salt thereof with a compound of the formula:

M—R (III)

[wherein M is a hydrogen atom or a metal atom, and R has the meanings as defined in the above item (1).] or a salt thereof.

BEST MODE FOR CARRYING OUT THE INVENTION

Examples of the "5 or 6-membered ring" in the "5 or 6-membered ring which may be substituted by a group not containing a cyclic group" represented by $A_1$ ring in the formula (I) include, for example, a 5 or 6-membered cyclic hydrocarbon, a 5 or 6-membered aromatic heterocyclic ring and a 5 or 6-membered non-aromatic heterocyclic ring, etc.

Examples of the 5 or 6-membered cyclic hydrocarbons include, for example, a $C_{5-6}$cyclo alkane (cyclopentane, cyclohexane), a $C_{5-6}$cycloalkene (cyclopentene, cyclohexene) and benzene, etc., The examples of the 5 or 6-membered aromatic heterocyclic groups include, for example, furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine (1,3,5-triazine, 1,2,4-triazine), etc.

The examples of the 5 or 6-membered non-aromatic heterocyclic groups include, pyrrolidine, tetrahydrofuran, thiolan, piperidine, tetrahydropyran, morpholine, thiomorpholine, piperazine, homopiperidine, pyrroline, imidazolidine, etc Examples of the "aromatic ring" in the "aromatic ring which may be substituted" represented by $A_2$ in the formula (I) include, for example, phenyl, a heterocyclic ring such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine (1,3,5-triazine, 1,2,4-triazine), etc.

The fused ring compound represented by the formula:

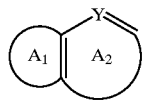

in the formula (I) includes, both of a cyclic hydrocarbon and a heterocyclic ring. When one of the rings ($A_2$ ring) is an aromatic ring, the other ($A_1$ ring) may be an aromatic ring or an aliphatic ring. Examples of the fused ring compounds include a cyclic hydrocarbon (e.g., naphthalene), a heterocyclic compound containing a nitrogen atom (indolizine, isoindole, indole, isoquinoline, quinoline, indazole, phthalazine, naphthyridine, quinoxaline, quinazoline, cinnoline, piridopyridine, pteridine, purine, etc.), an oxygen-containing heterocyclic ring (isochroman, chroman, benzofuran, cyclopentapyran, etc.), a sulfur-containing heterocyclic ring (benzothiophene, etc.), a heterocyclic ring containing two or more hetero atoms which are different from each other (benzothiazole, benzoxazole, thiazolopyridine, etc.), and compounds whose $A_1$ ring is reduced (e.g., tetraline, 1,2-dihydronaphthalene, 3,4-dihydronaphthalene, indane, indene, etc.), etc. Preferable examples of the fused rings include, for example, naphthalene, tetraline, benzothiophene, benzofuran, etc.

When $A_1$ ring has a substituent or substituents, the substituent is neither a ring nor a group containing a ring. Examples of the substituents include (1) a lower alkyl group which may be substituted, (2) a lower alkoxy group which may be substituted, (3) a carboxyl group which may be esterified, (4) a carbamoyl group which may be substituted or a thiocarbamoyl group which may be substituted, (5) an amino group which may be substituted, (6) a hydroxyl group which may be substituted, (7) a thiol (mercapto) group which may be substituted, (8) an acyl group, (9) a halogen atom (e.g., fluorine, chlorine, bromine, etc.), (10) a nitro group, (11) a cyano group, (12) an oxo group, etc. One to three of these substituents may substitute at any position.

Examples of the "lower alkyl group" in the "lower alkyl group which may be substituted" (1) include, for example, a $C_{1-6}$alkyl group such as methyl, ethyl, propyl, isopropyl, butyl, isobutyl, sec.-butyl, tert.-butyl, pentyl, isopentyl, neopentyl, hexyl, isohexyl, etc.

Examples of the "lower alkoxy group" in the "lower alkoxy group which may be substituted" (2) include, for example, a $C_{1-6}$alkoxy group such as methoxy, ethoxy, propoxy, isopropoxy, butoxy, isobutoxy, sec.-butoxy, tert.-butoxy, pentoxy, isopentoxy, neopentoxy, hexyloxy, isohexyloxy, etc.

The lower alkyl group (1) and the lower alkoxy group (2) may have one to three substituents at any substitutable position. Examples of the substituents include, for example, a halogen (e.g., fluorine, chlorine, bromine, etc.), a lower $(C_{1-3})$alkoxy (e.g., methoxy, ethoxy, propoxy, etc.), a hydroxyl group, an amino group which may be substituted by a lower $(C_{1-3})$alkyl (e.g., amino, methylamino, dimethylamino, diethylamino), etc.

Examples of the "carboxyl which may be esterified" (3) include a carboxyl group, a (lower $(C_{1-6})$alkoxy)carbonyl (e.g., methoxycarbonyl, ethoxycarbonyl, propoxycarbonyl, isopropoxycarbonyl, butoxycarbonyl, isobutoxycarbonyl, tert.-butoxycarbonyl, sec.-butoxycarbonyl, pentyloxycarbonyl, isopentyloxycarbonyl, neopentyloxycarbonyl, tert.-pentyloxycarbonyl, hexyloxycarbonyl, etc.), etc. Among them, carboxyl, methoxycarbonyl, ethoxycarbonyl, etc., are preferable.

Examples of the substituent of the "carbamoyl group which may be substituted" or "thiocarbamoyl group which may be substituted" (4) and the "amino group which may be substituted" (5) include, for example, a $C_{1-6}$alkyl which may be substituted etc. Examples of the "$C_{1-6}$alkyl" in the "$C_{1-6}$alkyl which may be substituted" include, for example, methyl, ethyl, propyl, isopropyl, butyl, isobutyl, sec.-butyl, tert.-butyl, pentyl, isopentyl, neopentyl, hexyl, isohexyl, etc. These substituents may be the same or different, and one or two of these substituents maybe substituted. Examples of the substituents in the "$C_{1-6}$alkyl group which may be substituted" include, a halogen (e.g., fluorine, chlorine, bromine, etc.), an alkoxy group which may be substituted by 1 to 3 halogen atoms (e.g., a $C_{1-4}$alkoxy group such as methoxy, ethoxy, propoxy, etc., a $C_{1-4}$alkoxy group substituted by a halogen or halogens such as trifluoromethoxy, 2,2,2-trifluoroethoxy, 2,2,3,3, 3-pentafluoropropoxy, etc.), an alkyl group which may be substituted by 1 to 3 halogen atoms (e.g., a $C_{1-4}$alkyl such as methyl, ethyl, propyl, etc.), nitro, etc. One to five of these substituents may be substituted.

Example of the substituents in the "hydroxyl group which may be substituted" (6) and the "thiol group which may be substituted" (7) include, for example, a $C_{1-6}$alkyl which may be substituted, etc. Examples of the "$C_{1-6}$alkyl" in the "$C_{1-6}$alkyl which may be substituted" include, for example, methyl, ethyl, propyl, isopropyl, butyl, isobutyl, sec.-butyl, tert.-butyl, pentyl, isopentyl, neopentyl, hexyl, isohexyl, etc. The $C_{1-6}$alkyl group may have 1 to 5 substituents at any substitutable position. Examples of the substituents include, for example, a halogen (e.g., fluorine, chlorine, bromine, etc.), an alkoxy group which may be substituted by 1 to 3 halogen atoms (e.g., a $C_{1-4}$alkoxy such as methoxy, ethoxy, propoxy, etc., a $C_{1-4}$alkoxy which is substituted by 1 to 3 halogens such as trifluoromethoxy, 2,2,2-trifluoroethoxy, 2,2,3,3,3-pentafluoropropoxy, etc.), an alkyl group which may be substituted by 1 to 3 halogen atoms (e.g., a $C_{1-4}$alkyl such as methyl, ethyl, propyl, isopropyl, butyl, etc., a $C_{1-4}$alkyl substituted by a halogen such as trifluoromethyl, 2,2,2-trifluoroethyl, 2,2,3,3,3-pentafluoropropyl, etc.), nitro, amino, cyano, etc.

Examples of the acyl groups (8) include, for example, formyl, a carbonyl group substituted by a hydrocarbon group which may be substituted, a sulfinyl group substituted by a hydrocarbon group which may be substituted, a sulfonyl group substituted by a hydrocarbon group which may be substituted, etc. Examples of the "hydrocarbon group which may be substituted" include, for example, a $C_{1-6}$alkyl group which may be substituted, etc. That is, examples of the acyl groups include, formyl as well as a carbonyl group, a sulfinyl group and a sulfonyl group, each of which is substituted by a $C_{1-6}$alkyl (e.g., methyl, ethyl, propyl, isopropyl, butyl, isobutyl, sec-butyl, tert-butyl, pentyl, isopentyl, neopentyl, hexyl, isohexyl, etc.). The $C_{1-6}$alkyl may be substituted, at any substitutable position, by 1 to 5 substituents. Examples of the substituents include, for example, a halogen atom (e.g., fluorine, chlorine, bromine, iodine), a lower alkoxy group (e.g., a $C_{1-4}$alkoxy group such as methoxy, ethoxy, propoxy, etc.), a lower alkyl group (e.g., $C_{1-4}$alkyl group such as methyl, ethyl, propyl, etc.), etc.

When $A_2$ ring is substituted, examples of the substituents include, (1) a lower alkyl group which may be substituted, (2) a lower alkoxy group which may be substituted, (3) an aryl group which may be substituted, (4) a lower cycloalkyl group or a cycloalkenyl group which may be substituted, (5) a carboxyl group which may be esterified, (6) a carbamoyl group or a thio carbamoyl group which may be substituted, (7) an amino group which may be substituted, (8) a hydroxyl group which may be substituted, (9) a thiol (mercapto) group which may be substituted, (10) an acyl group, (11) a halogen atom (e.g., fluorine, chlorine, bromine, etc.), (12) a nitro group, (13) a cyano group, etc. The number of the substituent(s) may be 1 to 3.

Examples of the "lower alkyl" in the "lower alkyl group which may be substituted" (1) include, for example, a $C_{1-6}$alkyl group such as methyl, ethyl, propyl, isopropyl, butyl, isobutyl, sec.-butyl, tert.-butyl, pentyl, isopentyl, neopentyl, hexyl, isohexyl, etc.

Examples of the "lower alkoxy group" in the "lower alkoxy group which may be substituted" (2) include a $C_{1-6}$alkoxy group such as methoxy, ethoxy, propoxy, isopropoxy, butoxy, isobutoxy, sec.-butoxy, tert.-butoxy, pentoxy, isopentoxy, neopentoxy, hexyloxy, isohexyloxy, etc.

Each of the lower alkyl group (1) and the lower alkoxy group (2) may have 1 to 3 substituents at any substitutable position. Examples of the substituents include, for example, a halogen (e.g., fluorine, chlorine, bromine, etc.), a lower ($C_{1-3}$)alkoxy (e.g., methoxy, ethoxy, propoxy, etc.) a hydroxyl group, an amino group which may be substituted (e.g., amino, methylamino, dimethylamino, diethylamino), etc.

Examples of the "aryl group" in the "aryl group which may be substituted" (3) include a $C_{6-10}$ aryl group such as phenyl, naphthyl, etc. Among them, phenyl is preferable.

Examples of the "lower cycloalkyl group" in the "lower cycloalkyl group which may be substituted" (4) include a $C_{4-7}$cycloalkyl group such as cyclobutyl, cyclopentyl, cyclohexyl, cycloheptyl, etc.

Examples of the "cycloalkenyl group" in the "lower cycloalkenyl group which may be substituted" (4) include a $C_{3-6}$cycloalkenyl group such as cyclopropenyl, cyclobutenyl, cyclopentenyl, cyclohexenyl, etc.

The aryl group (3), the lower cycloalkyl group or lower cycloalkenyl group (4) may have 1 to 5 substituents, preferably 1 to 3 substituents at any substitutable position. Examples of the substituents include an alkoxy group (e.g., a $C_{1-3}$alkoxy group such as methoxy, ethoxy, propoxy, etc.), a halogen atom (e.g., fluorine, chlorine, bromine, iodine), an alkyl group (e.g., a $C_{1-3}$alkyl such as methyl, ethyl, propyl, etc.), an amino group which may be substituted by a lower ($C_{1-3}$)alkyl (e.g., amino, methylamino, dimethylamino, diethylamino), a hydroxyl group, a nitro group, a cyano group, etc.

Examples of the carboxyl group which may be esterified (5) include a carboxyl group, a (lower($C_{1-6}$)alkoxy)carbonyl (e.g., methoxycarbonyl, ethoxycarbonyl, propoxycarbonyl, isopropoxycarbonyl, butoxycarbonyl, isobutoxycarbonyl, tert.-butoxycarbonyl, sec.-butoxycarbonyl, pentyloxycarbonyl, isopentyloxycarbonyl, neopentyloxycarbonyl, tert.-pentyloxycarbonyl, hexyloxycarbonyl, etc.), a ($C_{6-10}$ aryl)oxycarbonyl (e.g., phenoxycarbonyl, 1-naphthoxycarbonyl, etc.), a ($C_{7-10}$aralkyl)oxycarbonyl (e.g., a (phenyl-$C_{1-4}$alkyloxy)carbonyl such as benzyloxycarbonyl, etc.), etc. Among them, carboxyl, methoxycarbonyl, ethoxycarbonyl, etc. are preferable.

Examples of the substituents in the "carbamoyl group or thiocarbamoyl group which may be substituted" (6) and the "amino group which may be substituted" (7) include, for example, a $C_{1-6}$alkyl (e.g., methyl, ethyl, propyl, isopropyl, butyl, isobutyl, sec.-butyl, tert.-butyl, pentyl, isopentyl. neopentyl, hexyl, isohexyl, etc.) which may be substituted, a $C_{3-6}$cycloalkyl group (e.g., cyclopropyl, cyclobutyl, cyclopentyl, cyclohexyl, etc.) which may be substituted, a $C_{6-10}$ aryl group (e.g., phenyl, 1-naphthyl, 2-naphthyl, etc.) which may be substituted, a $C_{7-12}$aralkyl group (e.g., a phenyl-$C_{1-4}$alkyl, a naphthyl-$C_{1-2}$alkyl, etc., such as benzyl, phenethyl, etc.) which may be substituted, a $C_{6-10}$ arylsulfonyl group (e.g., benzenesulfonyl, 1-naphthalenesulfonyl, 2-naphthalenesulfonyl, etc.) which may be substituted, etc. These substituents may be the same or different, and one or two of these substituents may substitute at any substitutable position. Examples of the substituents in the "$C_{1-6}$alkyl which may be substituted", the "$C_{3-6}$cycloalkyl group which may be substituted", the "$C_{6-10}$ aryl group which may be substituted", the "$C_{7-12}$aralkyl group which may be substituted" or the "$C_{6-10}$arylsulfonyl group which may be substituted" include, for example, a halogen (e.g., fluorine, chlorine, bromine, etc.), an alkoxy group which may be substituted by 1 to 3 halogen atoms (e.g., a $C_{1-4}$alkoxy such as methoxy, ethoxy, propoxy, etc., a halogeno-$C_{1-4}$alkoxy such as trifluoromethoxy, 2,2,2-trifluoroethoxy, 2,2,3,3,3-pentafluoropropoxy, etc.), an alkyl group which may be substituted by 1 to 3 halogen atoms (e.g., a $C_{1-4}$alkyl such as methyl, ethyl, propyl, etc., a halogeno-$C_{1-4}$alkyl such as trifluoromethyl, 2,2,2-trifluoroethyl, 2,2,3,3,3-pentafluoropropyl, etc.), a nitro group, etc. One to five of these substituents may substitute at any substitutable position. The nitrogen atom and two substituents on the nitrogen atom in the "amino group which may be substituted" (7) may together form a cyclic amino group. Examples of the cyclic amino groups include, for example, 1-azetidinyl, 1-pyrrolidinyl, piperidino, morpholino, thiomorpholino, 1-piperazinyl, etc.

Examples of the substituents in the "hydroxyl group which may be substituted" (8) and the "thiol group which may be substituted" (9) include, for example, a $C_{1-6}$alkyl (e.g., methyl, ethyl, propyl, isopropyl, butyl, isobutyl, sec.-butyl, tert.-butyl, pentyl, isopentyl, neopentyl, hexyl, isohexyl, etc.) which may be substituted, a $C_{3-6}$cycloalkyl group (e.g., cyclopropyl, cyclobutyl, cyclopentyl, cyclohexyl, etc.), which may be substituted, a $C_{6-10}$ aryl group (e.g., phenyl, 1-naphthyl, 2-naphthyl, etc.) which may be substituted, a $C_{7-12}$aralkyl group (e.g., a phenyl-$C_{1-4}$alkyl, a naphthyl-$C_{1-2}$alkyl such as benzyl, phenethyl, etc.) which may be substituted, etc. Each of the $C_{1-6}$alkyl group, the $C_{3-6}$cycloalkyl group, the $C_{6-10}$ aryl group and the $C_{7-12}$aralkyl group may have 1 to 5 substituents at any substitutable position. Examples of the substituents include, for example, a halogen (e.g., fluorine, chlorine, bromine, etc.), an alkoxy group which may be substituted by 1 to 3 halogen atoms (e.g., a $C_{1-4}$alkoxy such as methoxy, ethoxy, propoxy, etc., a $C_{1-4}$alkoxy substituted by a halogen such as trifluoromethoxy, 2,2,2-trifluoroethoxy, 2,2,3,3,3-pentafluoropropoxy, etc.), an alkyl which may be substituted by 1 to 3 halogen atoms (e.g., a $C_{1-4}$alkyl such as methyl, ethyl, propyl, isopropyl, butyl, etc., a $C_{1-4}$alkyl substituted by a halogen such as trifluoromethyl, 2,2,2-trifluoroethyl, 2,2,3,3,3-pentafluoropropyl, etc.), nitro, amino, cyano, etc.

Examples of the acyl groups (10) include, for example, formyl, a carbonyl group substituted by a hydrocarbon group which may be substituted, a sulfinyl group substituted by a hydrocarbon group which may be substituted, a sulfonyl group substituted by a hydrocarbon group which may be substituted, etc. Examples of the "hydrocarbon group" in the "hydrocarbon group which may be substituted" include a hydrocarbon group, for example, a $C_{1-6}$alkyl group, a $C_{3-6}$cycloalkyl group, a $C_{6-10}$ aryl group (e.g., phenyl, naphthyl, etc.), a $C_{7-12}$aralkyl group (e.g., a phenyl-$C_{1-4}$alkyl, a naphthyl-$C_{1-2}$alkyl, etc.), etc. That is, examples of the acyl groups include, formyl as well as a carbonyl group, a sulfinyl group and a sulfonyl group each of which is substituted by a $C_{1-6}$alkyl (e.g., methyl, ethyl, propyl, isopropyl, butyl, isobutyl, sec-butyl, tert-butyl, pentyl, isopentyl, neopentyl, hexyl, isohexyl, etc.). These acyl groups may have 1 to 5 substituents at any substitutable position. Example of the substituents include, for example, a halogen atom (e.g., fluorine, chlorine, bromine, iodine), a lower alkoxy group (e.g., a $C_{1-4}$alkoxy group such as methoxy, ethoxy, propoxy, etc.), a lower alkyl group (e.g., a $C_{1-4}$alkyl group such as methyl, ethyl, propyl, etc.), etc.

Examples of "the heterocyclic group" in "heterocyclic group which may be substituted" represented by R in the above formulas include, for example, an aromatic heterocyclic group, a saturated or unsaturated non-aromatic heterocyclic group (aliphatic heterocyclic group), each of which has at least one hetero atom selected from the group consisting of an oxygen atom, a sulfur atom and a nitrogen atom, as ring-constituting atom, Among them, an aromatic heterocyclic group is preferable. Examples of the aromatic heterocyclic groups include, for example, a 5 to 7-membered aromatic heterocyclic group containing one of a sulfur atom, a nitrogen atom and an oxygen atom, a 5 or 6 -membered aromatic heterocyclic group containing 2 to 4 nitrogen atoms and a 5 to 6-membered aromatic heterocyclic group containing 1 or 2 nitrogen atoms and one sulfur atom or oxygen atom, etc. These aromatic heterocyclic group may be condensed with a 6-membered ring containing not more than 2 nitrogen atoms, benzene ring or 5-membered ring containing a sulfur atom. Examples of the aromatic heterocyclic groups include, for example, an aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl (1,3,5-triazinyl, 1,2,4-triazinyl), etc.) and an aromatic fused heterocyclic group (e.g., benzofuranyl, isobenzofuranyl, benzo(b)thienyl, indolyl, isoindolyl, 1H-indazolyl, benzimidazolyl, benzoxazolyl, 1,2-benzisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.).

Examples of the non-aromatic heterocyclic groups include a 5 to 7 membered non-aromatic heterocyclic group containing one atom selected from sulfur atom, nitrogen atom and oxygen atom, and a 3 to 7 membered non-aromatic heterocyclic group containing one nitrogen atom and not more than 3 hetero atoms (e.g., nitrogen atom, oxygen atom, sulfur atom), for example, oxylanyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, homopiperidyl, pyrrolinyl, imidazolidinyl, etc. The non-aromatic heterocyclic group may be condensed with a benzene ring, a 6-membered ring containing not more than 2 nitrogen atoms or a 5-membered ring containing a sulfur atom, etc. Examples of the fused non-aromatic heterocyclic groups include, for example, chromanyl, isochromanyl, indolinyl, isoindolinyl, thiochromanyl, isothiochromanyl, etc.

The substituent in the "heterocyclic group which may be substituted" represented by R may substitutes at any substitutable position on the heterocyclic group. One to three of these substituents may substitutes. The examples of the substituents include an alkoxy group which may be substituted by 1 to 3 halogen atoms (e.g., fluorine, chlorine, bromine, iodine) (e.g., a $C_{1-4}$alkoxy such as methoxy, ethoxy, propoxy, etc., a $C_{1-4}$alkoxy substituted by a halogen, such as trifluoromethoxy, 2,2,2-trifluoroethoxy, 2,2,3,3,3-pentafluoropropoxy, etc.), a halogen atom (e.g., fluorine, chlorine, bromine, iodine), alkyl group which may be substituted by 1 to 3 halogen atoms (e.g., fluorine, chlorine, bromine, iodine) (e.g., a $C_{1-4}$alkyl such as methyl, ethyl, propyl, etc., a $C_{1-4}$alkyl substituted by a halogen such as trifluoromethyl, 2,2,2-trifluoroethyl, 2,2,3,3,3-pentafluoropropyl, etc.), a $C_{1-3}$alkyl group such as methyl, ethyl, propyl, isopropyl, etc., a $C_{1-3}$alkoxy group such as methoxy, ethoxy, propoxy, isopropoxy, etc., a halogen atom such as chlorine, fluorine, etc., an aryl group which may be substituted by a hydroxyl group, an amino group, a nitro group or a cyano group (e.g., a$C_{6-10}$ aryl such as phenyl, 1-naphthyl, 2-naphthyl, etc.,), nitro group, etc.

The preferable examples of the "heterocyclic group" in the "heterocyclic group which may be substituted" represented by R include, for example, a 5 or 6-membered nitrogen-containing heterocyclic group such as imidazolyl, pyrrolyl, pyrazolyl, 1,2,3-triazolyl, 1,2,4-triazolyl, tetrazolyl, thiazolyl, isothiazolyl, oxazolyl, isoxazolyl, pyridyl, pyridazinyl, pyrimidinyl, pyrazinyl, 1,3,5-triazinyl, 1,2,4-triazinyl, etc. Especially, imidazolyl, 1,2,4-triazolyl, pyridyl, etc. are the most preferable. Preferable examples of the substituents of the heterocyclic group include alkoxy group which may be substituted by 1 to 3 halogen atoms (e. g., fluorine, chlorine, bromine, iodine) (e.g., a $C_{1-4}$alkoxy such as methoxy, ethoxy, propoxy, etc., a $C_{1-4}$alkoxy substituted by a halogen such as trifluoromethoxy, 2,2,2-trifluoroethoxy, 2,2,3,3,3-pentafluoropropoxy, etc.), a halogen atom (e.g., fluorine, chlorine, bromine, iodine) or an alkyl group which may be substituted by 1 to 3 halogen atoms (e.g., fluorine, chlorine, bromine, iodine) (e.g., a $C_{1-4}$alkyl such as methyl, ethyl, propyl, etc., a $C_{1-4}$alkyl substituted by a halogen such as trifluoromethyl, 2,2,2-trifluoroethyl, 2,2,3,3,3-pentafluoropropyl, etc.), etc. The number of the substituents is preferably 1 to 3.

Examples of the divalent groups represented by X include, for example, a divalent hydrocarbon group which may be substituted, —NR'— (wherein R' is a hydrogen atom or a $C_{1-6}$alkyl group such as methyl, ethyl, propyl, isopropyl, etc.), —O—, —S—, —COO—, —COS—, —CONR'— (wherein R' has the same meaning as defined above), —SO—, —SO$_2$—, —N=N—, or a lower alkylene containing one or two atoms selected from the group consisting of an oxygen atom, a nitrogen atom and sulfur atom, etc.

Examples of the divalent hydrocarbon groups in the "divalent hydrocarbon group which may be substituted" include, for example, a $C_{1-6}$alkylene such as methylene, ethylene, etc., a $C_{2-6}$alkenylene such as ethenylene, etc., a $C_{2-6}$alkynylene such as ethynylene, etc., phenylene, naphthynylene, etc. Among them, a $C_{1-6}$alkylene is preferable, and methylene is the most preferable.

Examples of the substituents of the divalent hydrocarbon group include substituents of the ring $A_2$ mentioned above.

Examples of the lower alkylenes containing one or two atoms selected from the group consisting of an oxygen atom, a nitrogen atom and a sulfur atom include, for example, a $C_{1-4}$alkylene group containing one or two atoms selected from the group consisting of an oxygen atom, a nitrogen atom and a sulfur atom such as —CH$_2$O—, —OCH(CH$_3$)—, —CH$_2$CH$_2$O—, —OCH$_2$O—, —OCH$_2$CH$_2$O—, —CH$_2$NH—, —CH$_2$CH$_2$—, —NHCH(CH$_3$)—, —N(CH$_3$)CH$_2$—, —NHCH$_2$CH$_2$NH—, —CH$_2$S—, —SCH(CH$_3$)—, —CH$_2$CH$_2$S—, —SCH$_2$S—, —SCH$_2$CH$_2$S—, —OCH$_2$CH$_2$NH—, —OCH$_2$CH$_2$S—, —SCH$_2$CH$_2$NH—, etc.

Examples of the ethenylene which may be substituted represented by Z include, for example, a group of the formula:

—CR$^1$=CR$^2$—

(wherein, $R^1$ and $R^2$ each is a hydrogen atom, a fluorine atom, a lower alkyl group which may be substituted, a lower alkoxy group which may be substituted, an aryl group which may be substituted, a lower cycloalkyl group which may be substituted, or a cycloalkenyl group which may be substituted, a carboxyl group which may be esterified, a carbamoyl group which may be substituted, a thiocarbamoyl group which may be substituted, an amino group which may be substituted, an acyl group, a halogen atom, a nitro group or a cyano group).

Examples of the lower alkyls which may be substituted, the lower alkoxy group which may be substituted, the aryl group which may be substituted, the lower cycloalkyl group which may be substituted, the cycloalkenyl group, the carboxyl group which may be esterified, the carbamoyl group which may be substituted, thio carbamoyl group which may be substituted, the amino group which may be substituted, the acyl group, the halogen, the nitro group and the cyano group represented by $R^1$ and $R^2$ includes those mentioned as the substituents of the ring $A_2$.

Preferable examples of the compounds of the formula (I) include, for example, a compound of the formula:

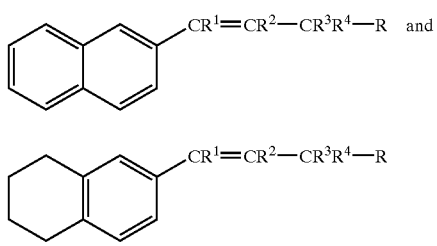

(wherein, $R^1$ and $R^2$ have the same meanings as defined above, $R^3$ and $R^4$ each is a hydrogen atom, a lower alkyl which may be substituted, a lower alkoxy group which may be substituted, an aryl group which may be substituted, a lower cycloalkyl group or a cycloalkenyl group which may be substituted, a carboxyl group which may be esterified, a carbamoyl group which may be substituted, a thio carbamoyl group which may be substituted, an amino group which may be substituted, an acyl group, a halogen, a nitro group or a cyano group), etc.

As the lower alkyl which may be substituted, the lower alkoxy group which may be substituted, the aryl group which may be substituted, the lower cycloalkyl group which may be substituted, or the cycloalkenyl group, the carboxyl group which may be esterified, the carbamoyl group which may be substituted, the thiocarbamoyl group which may be substituted, the amino group which may be substituted, the acyl group, the halogen, the nitro group and the cyano group represented by $R^1$, $R^2$, $R^3$ and $R^4$, those mentioned as the substituents of the ring $A_2$ can be used.

Preferable examples of the compounds of the formulas (I-a) and (I-b) include, for example, a compound of the formulas (I-a) and (I-b) wherein $R^1$, $R^2$, $R^3$ and $R^4$ each is a hydrogen atom and a lower alkyl group which may be substituted, R is imidazolyl or pyridyl, etc. and the most preferable examples include a compound of the formulas (I-a) and (I-b) wherein $R^1$ and $R^2$ each is a hydrogen atom, or a $C_{1-3}$ alkyl group such as methyl, ethyl, propyl, isopropyl, etc., $R^3$ and $R^4$ each is a hydrogen atom, and R is imidazolyl or pyridyl.

The fused ring derivatives represented by the formula (I) of the present invention may form a salt. As the salt, an acid addition salt, for example, a salt of an inorganic acid (for example, a hydrochloric acid salt, a sulfuric acid salt, a hydrobromic acid salt, a phosphoric acid salt, etc. a salt of an organic acid (for example, a acetic acid salt, a trifluoro an acetic acid salt, a succinic acid salt, a maleic acid salt, a fumaric acid salt, a propionic acid salt, a citric acid salt, a tartaric acid salt, an oxalic acid salt, a lactic acid salt, an an oxalic acid salt, a methane sulfonic acid salt, a p-toluene sulfonic acid salt, etc.), etc., a salt with a base ( for example, an alkali metal salt such as a potassium salt, a sodium salt, a lithium salt, etc., an alkaline earth metal salt such as a calcium salt, a magnesium salt, etc., an ammonium salt, a salt of organic base such as a trimethyl amine salt, a triethyl amine salt, a tert-butyldimethyl amine salt, a dibenzylmethyl amine salt, a benzyldimethyl amine salt, a N,N-dimethyl aniline salt, a pyridine salt, a quinoline salt, etc.).

The derivative of the fused ring compound of the formula (I) or (I') or the salt thereof may be hydrated.

Compound (I) and (I') of the present invention may have one or more carbon-carbon double bonds in the molecule. The cis form (Z-form) and trans form (E-form) of geometrical isomers caused by the carbon-carbon double bond are included in the present invention. Compound (I) or (I') of the present invention may have one or more asymmetric carbon in the molecule, and R-configuration and S-configuration as to the asymmetric carbons are also included in the present invention.

Compound (I) can be produced, for example, by the following methods. The following is the abbreviated figure of the reaction scheme, and each symbol in the abbreviated figure has the same meaning as defined above. All the compounds (Ia), (Ib), (Ic), (Id), (Ie), (If) and (Ig) are included in the compound (I) of the present invention.

The starting compound and the intermediates can be used as a free form or a salt thereof like Compound (I). The reaction mixture as it is or the compound isolated by a known method from the reaction mixture can be used for the following reaction.

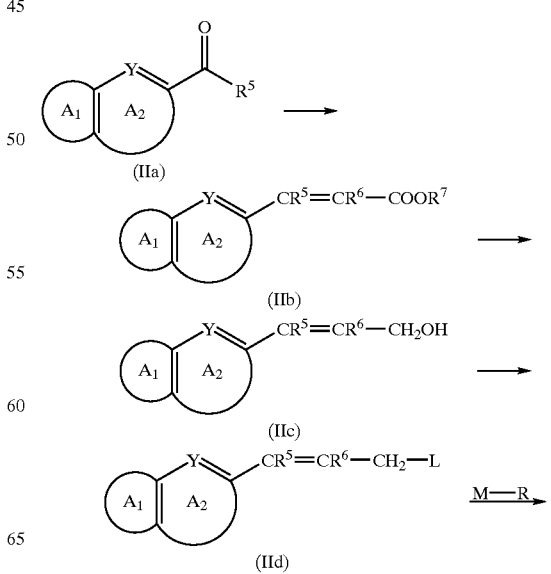

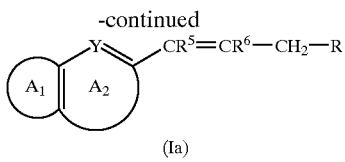

(Ia)

[wherein $R^5$ and $R^6$ each is a hydrogen atom or an alkyl (a $C_{1-6}$lower alkyl group such as methyl, ethyl, propyl, isopropyl, butyl, isobutyl, sec.-butyl, tert.-butyl, pentyl, isopentyl, neopentyl, hexyl, isohexyl, etc.); $R^7$ is an alkyl (a $C_{1-6}$lower alkyl group such as methyl, ethyl, propyl, isopropyl, butyl, isobutyl, sec.-butyl, tert.-butyl, pentyl, isopentyl, neopentyl, hexyl, isohexyl, etc.) or an aralkyl group such as benzyl, etc.; M is a hydrogen atom, an alkali metal, an alkaline earth metal, copper, etc.; L is a leaving group (for example, a halogen atom, methane-sulfonyloxy, p-toluenesulfonyloxy, trifluoromethanesulfonyloxy, etc.); each of the other symbols has the same meaning as defined above.]

The compound (IIb) can be synthesized by subjecting Compound (IIa) to a Wittig type reaction (for example, Wittig reaction, Horner-Emmons reaction, etc.). Examples of the reagents used in a Wittig type reaction include, for example, a phosphonium salt such as a tri phenyl alkylphosphonium salt, etc., Horner-Emmons-type Wittig reagent such as a dimethoxyphosphorylalkyl, a diethoxyphosphorylalkyl, etc., The reagent is used in an amount of 1 to 10 moles, preferably 1 to 3 moles per mole of the starting compound(IIa). The reaction is usually carried out in an organic solvent which does not disturb the reaction. Examples of the organic solvents include, for example, a saturated hydrocarbon such as hexane, pentane, etc., an amide such as N,N-dimethylformamide, N,N-dimethylacetamide, etc., a halogenated hydrocarbon such as dichloromethane, chloroform, etc., an ether such as diethyl ether, dioxane, tetrahydrofuran, etc., an ester such as methyl acetate, ethyl acetate, etc., a nitrile such as acetonitrile, propionitrile, etc., a nitro compound such as nitromethane, nitroethane, etc., an aromatic hydrocarbon such as benzene, toluene, etc. These solvents can be used solely or in combination of two or more kind of solvent. The reaction is usually carried out in the presence of a base. Examples of the bases include an alkali metal hydride, an organic alkali metal, an alkali metal alkoxide, etc. The base is used in an amount of about 1 to 5 mole per mole of the starting compound. The reaction mixture is usually −80° C. to 100° C., preferably −20° C.~50° C., and the reaction time is about 5 minutes to 5 hours.

The ester compound (IIb) is reduced to produce Compound (IIc). Examples of the reducing agents which can be used include, for example, diisobutylaluminum hydride, lithium aluminum hydride, etc. The amount of the reducing agent is about 1 to 5 moles, preferably about 1 to 2 moles per mole of Compound (IIb) though it depends on the kind of the reducing agent used. The reaction is advantageously carried out in a solvent which is not disturb the reaction. Preferable examples of the solvents include, for example, an ether such as tetrahydrofuran, etc., a halogenated hydrocarbon such as dichloromethane, etc., a hydrocarbon such as hexane, toluene, etc. though it is not limited as long as the reaction proceeds.

The reaction time varies depending on the activity of the reducing agent used and the amount of the reducing agent, but usually is 30 minutes to 24 hours, preferably 30 minutes to 10 hours. The reaction temperature is usually −78° C. to 30° C.

Then compound (IIc) is reacted with a reagent such a sulfonyl chloride as thionyl chloride, methanesulfonyl chloride, p-toluenesulfonyl chloride, trifluoromethanesulfonyl chloride, etc. to form Compound (IId). The reagent is usually used in an amount of 1 to 10 mole per mole of the starting compound. The reaction is usually carried out in the presence of a base. As the base, for example, an alkali metal, an alkali metal hydride, a tertiary amine such as diisopropylethylamine, 2,6-di-tert-butylpyridine, 2,6-di-tert-butyl-4-methylpyridine, triethylamine, etc., can be used. The amount of the base used is about 1 to 5 moles per mole of the starting compound. The reaction is usually carried out in an organic solvent which does not influence the reaction. As the organic solvent, for example, a saturated hydrocarbon such as hexane, pentane, etc., a halogenated hydrocarbon such as dichloromethane, etc., an ether such as diethyl ether, dioxane, tetrahydrofuran, etc., an ester such as methyl acetate, ethyl acetate, etc., an aromatic hydrocarbon such as benzene, toluene, etc., can be used. These solvents can be used solely or in combination with two or more in an appropriate ratio. The reaction temperature is usually −80° C. to 100° C., preferably −20° C. to 50° C. The reaction time is 5 minutes to 5 days. The compound (IId) can also be produced by reacting Compound (IIc) with a reagent, for example, carbon tetrabromide, carbon tetrachloride, etc., in the presence of triphenylphosphine, etc. The reaction can be carried out by a known method, for example, J. Org. Chem., 42, 353(1977), etc., or a method similar to the known method.

The compound (Ia) can be produced by reacting Compound (IId) with a compound of the formula: M—R. The amount of the compound M—R is about 1 to 10 moles per mole of Compound (IId). The reaction is usually carried out by using a solvent which is inert to the reaction. As the solvent, for example, an ether such as dimethylformamide, tetrahydrofuran, etc., a halogenated hydrocarbon such as dichloromethane, etc., are mentioned. The reaction time varies depend on the activity of the compound R—M and its amount, but usually is 30 minutes to 24 hours, preferably 30 minutes to 10 hours. The reaction temperature is usually −78° C. to 150° C.

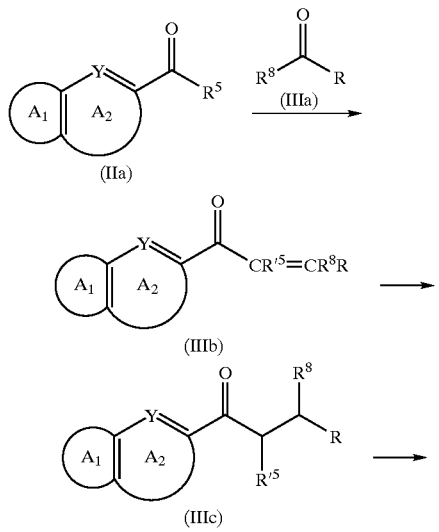

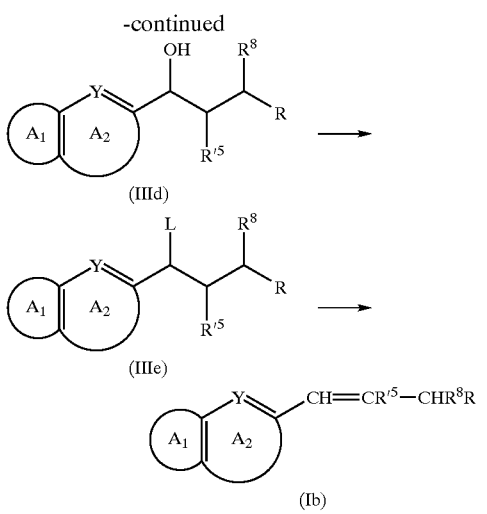

[wherein R'⁵ and R⁸ each is a hydrogen atom or an alkyl (e.g., an alkyl having 1 to 6 carbon atoms such as methyl, ethyl, propyl, isopropyl, butyl, isobutyl, sec.-butyl, tert.-butyl, pentyl, isopentyl, neopentyl, hexyl, isohexyl, etc., and each of the other symbols has the same meaning as defined above].

Compound (IIIb) can be produced by subjecting Compound (IIa) and Compound (IIIa) to the known aldol reaction, followed by dehydration reaction. The reaction is usually carried out in the presence of an acid or a base. As the base, for example, potassium hydroxide, sodium methoxide, potassium tert-butoxide, LDA (lithium diisopropylamide), an alkali metal hydride, etc., can be used. The amount of the base is about 0.01 mole to 5 moles per mole of the starting compound. As the acid, for example, hydrochloric acid, sulfuric acid, p-toluene sulfonic acid, etc., can be used. The amount of the base is about 0.01 mole to 5 moles per mole of the starting compound. The reaction is usually carried out in an organic solvent which does not influence the reaction. Examples of the organic solvents which does not influence the reaction include, for example, a saturated hydrocarbon such as hexane, pentane, etc., a halogenated hydrocarbon such as dichloromethane, etc., an ether such as diethyl ether, dioxane, tetrahydrofuran, etc., an aromatic hydrocarbon such as benzene, toluene, etc., an alcohol such as methanol, ethanol, etc. These solvents can be used solely or in combination of two or more kinds of solvent. The reaction temperature is usually −80° C. to 100° C., preferably −20° C. to 50° C. The reaction time is usually 5 minutes to 10 hours.

Then Compound (IIIb) is subjected to the reduction reaction to produce Compound (IIIc). The reaction is usually carried out in the presence of a reducing catalyst and hydrogen without a solvent or in a suitable solvent. It is preferable to use the reducing agent in an amount of about 0.01 to 100 weight %, preferably about 0.01 to 50 weight % per mole of Compound (IIIb). As the catalytic reduction agent, palladium-black, palladium-carbon, platinum oxide, platinum black, Raney nickel, Raney cobalt, etc., can be mentioned. It is advantageous to use a solvent inert to the reaction in the present reaction. As the solvent, for example, water, an alcohol such as methanol, ethanol, propanol, etc., an ether such as diethyl ether, tetrahydrofuran, dioxane, 1,2-dimethoxyethane, etc., a hydrocarbon such as benzene, toluene, cyclohexane, etc., an ester such as ethyl acetate, etc., an organic acid such as acetic acid, etc. can be used, though it is not limited as long as the reaction proceeds.

These solvents can be used solely or in combination of two or more kinds of solvent. The reaction time varies depending on the activity of the reducing catalyst used and the amount of the reducing catalyst, but usually is 0.5 hour to 24 hours, preferably 0.5 hour to 5 hours. The reaction temperature is usually 0° C. to 120° C., preferably 10° C. to 70° C.

Then ketone compound (IIIc) is subjected to reduction reaction to produce Compound (IIId). As the reducing agent used, for example, sodium borohydride, lithium aluminum hydride, lithium tri-t-butoxyaluminum hydride, lithium tri-sec-butylboro hydride, etc., may be mentioned.

The amount of the reducing agent used is about 1 to 4 moles, preferably about 1 mole per mole of Compound (IIIb). The reaction is advantageously carried out in an solvent which is inert to the reaction. As the solvent, for example, an ether such as tetrahydrofuran, etc., a halogenated hydrocarbon such as dichloromethane, etc., an alcohol such as methanol, etc., a hydrocarbon such as hexane, toluene, etc., are preferable, though it is not limited as long as the reaction proceeds. The reaction time varies depend on the activity of the reducing agent used and the amount of the reducing agent, but usually is 5 minutes to 24 hours, preferably 5 minutes to 5 hours. The reaction temperature is usually −78° C. to 30° C.

Then, Compound (IIId) can be converted to Compound (IIIe) by a similar manner to the reaction converting Compound (IIc) to Compound (IId).

Furthermore Compound (Ib) can be produced by subjecting Compound (IIIe) to 1,2-elimination reaction. The reaction is usually carried out in the presence of a base. As the base, potassium hydroxide, sodium methoxide, collidine, potassium tert-butoxide, diisopropylethylamine, DBU (1,8-Diazabicyclo(5.4.0)undec-7-ene), etc., can be used. The reaction is advantageously carried out in a solvent inert to the reaction. The base itself can be used as a solvent. As the solvent, for example, an ether such as tetrahydrofuran, etc., a halogenated hydrocarbon such as dichloromethane, etc., a hydrocarbon such as dimethylsulfoxide, hexane, toluene, etc., are preferable though it is not limited as long as the reaction proceeds. The reaction time is usually 5 minutes to 24 hours, preferably 5 minutes to 5 hours. The reaction temperature is usually 0° C. to 200° C.

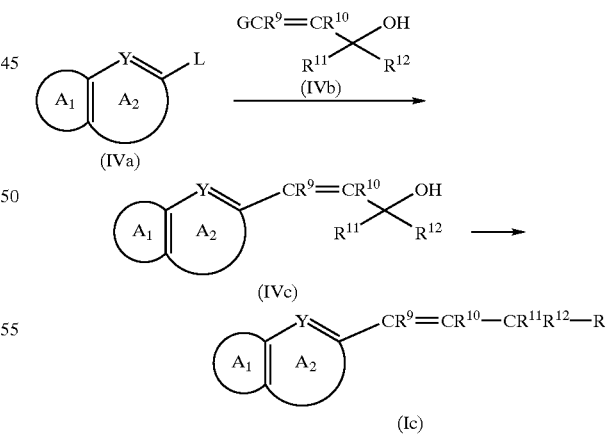

[wherein G is a hydrogen atom, B(OR")₂, SnR"₃, AlR"₂ [R" is an alkyl group (e.g., an alkyl having 1 to 6 carbon atoms such as methyl, ethyl, propyl, isopropyl, butyl, isobutyl, sec-butyl, tert.-butyl, pentyl, isopentyl, neopentyl, hexyl, isohexyl, etc.], MgX, ZnX (X is a halogen atom such as chlorine, bromine, etc.), R⁹, R¹⁰, R¹¹ and R¹² each is a hydrogen atom or an alkyl group (e.g., a lower alkyl group having 1 to 6 carbon atoms such as methyl, ethyl, propyl, isopropyl, butyl, isobutyl, sec.-butyl, tert.-butyl, pentyl, isopentyl, neopentyl, hexyl, isohexyl, etc.,), and each of the other symbols has the same meaning as defined above.]

Compound (IVc) can be produced from Compound (IVa) by a reaction which forms a bond between a carbon atom and a carbon atom (for example, Heck reaction, Suzuki reaction, etc.) by using ethylene compound (IVb) and a transition metal (for example, palladium catalyst, etc.). The reaction is carried out by a known method, for example, method shown in J. Org. Chem., 37, 2320 (1972), Tetrahedron, 50, 2003 (1994), etc., or a similar manner to the known methods.

Further, Compound (Ic) can be produced from Compound (IVc) by a similar manner to the reaction which converts Compound (IIc) to

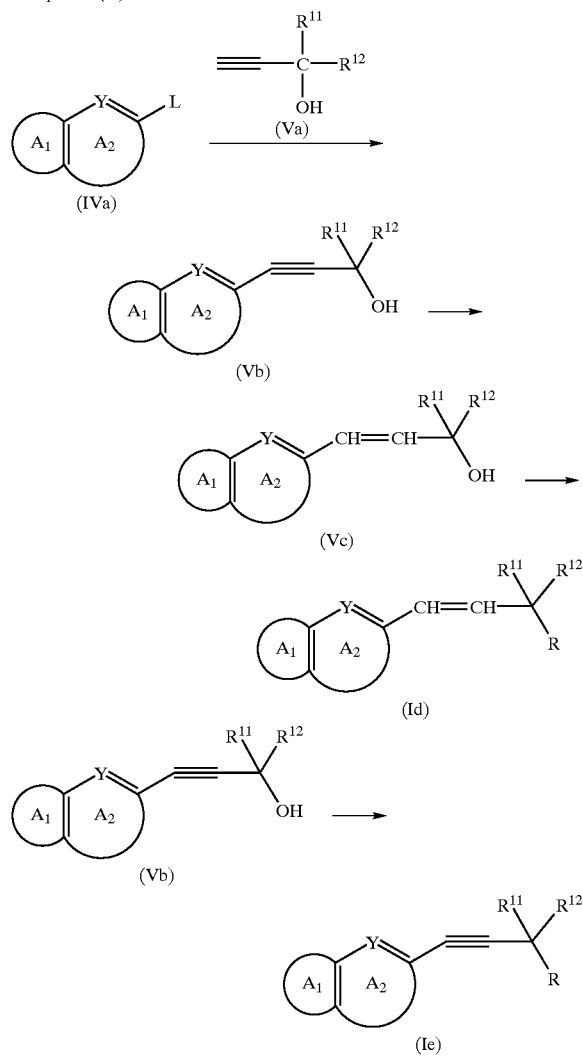

[wherein each symbol has the same meaning as defined above.]

Compound (Vb) can be produced by subjecting Compound (IVa) and Compound (Va) to, for example, the reaction which forms carbon-carbon bond by using palladium catalyst, etc. The reaction is carried out by a known method, for example, reaction shown in Jikkenkagaku-koza 25(VII),404(1991), etc., or a manner similar to those.

Then Compound (Vb) is subjected by reduction reaction to produce Compound (Vc). The reaction is usually carried out in the presence of a reducing catalyst and hydrogen without a solvent or in a suitable solvent. The reducing catalyst is used in an amount of about 0.01 to 50 weight %, preferably about 0.01 to 25 weight % per mole of Compound (Vb). Examples of the reducing catalyst include palladium-black, palladium-carbon, palladium-barium sulfate, palladium-calcium carbonate, etc. In the reaction, the reducing catalyst may be used after reducing the activity of catalyst with an amine such as quinoline, pyridine, etc., a heavy metal such as lead, etc., a sulfur compound, etc. It is advantageous to use a solvent inert to the reaction in the present reaction. Examples of the solvents include, for example, water, an alcohol such as methanol, ethanol, propanol, etc., an ether such as diethyl ether, tetrahydrofuran, dioxane, 1,2-dimethoxyethane, etc., a hydrocarbon such as benzene, toluene, cyclohexane, etc., an amide such as N,N-dimethylformamide, N,N-dimethylacetamide, etc., a nitrile such as acetonitrile, propionitrile, etc., an ester such as ethyl acetate, etc. an organic acid such as formic acid, acetic acid, etc., though it is not limited as long as the reaction proceeds. These solvents can be used solely or in combination of two or more kind of solvent. The reaction time is usually 0.5 hour to 96 hours, preferably 0.5 hour to 10 hours though it varies activity and amount of the reducing agent used. The reaction temperature is usually 0° C. to 120° C., preferably 10° C. to 70° C.

In the reduction reaction, for example, lithium aluminum hydride, Red-Al (NaALH$_2$(OCH$_2$CH$_2$OCH$_3$)$_2$), diisobutyl aluminum hydride, etc., may be used as the reducing agent. Further, the reaction may be carried out in the presence of a base. Examples of the bases include, for example, sodium methoxide, n-butyl lithium, etc. The amount of the reducing agent is usually about 1 to 4 moles, preferably about 1 mole per mole of Compound (Vb). It is advantageous to use a solvent inert to the reaction in the present reaction. As the solvent is mentioned, for example, an ether such as tetrahydrofuran, etc., a halogenated hydrocarbon such as dichloromethane, etc., an alcohol such as methanol, etc., a hydrocarbon such as hexane, toluene, etc., though it is not limited as long as the reaction proceeds. The reaction time varies depending on the activity of the reducing agent used and the amount of the reducing agent, but usually is 30 minutes to 24 hours, preferably 30 minutes to 10 hours. The reaction temperature is usually −78° C.~100° C.

Furthermore, Compound (Id) can be produced from Compound (Vc) by a similar manner to the reaction in which Compound (Ia) is synthesized from Compound (IIc). By a similar manner, Compound (Ie) can be produced from Compound (Vb).

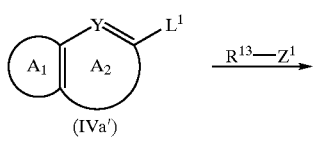

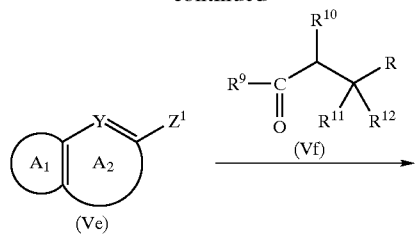

(Ve)

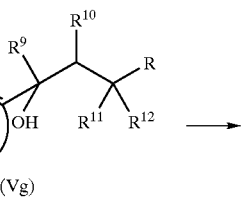

(Vg)

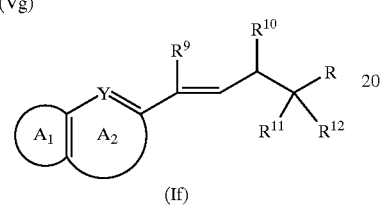

(If)

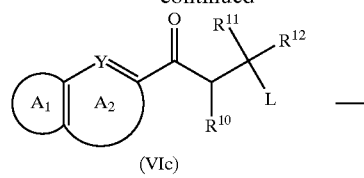

(VIc)

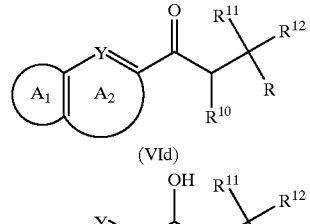

(VId)

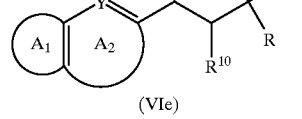

(VIe)

[wherein $L^1$ is a hydrogen atom or a leaving group (e.g., a halogen atom, etc.), $R^{13}$ is a lower alkyl group (e.g., an alkyl group having 1 to 4 carbon atoms such as methyl, ethyl, propyl, butyl, sec-butyl, t-butyl, etc.), Z is a lithium atom or Mg—X (X is a halogen atom such as chlorine, bromine, etc.), and each of the other symbols has the same meaning as defined above.]

Compound (Vg) can be produced by introducing Compound (IVa') to Compound (Ve) by using a metal compound $R^{13}$—$Z^1$, followed by reacting Compound (Ve) with a carbonyl compound (Vf). The reaction can be carried out by a per se known manner, for example, a manner shown in Shin-jikkenkagaku-koza Vol. 14, p511 (Maruzen Co. Japan) or a manner similar to these methods.

Further, Compound (If) can be produced from Compound (Vg) by a similar manner to the method which introduces Compound (IIId) to Compound (Ib). Compound (If) can also be produced by treating Compound (Vg) under acidic condition. Examples of the acids used include hydrochloric acid, methanesulfonic acid, p-toluenesulfonic acid, etc. The reaction can be carried out in an solvent inert to the reaction. Examples of the solvents include an ether (e.g., tetrahydrofuran, diethoxyethane, etc.), a hydrocarbon (e.g., an aromatic hydrocarbon such as benzene, toluene, xylene, etc.). The reaction time is usually 5 minutes to 48 hours. The reaction temperature is usually 0° C. to 200° C., preferably 40° C. to 120° C.

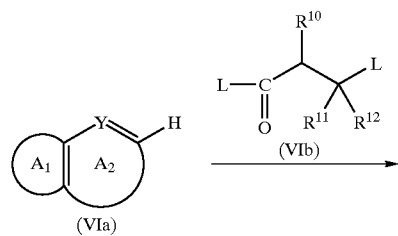

[wherein each symbol has the same meaning as defined above.]

The carbonyl compound (VIc) can be produced by subjecting Compound (VIa) and Compound (VIb) to a known Friedel-Crafts reaction, for example, a manner shown in Shin-jikkenkagaku-koza Vol. 14, p511 (Maruzen Co. Japan) or a manner similar to these methods. Compound (VId) can be produced from Compound (VIc) by a similar manner to the reaction in which Compound (IId) is introduced to Compound (Ia). Then Compound (VIe) can be produced from Compound (VId) by a similar manner to the reaction in which Compound (IIIc) is introduced to Compoud (IIId). Then Compound (Ig) can be produced from Compound (VIe) by a similar reaction in which Compound (Vg) is introduced to Compound (If).

When the desired compound is obtained in free form, the compound may be converted to a salt by a conventional manner. When the desired compound is obtained as a salt, the compound can be converted to free form by a conventional manner. Compound (I) thus obtained can be isolated from the reaction mixture and purified by a known procedure such as phase transfer, concentration, solvent extraction, fractional distillation, crystallization, recrystallization, chromatography, etc. In the above reactions, an amino group, a carboxyl group, a hydroxy group, each of which is not involved in the reaction, in the compound or a salt thereof which is to be reacted may be protected. The protection with a protecting group and deprotection can be carried out by a known manner. Examples of the protecting groups of an amino group include, for example, formyl, a $C_{1-6}$alkylcarbonyl (for example, acetyl, propionyl, etc.), a phenyl carbonyl, a $C_{1-6}$alkyl-oxycarbonyl (for example, methoxycarbonyl, ethoxycarbonyl, etc.), phenyloxycarbonyl, a $C_{7-10}$aralkyloxycarbonyl (for example, a phenyl-$C_{1-4}$alkyloxy-carbonyl such as benzyloxycarbonyl, etc.), trityl, phthaloyl or N,N-dimethylaminomethylene, etc., each of which may be substituted. Examples of the substituents include a halogen atom (for example, fluorine, chlorine, bromine, iodine, etc.), formyl, a $C_{1-6}$alkyl-carbonyl (for example, acetyl, propionyl, valeryl, etc.), nitro, etc. The number of substituents is about 1 to 3.

Examples of the protecting groups of a carboxyl group include, for example, a $C_{1-6}$alkyl (for example, methyl, ethyl, propyl, isopropyl, butyl, tert-butyl, etc.), phenyl, trityl or silyl, etc., each of which may be substituted. Examples of the substituents include, a halogen atom (for example, fluorine, chlorine, bromine, iodine, etc.), formyl, a $C_{1-6}$alkyl-carbonyl (for example, acetyl, propionyl, valeryl, etc.), nitro, etc. The number of substituents is about 1 to 3.

Examples of the protecting groups of the hydroxy group include, for example, a $C_{1-6}$alkyl (for example, methyl, ethyl, propyl, isopropyl, butyl, tert-butyl, etc.), phenyl, a $C_{7-10}$aralkyl (for example, a phenyl-$C_{1-4}$alkyl such as benzyl, etc.), formyl, a $C_{1-6}$alkyl-carbonyl (for example, acetyl, propionyl, etc.), phenyloxycarbonyl, benzoyl, a ($C_{7-10}$aralkyloxy)carbonyl (for example, a phenyl-$C_{1-4}$alkyloxycarbonyl such as benzyloxycarbonyl, etc.), pyranyl, furanyl or silyl, etc., each of which may be substituted. Examples of the substituents include a halogen atom (for example, fluorine, chlorine, bromine, iodine, etc.), a $C_{1-6}$alkyl (for example, methyl, ethyl, propyl, etc.), phenyl, a $C_{7-10}$aralkyl (for example, a phenyl-$C_{1-4}$alkyl such as benzyl, etc.), nitro, etc. The number of substituents is about 1 to 4.

The deprotection reaction is carried out by a known manner or a similar manner thereof. Examples of the deprotection reactions include a manner treating with, for example, acid, base, reduction, ultraviolet ray, hydrazine, phenyl hydrazine, sodium N-methyldithiocarbamate, tetrabutylammonium fluoride, palladium acetate, etc.

When Compound (I) is diastereomer, conformer, etc., Compound (I) can be isolated and purified by a isolation procedure or purification procedure mentioned above, if desirable. When Compound (I) is a racemate, (+)-form and (−)-form of Compound (I) can be isolated by a usual optical resolution procedure. When Compound (I) has a basic group, it can be converted to a salt with an acid by a known manner.

Compound (I) and (I') has superior effect for medicine, and especially has a superior inhibitory activity of steroid $C_{17,20}$-lyase. Compound (I) and (I') is less toxic and has little adverse side effect. Compound (I) and (I') is useful for the preventing and treating a mammal (for example, humans, bovines, horses, dogs, cats, monkeys, mice, rats, etc., especially humans) suffering from various disease such as (1) primary cancer of malignant tumor (for example, prostate cancer, breast cancer, uterine cancer, ovarian cancer, etc.), and its metastasis and recurrence, (2) various symptoms accompanied with these cancer (for example, pain, cachexia, etc.), (3) prostatic hypertrophy, virilism, hirsutism, male pattern alopecia, precocious puberty, endometriosis, uterus myoma, adenomyosis of uterus, mastopathy, polycystic ovary syndrome, etc.

While Compound (I) and (I') has a superior effect when used alone, the effect can be promoted by using the compound (I) and (I') in combination with other medicaments and remedies. Examples of the medicaments and remedies, include but are not limited to, for example, a sex hormone, an alkylating agent, an antimetabolite, an antitumor antibiotic, a plant alkaloid, an immunotherapy, etc.

Examples of the hormone-like agents include, for example, Fosfestrol, Diethylstilbestrol, chlorotrianisene, Medroxyprogesterone acetate, Megestrol acetate, Chlormadinone acetate, Cyproterone acetate, antiestrogens (for example, Tamoxifen, Toremifene citrate, etc.), LH-RH agonist (for example, Goserelin acetate, Buserelin, Leuprorelin, etc.), Droloxifene, Epitiostanol, Ethinylestradiol sulfonate, LH—RH antagonist (for example, Cetrorelix, Ganirelix, etc.) aromatase inhibitors (for example, Fadrozole, Anastrozole, Letrozole, Exemestane, Vorozole, Formestane, etc.), 5α-reductase inhibitors (for example, Finasteride, etc.), anti-androgens (for example, Flutamide, Bicalutamide, etc.), Retinoid and suppressing agents of Retinoid metabolism (for example, Liarozole, etc.), etc.

Examples of the alkylating agents include, for example, Nitrogen mustard, Nitrogen mustard N-oxide hydrochloride, Chlorambucil, Cyclophosphamide, Ifosfamide, Thiotepa, Carboquone, Improsulphan tosilate, Busulfan, Nimustine, Mitobronitol, Melphalan, Dacarbazine, Ranimustine, Estramustine phosphate sodium, Triethylenemelamine, Carmustine, Lomustine, Streptozocin, Pipobroman, Ethoglucid, Carboplatin, Cisplatin, Miboplatin, Nedaplatin, Oxaliplatin, Altretamine, Ambamustine, Dibrospidium chloride, Fotemustine, Prednimustine, Pumitepa, Ribomustin, Temozolomide, Treosulfan, Trofosfamide, Zinostatin stimalamer, etc.

Examples of the antimetabolites include, for example, Mercaptopurine, Thioinosine, Methotrexate, Enocitabine, Cytarabine, Cytarabine ocfosfate, Ancitabine hydrochloride, 5-FU analogues (for example, Fluorouracil, Tegafur, UFT, Doxifluridine, Carmofur, Furtulon, Neofurtulon etc.), Aminopterin, Leucovorin calcium, Tabloid, Butocin, Calcium folinate, Calcium levofolinate, Cladribine, Emitefur, Fludarabine, Gemcitabine, Hydroxycarbamide, Pentostatin, etc.

Example of antitumor antibiotics include, for example, Actinomycin D, Actinomycin C, Mitomycin C, Chromomycin A3, Bleomycin hydrochloride, Bleomycin sulfate, Peplomycin sulfate, Daunorubicin hydrochloride, Doxorubicin hydrochloride, Aclarubicin hydrochloride, Pirarubicin hydrochloride, Epirubicin hydrochloride, Neocarzinostatin, Mithramycin, Sarkomycin, Carzinophilin, Mitotane, Zorubicin hydrochloride, Mitoxantrone hydrochloride, Taxol, etc.

Examples of the plant alkaloids include, for example, Etoposide, Etoposide Phosphate, Vinblastine sulfate, Vincristine sulfate, Vindesine sulfate, Teniposide, Paclitaxel, Vinorelbine, etc.

Examples of the immunotherapies (BRM) include, for example, Picibanil, Krestin, Sizofiran, Lentinan, Ubenimex, Interferons, Interleukins, Macrophage-colony stimulating factor, granules stimulating factor of spheroid colony, Erythropoietin, Lymphotoxin, BCG vaccine, Corynebacterium parvum, Levamisole, Polysaccharide-K, Procodazol, etc.

Others include L-asparaginase, Aceglatone, Procarbazine hydrochloride, Doxorubicin, Protoporphyrin, Hematoporphyrin, topoisomerase I inhibitors (for example, Irinotecan, etc.), topoisomerase II inhibitors (for example, Retinoid, Vitamin D, etc.), inhibitor of proliferation factor (for example, Suramin, etc.), α-broker (for example, Tamsulosin hydrochloride, etc.), Angiogenesis inhibitors, etc.

Therapies other than chemotherapies, such as an operation including orchidectomy, thermotherapy, radiotherapy, etc., can be conducted together with the administration of Compound (I) and (I').

Examples of the pharmaceutically acceptable carriers include various organic or inorganic carriers which are used as a pharmaceutical ingredients. Expipients, lubricants, binders, disintegrators, thickeners can be used for solid preparations; solvents, dispersants, solubilizing agents, suspending agents, isotonic agents, buffer agents, soothing agents, etc., can be used for liquid preparations. If necessary, additives such as preservatives, antioxidants, coloring agents, sweetening agents, etc., can be used. Examples of the preferable exipients include, for example, lactose, saccharose, D-mannitol, starch, crystalline cellulose, light anhydrous silicic acid, etc. Examples of the preferable lubricants include, for example, magnesium stearate, calcium stearate, talc, colloidal silica, etc. Examples of the preferable binders include, for example, crystalline cellulose, saccharose, D-mannitol, dextrin, hydroxypropylcellulose, hydroxypropylmethylcellulose, polyvinyl pyrolidone, etc. Examples of the preferable disintegrators include, for example, starch, carboxymethylcellulose, carboxymethylcellulose calcium, crosscarmelose sodium, carboxymethyl starch sodium, etc. Examples of the preferable thickeners include, for example, natural rubbers, cellulose derivatives, acrylic acid polymers, etc. Examples of the preferable solvents include, for example, water for injection, alcohol, propyleneglycol, Macrogol, sesame oil, corn oil, etc. Examples of the preferable dispersants include, for example, Tween 80, HCO 60, polyethylene glycol, carboxymethylcellulose, sodium alginate, etc. Examples of the preferable solbilizing agents include, for example, polyethylene glycol, propyleneglycol, D-mannitol, benzyl benzoate, ethanol, trisaminomethane, cholesterol, triethanolamine, sodium carbonate, sodium citrate, etc. Examples of the preferable suspending agents include, for example, a surfactant such as stearyl triethanolamine, sodium laurylsulfate, lauryl aminopropionic acid, lecithin, benzalkonium chloride, benzethonium chloride, glycerin monostearate, etc.; for example, hydrophilic polymer such as polyvinylalcohol, polyvinyl pyrolidone, sodium carboxymethyl cellulose, methylcellulose, hydroxymethylcellulose, hydroxyethylcellulose, hydroxypropylcellulose, etc. Examples of the preferable isotonic agents include, for example, sodium chloride, glycerin, D-mannitol, etc. Examples of the preferable buffer agents include, for example, buffer solution such as phosphoric acid salt, acetic acid salt, carbonate, citric acid salt, etc. Examples of the preferable soothing agents include, for example, benzyl alcohol, etc. Examples of the preferable preservatives include, for example, paraoxybenzoates, chlorobutanol, benzyl alcohol, phenethylalcohol, dehydroacetic acid, sorbic acid, etc. Examples of the preferable antioxidants include, for example, sulfurous acid salt, ascorbic acid, etc.

The pharmaceutical preparation of the present invention can be manufactured by the usual manner. The ratio of Compound (I) and (I') contained in a pharmaceutical preparation is usually 0.1 to 100% (w/w). Examples of the embodiments of the pharmaceutical preparation are as follows:

(1) Tablets, Powder, Granules, Capsules

These preparations can be prepared by adding, for example, exipients, disintegrators, binders or lubricants, etc., to Compound (I) and (I'), by compressive molding the mixture and, if necessary, by coating for masking of taste, enteric or sustained release.

(2) Injections

These preparations can be prepared by dissolving Compound (I) and (I') in aqueous injection together with, for example, dispersants, preservatives, isotonic agents, etc., or by dissolving, dispersing or emulsifying Compound (I) and (I') in a vegetable oil such as olive oil, sesame oil, cotton seed oil, corn oil, etc., or propyleneglycol, etc., to give an oily injection.

(3) Suppositories

These preparations can be produced by preparing a liquid composition containing Compound (I) and (I'), which may be oily, aqueous solid like or aqueous semisolid like. Examples of the oily bases used for the composition include, for example, triglycerin ester of long-chain fatty acid (for example, cacao butter, witepsols, etc.), middle-chain fatty acid (for example, migriols, etc.), vegetable oils (for example, sesame oil, soybean oil, cotton seed oil, etc.), etc. Examples of the aqueous gel bases include, for example, natural rubber, cellulose derivative, vinyl polymer, acrylic acid polymer, etc.

The content of Compound (I) and (I') in these preparation is usually 0.01 to 50%, though it varies depending upon the kind of pharmaceutical preparation.

The rate of the compound of the present invention in the above pharmaceutical preparation, varies depending upon the compound used, kind of animal to which the compound is administered, number of administration times, etc. The daily dose of the compound of the present invention, for example, for adult humans suffering from solid tumors (a patient suffering from, for example, prostate cancer), is usually about 0.001 to about 500 mg/kg-weight, preferably about 0.1 to about 40 mg/kg-weight, more preferably about 0.5 to about 20 mg/kg-weight. When Compound (I) and (I') is non-orally administered or when it is administered in combination with another anti-cancer agent, Compound (I) and (I') is administered in a smaller amount mentioned then above. The actual dose of Compound (I) and (I') administered are decided by a doctor by taking the kind of compound, type of pharmaceutical preparation, age of the patient, body weight, sex, degree of disease, administration route, administration term and its interval, etc., into consideration, and the dose may be changed by a doctor.

The pharmaceutical preparation can be administered orally or parenterally. Examples of the parenteral administration routes include intravenous, intramuscular, subcutaneous, intranasal, intradermal, instillation, intracerebral, intrarectal, intravaginal and intraperitoneal, etc.

The above mentioned administration term and administration interval vary depending upon the various conditions and are decided by a doctor. As the administration, there may be mentioned divided administration, daily administration, intermittent administration, high dose administration therapy in short term, repeat administration, etc. It is preferable to administer the compound, for example, once to several times a day (especially two or three times a day). It is possible to administer the compound once to several times a day when using oral administration. It is also possible to administer the compound as a sustained release preparation. It is also possible to administer the compound by intravenous drip infusion over a long time.

BEST MODE FOR CARRYING OUT THE INVENTION

The present invention is hereinafter described in more detail by means of the following Examples, pharmaceutical preparations and Experimental Examples, but these are merely described as examples and they are not intended to limit the present invention. The meanings of the following abbreviated symbols are as follows.

s:singlet, d:doublet, t:triplet, q:quartet, dd:double doublet, dt:double triplet, m:multiplet, br:broad, J:coupling constant, room temperature: 0~30° C., DMF:dimethylformamide, THF:tetrahydrofuran.

EXAMPLE 1

Preparation of 1-[(E)-3-(2-naphthyl-2-propen-1-yl]-1H-imidazole

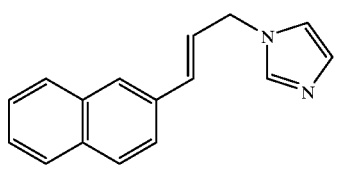

(i) Preparation of methyl (E)-3-(2-naphthyl)acrylate

A mixture of 2-naphthaldehyde (6.00 g) and methyl (triphenyl-phosphoranylidene)acetate (13.0 g) in toluene (100 ml) was refluxed for 14 hours. After removal of the solvent, the residue was chromatographed on silica gel (hexane:ethyl acetate:$CH_2Cl_2$=4:1:4) followed by recrystallization from hexane-cyclohexane to give the titled compound (7.19 g) as a white solid.

$^1$H-NMR ($CDCl_3$) δ: 3.84(3H,s), 6.56 (1H,d,J=16 Hz), 7.51 (2H,m), 7.67 (1H,dd,J=8.8, 1.6 Hz), 7.86(5H,m).

(ii) Preparation of (E)-3-(2-naphthyl)-2-propen-1-ol

A solution of diisobutylaluminum hydride in toluene (1.5M, 18 ml) was added dropwise to a solution of methyl (E)-3-(2-naphthyl)-acrylate (2.52 g) in $CH_2Cl_2$ at −78 °C. and the mixture was stirred at −78° C. for 1 hour. Saturated aqueous solution of $NH_4Cl$ was added to the mixture and organic layer was washed with 1N HCl and brine, dried and concentrated. The residue was crystallized from $CH_2Cl_2$-hexane to give the titled compound (1.78 g) as a white solid.

$^1$H-NMR ($CDCl_3$) δ: 4.38(2H,br), 6.48(1H,dt,J=5.6, 16.0 Hz), 6.78(1H,d,J=16.0 Hz), 7.45(2H,m) 7.60(1H,dd,J=1.8, 8.8 Hz), 7.79(4H,m).

(iii) Preparation of (E)-1-chloro-1-(2-naphthyl)-2-propene

Thionyl chloride (2.1 ml) was added to a solution of 3-(2-naphthyl)-2-propen-1-ol (1.77 g) in $CH_2Cl_2$ (50 ml) at 0° C. and the mixture was refluxed for 2 hours. The mixture was washed with water and brine, dried and concentrated to give the titled compound (1.91 g) as a white solid.

$^1$H-NMR ($CDCl_3$) δ: 4.31(2H,d,J=7.2 Hz), 6.45(1H,dt,J= 7.2, 15.8 Hz), 6.83(1H,d,J=15.8 Hz), 7.47(2H,m), 7.59(1H, d,J=8.6 Hz), 7.79(4H,m).

(iv) Preparation of 1-[(E)- 3-(2-naphthyl-2-propen-1-yl]-1H-imidazole

A mixture of (E)-1-chloro-1-(2-naphthyl)-2-propene (0.931 g) and 1H-imidazole (1.10 g) in dimethylformamide (DMF, 20 ml) was heated at 100° C. for 2 hours. The mixture was concentrated, and the residue was washed with water, dried and concentrated. The residue was purified by silica gel chromatography ($CH_2Cl_2$-MeOH=10:1). Recrystallization from $CH_2Cl_{1-2}$-hexane gave the titled compound (0.533 g) as a colorless powder.

$^1$H-NMR($CDCl_3$) δ:4.76(2H,d, J=6.2 Hz), 6.40 (1H, dt, J=6.2, 15.7 Hz), 6.68 (1H, d, J=15.7 Hz), 7.00 (1H, s), 7.49 (4H, m), 7.78 (4H, m).

EXAMPLE 2

Preparation of 1-[(E)-3-(2-naphthyl)-2-buten-1-yl]-1H-imidazole

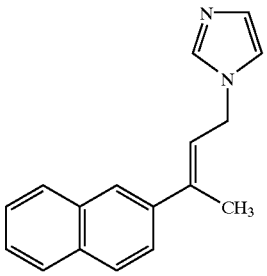

(i) Preparation of methyl (E)-3-(2-naphthyl)crotonate NaH (60% oil dispersion, 2.55 g) was washed with hexane and was suspended in THF (80ml). Methyl diethylphosphonoacetate (13.50 g) was added to the suspension at 0° C. and the mixture was stirred under ice cooling for 30 minutes. 2-Acetonaphtone (10.10 g) was added to the mixture and stirred at room temperature for 16 hours. The reaction was quenched by the addition of water. The organic layer was washed with water and brine, dried over $MgSO_4$ and concentrated. The residue was purified by silica gel chromatography (hexane- ethyl acetate 15:1) followed by recrystallization from hexane to give the titled compound (6.35 g) as a white solid.

$^1$H-NMR ($CDCl_3$) δ: 2. 70 (3H, d, J=1.4 Hz), 3.79 (3H, s), 6.30 (1H, q, J=1.2 Hz), 7.54(3H, m), 7.88 (4H, m).

(ii) Preparation of (E)-3-(2-naphthyl )-2-buten-1-ol

A solution of diisobutylaluminum hydride in toluene (1.5M, 45 ml) was added dropwise to a solution of methyl (E)-3-(2-naphthyl)crotonate (6.01 g) in $CH_2Cl_2$ at −78° C. and the mixture was stirred at −78° C. for 4 hours. 1N-Hhydrochloric acid and saturated aqueous solution of $NH_4Cl$ were added to the mixture and organic layer was washed with 1N HCl and brine, dried and concentrated. The residue was crystallized from hexane to give the titled compound (5.16 g) as a white solid.

$^1$H-NMR ($CDCl_3$) δ: 2.19 (3H, s), 4.43 (2H, d, J=6.6 Hz), 6. 14 (1H, m), 7.46 (2H, m), 7.60 (1H, dd, J=2.0, 8.8 Hz), 7.80 (4H, m).

(iii) Preparation of (E)-1-chloro-3-(2-naphthyl)-2-butene

Thionyl chloride (5.0 ml) was added to a solution of (E)-3-(2-naphthyl)-2-buten-1-ol (4.59 g) in $CH_2Cl_2$ (30 ml)at 0° C. and the mixture was refluxed for 4 hours. The mixture was washed with water, saturated $NaHCO_3$ solution and brine, dried and concentrated. The residue was washed with hexane to give the titled compound (1.22 g) as a white solid.

$^1$H-NMR ($CDCl_3$) δ: 2.26 (3H, d, J=1.6 Hz), 4.43 (2H, d, J=8.0 Hz), 6.16 (1H, m), 7.52 (3H, m), 7.84 (4H, m).

(iv) Preparation of 1-[(E)-3-(2-naphthyl)-3-buten-1-yl]-1H-imidazole

A mixture of (E)-1-chloro-1-(2-naphthyl)-2-butene (1.206 g) and 1H-imidazole (0.797 g) in DMF (25 ml) was heated at 100° C. for 6 hours. The mixture was concentrated and the residue was washed with water and brine, dried and concentrated. The residue was purified by silica gel chromatography ($CH_2Cl_2$-MeOH=10:1) followed by crystallization from $CH_2Cl_2$-cyclohexane to give the titled compound (0.806 g) as a colorless powder.

¹H-NMR (CDCl₃) δ: 2.28 (3H, d, J=0.8 Hz), 4.80 (2H, d, J=7.0 Hz), 6.05 (1H, m), 7.00 (1H, s), 7.11 (1H, s), 7.50 (4H, m), 7.83 (4H, m).

IR (KBr): 1506, 1226, 1075, 865 cm⁻¹.

EXAMPLE 3

Preparation of 1-[(E)-2-methyl-3-(2-naphthyl)-2-propen-1-yl]-1H-imidazole

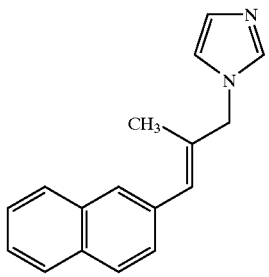

(i) Preparation of methyl (E)-2-methyl-3-(2-naphthyl)acrylate NaH (60% oil dispersion, 1.83 g) was washed with hexane and was suspended in THF (50 ml). Methyl diethylphosphonoacetate (8.31 g) was added to the suspension under ice cooling and the mixture was stirred at room temperature for 15 minutes. 2-Naphthoaldehyde (4.74 g) was added to the mixture and stirred at room temperature for 24 hours. The reaction was quenched by the addition of water. The organic layer was washed with water and brine, dried and concentrated. The residue was recrystallized from hexane to give titled compound (3.93 g) as a white solid.

¹H-NMR (CDCl₃) δ: 2.21 (3H, d, J=1.4 Hz), 3.85 (3H, s), 7.52 (3H, m), 7.85 (5H, m).

(ii) Preparation of (E)-2-methyl-3-(2-naphthyl)-2-propen-1-ol

A solution of diisobutylaluminum hydride in toluene (1.5M, 26 ml) was added dropwise to a solution of methyl (E)-2-methyl-3-(2-naphthyl)acrylate (3.52 g) in CH₂Cl₂ (100 ml) at −78° C. and the mixture was stirred at −78° C. for 1 hour. The mixture was washed with 1N HCl and brine, dried and concentrated. The residue was crystallized from CH₂Cl₂-hexane to give the titled compound (2.89 g) as a white solid.

¹H-NMR (CDCl₃) δ: 1.99 (3H, d, J=1.4 Hz), 4.25 (2H, s), 6.68 (1H, s), 7.46 (3H, m), 7.80 (4H, m).

(iii) Preparation of 1-[(E)-2-methyl-3-(2-naphthyl)-2-propen-1-yl]-1H-imidazole

Methanesulfonyl chloride (0.38 ml) was added to a cooled (0° C.) mixture of (E)-2-methyl-3-(2-naphthyl)-2-propen-1-ol (0.81 g), triethylamine (1.1 ml) and catalytic amount of 4-dimethylaminopyridine in CH₂Cl₂ (20 ml). After being stirred at room temperature for 6 hours, the mixture was washed with water and brine, dried over MgSO₄ and concentrated in vacuo. The residue was dissolved in DMF (20 ml). Imidazole (0.75 g) was added to the solution and the mixture was stirred at 100° C. for 4 hours. After removal of the solvent, the residue was washed with water and brine, dried over Na₂SO₄ and concentrated. The residue was chromatographed on silica gel (CH₂Cl₂—MeOH=10:1) followed by recrystallization from CH₂Cl₂-hexane-cyclohexane to give the titled compound (0.806 g) as a colorless powder.

¹H-NMR (CDCl₃) δ: 1.88 (3H, d, J=1.2 Hz), 4.65 (2H, s), 6.54 (1H, s), 7.00 (1H, s), 7.13 (1H, s), 7.38 (1H, dd, J=1.4, 8.4 Hz), 7.47 (2H, m), 7.58 (1H, s), 7.70 (1H, s), 7.82 (3H, m).

EXAMPLE 4

Preparation of 3-[(E)-3-(2-naphthyl)-2-propen-1-yl]pyridine and 3-[(Z)-3-(2-naphthyl)-2-propen-1-yl]pyridine

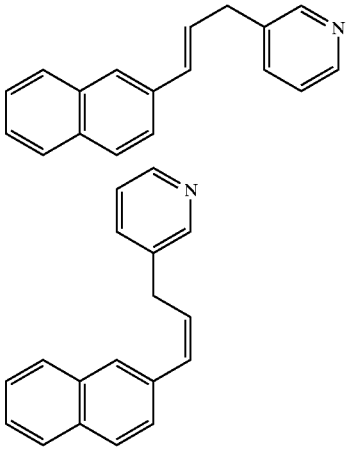

(i) Preparation of (2-naphthyl) [(E)-2-(3-pyridyl)-1-ethenyl]ketone

A 28% solution of sodium methoxide in MeOH (0.90 g) was added to a stirred mixture of nicotinaldehyde (9.70 g) and methyl 2-naphthyl ketone (15.26 g) in MeOH (150 ml). Sodium sulfate (10 g) was added to the mixture and the mixture was stirred for 30 hours. The mixture was diluted with ethyl acetate, washed with water and brine, dried and concentrated. The residue was recrystallized from cold MeOH to give the titled compound (10.68 g).

¹H-NMR (CDCl₃) δ: 7.40 (1H, m), 7.62 (2H, m), 7.77 (1H, d, J=15.8 Hz), 7.88 (1H, d, J=15.8 Hz), 7.99 (4H, m), 8.12 (1H, dd, J=1.8, 8.6 Hz), 8.56 (1H, m), 8.66 (1H, dd, J=1.6, 4.8 Hz), 8.92 (1H, d, J=1.8 Hz).

(ii) Preparation of (2-naphthyl) [2-(3-pyridyl)ethyl]ketone

A mixture of (2-naphthyl) [(E)-2-(3-pyridyl)-1-ethenyl]ketone (5.02 g) and palladium black (0.15 g) in AcOH—MeOH—CH₂Cl₂ (4 ml/50 ml/20 ml) was stirred under hydrogen atmosphere at room temperature for 3 hours. The catalyst was filtered off and the filtrate was concentrated in vacuo. The residue dissolved in ethyl acetate, washed with saturated aqueous NaHCO₃ solution and brine, and dried. After removal of the solvent, the residue was recrystallized from hexane-ethyl acetate to give the titled compound (3.48 g) as colorless prisms.

¹H-NMR (CDCl₃) δ: 3.15 (2H, t, J=7.5 Hz), 3.47 (2H, t, J=7.5 Hz), 7.24 (1H, dd, J=4.8, 7.0 Hz), 7.60 (3H, m), 7.96 (4H, m), 8.47 (2H, dd, J=1.6, 4.8 Hz), 8.58 (1H, d, J=1.8 Hz).

(iii) Preparation of 1-(2-naphthyl)-3-(3-pyridyl)propan-1-ol

To a solution of (2-naphthyl) [2-(3-pyridyl)ethyl]ketone (2.14 g) in MeOH (40 ml) was added NaBH₄ (0.34 g) and the mixture was stirred at room temperature for 30 minutes. After removal of the solvent, the residue was extracted with ethyl acetate. The extract was washed with water and brine, dried and concentrated to give the titled compound (1.56 g) as colorless prisms.

¹H-NMR (CDCl₃) δ: 2.15 (2H, m) , 2.68 (3H, m) , 4.83 (3H, dd, J=5.4, 7.6 Hz), 7.18 (1H, dd, J=4.8, 7.0 Hz), 7.49 (4H, m), 7.82 (4H, m), 8.40 (2H, m).

(iv) Preparation of 3-[(E)-3-(2naphthyl)-2-propen-1-yl]pyridine and 3-[(Z)-3-(2-naphthyl)-2-propen-1-yl]pyridine To a cooled (0° C.) solution of 1-(2-naphthyl)-3-(3-pyridyl)propan-1-ol (1.14 g) in CH₂Cl₂ (30 ml) were added triethylamine (2.5 ml), methanesulfonyl chloride (0.70 ml) and catalytic amount of 4-methylaminopyridine. The mixture was stirred at room temperature for 8 hours. The mixture was washed with water and brine, dried and concentrated. The residue was dissolved in 1,8-diazabicyclo [5.4.0]undec-7-ene (20 ml) and stirred at 90° C. for 1 hour. The reaction mixture was diluted with ethyl acetate, washed with water and brine, dried and concentrated. The residue was chromatographed on silica gel (hexane-ethyl acetate= 3:1) to give 3-[(E)-3-(2-naphthyl)-2-propen-1-yl]pyridine (123 mg) and 3-[(Z)-3-(2-naphthyl)-2-propen-1-yl]pyridine (67 mg). 3-[(E)-3-(2-naphthyl)-2-propen-1-yl]pyridine.

$^1$H-NMR (CDCl$_3$) δ: 3.61 (2H, d, J=6.4 Hz), 6.44 (1H, dt, J=6.4, 15.8 Hz), 6.63 (1H, d, J=15.8 Hz), 7.25 (1H,m), 7.42 (2H, m), 7.57 (2H, m), 7.76 (4H, m), 8.49 (1H, d, J=3.8 Hz), 8.55 (1H, br). 3-[(Z)-3-(2-naphthyl)-2-propen-1-yl]pyridine $^1$H-NMR (CDCl$_3$) δ: 3.74 (2H, d, J=4.8 Hz), 6.49 (2H, m), 7.22 (1H, m), 7.44 (3H, m), 7.68 (2H, m), 7.82 (3H, m), 8.44 (1H, dd, J=1.4, 4.8 Hz), 8.59 (1H, d, J=2.2 Hz).

EXAMPLE 5

Preparation of 3-[(E)-(5,6,7,8-tetrahydronaphthalen-2-yl)-2-propen-1-yl]pyridine and 3-[(Z)-(5,6,7,8-tetrahydronaphthalen-2-yl)-2-propen-1-yl]pyridine

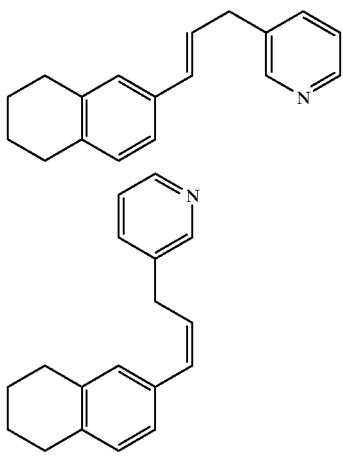

(i) Preparation of [(E)-2-(3-pyridyl)ethenyl]-(5,6,7,8-tetrahydronaphthalen-2-yl)ketone A 28% solution of sodium methoxide in MeOH (0.9 g) was added to a mixture of nicotinaldehyde (6.71 g) and 6-acetyltetraline (10.83 g) in MeOH (50 ml) and the mixture was stirred at room temperature for 12 hours. After removal of the solvent, the residue was diluted with ethyl acetate, washed with water and brine, dried and concentrated. The residue was chromatographed on silica gel (hexane-ethyl acetate =1:1) followed by recrystallization from hexane-ethyl acetate to give the titled compound (9.30 g).

$^1$H-NMR (CDCl$_3$) δ: 1.84 (4H, m), 2.85(4H,m), 7.20(1H, m), 7.37(1H, dd, J=5.0, 8.1 Hz), 7.60(1H, d, J=15.8 Hz), 7.77(3H, m), 7.96(1H, dt, J=1.9, 8.1 Hz), 8.63(1H, dd, J=1.9, 5.0 Hz), 8.87(1H, d, J=2.2 Hz).

(ii) Preparation of [2-(3-pyridyl)ethyl]-(5,6,7,8-tetrahydronaphthalen-2-yl)ketone A mixture of [(E)-2-(3-pyridyl)ethenyl]-(5,6,7,8-tetrahydronaphthalen-2-yl)ketone (6.32 g), palladium black (150 mg) and acetic acid (3 ml) in MeOH (50 ml) was stirred under hydrogen atmosphere at room temperature for 6 hours. The catalyst was filtered off and the filtrate was concentrated. The residue was dissolved in ethyl acetate, washed with saturated aqueous NaHCO$_3$ solution and brine, and dried. After removal of the solvent, the residue was recrystallized f rom hexane-ethyl acetate to give the titled compound (3.93 g).

$^1$H-NMR (CDCl$_3$) δ: 1.81(4H, m), 2.80(4H, m), 3.07(2H, t, J=7.1 Hz), 3.28(2H, t, J=7.1 Hz), 7.21(2H, m), 7.58(1H, m), 7.66(2H, m), 8.46(1H, dd, J=1.9, 4.8 Hz), 8.54(1H, d, J=1.9 Hz)

(iii) Preparation of 3-(3-pyridyl)-1-(5,6,7,8-tetrahydronaphthalen-2-yl)propanol To a solution of [2-(3-pyridyl)ethyl]-(5,6,7,8-tetrahydronaphthalen-2-yl)ketone (3.02 g) in MeOH (50 ml) was added NaBH$_4$ (0.45 g) and the mixture was stirred at room temperature for 30 minutes. After removal of the solvent, the residue was extracted with ethyl acetate. The extract was washed with water and brine, dried and concentrated to give the titled compound (1.56 g) as an oil.

$^1$H-NMR (CDCl$_3$) δ: 1.81 (4H, m), 2.07 (2H, m), 2.75 (6H, m), 4.59(1H, dd, J=5.4, 0 Hz), 7.05(3H, m), 7.19(1H, dd, J=6.8, 8.4 Hz), 7.51(1H, m), 8.39(2H, m).

(iv) Preparation of 3-[(E)-(5,6,7,8-tetrahydronaphthalen-2-yl)-2-propen-1-yl]pyridine and 3-[(Z)-(5,6,7,8-tetrahydronaphthalen-2-yl)-2propen-1-yl]pyridine To a cooled (0° C.) solution of 3-(3-pyridyl)-1-(5,6,7,8-tetrahydronaphthalen-2-yl)propanol (2.29 g) in CH$_2$Cl$_2$ (50 ml) were added triethylamine (2.4 ml) and methanesulfonyl chloride (0.86 ml ). The mixture was stirred at room temperature for 16 hours. The mixture was washed with water and brine, dried and concentrated. The residue was mixed with 1,8 -diazabicyclo[5.4.0]undec-7-ene (2.59 g) and stirred at 100° C. for 45 minutes. The reaction mixture was diluted with ethyl acetate, washed with water and brine, dried and concentrated. The residue was chromatographed on silica gel (hexane-ethyl acetate=3:1) to give 3-[(E)-(5,6,7,8-tetrahydronaphthalen-2-yl)-2-propen-1-yl]pyridine (216 mg) and 3-[(Z)-(5,6,7,8-tetrahydronaphthalen-2-yl)-2-propen-1-yl]pyridine (245 mg). 3-[(E)-(5,6,7,8-Tetrahydronaphthalen-2-yl)-2-propen-1-yl]pyridine $^1$H-NMR (CDCl$_3$) δ: 1.78(4H, m), 2.74(4H, m), 3.53(2H, d, J=6.4 Hz), 6.28(1H, dt, J=6.4, 16.0 Hz), 6.42(1H, d, J=16.0 Hz), 7.05(3H, m), 7.22(1H, m), 7.53(1H, m), 8.51 (2H, m). 3-[(Z)-(5,6,7,8-Tetrahydronaphthalen-2-yl)-2-propen-1-yl]pyridine $^1$H-NMR (CDCl$_3$) δ: 1.78(4H, m), 2.75(4H, m), 3.50(2H, d, J=4.8 Hz), 6.42(2H, m), 6.98(3H, m), 7.21(1H, m), 7.65(1H, dt, J=2.0, 7.6 Hz), 8.42(1H,d, J=3.6 Hz).

EXAMPLE 6

Preparation of 1-[(E)-5,6,7,8-tetrahydronaphthalene-2-yl)-2-butenyl-1H-imidazole

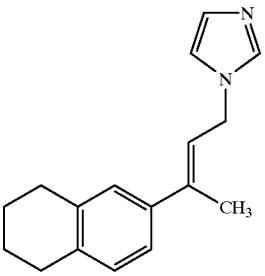

(i) Preparation of ethyl (E)-3-(5,6,7,8-tetrahydro-2-naphthyl)crotonate

NaH (60% oil dispersion, 5.10 g) was washed with hexane and was suspended in THF (150 ml). Ethyl diethylphosphonoacetate (28.31 g) was added to the suspension under ice cooling. 2-Acetyltetraline (20.39 g) was added to the mixture and stirred at room temperature for 14 hours. The reaction was quenched by the addition of water. The organic layer was washed with water and brine, dried and concentrated. The residue was purified by silica gel chromatography (hexane-ethyl acetate=40:1) to give the titled compound (7.12 g) as a colorless oil.

$^1$H-NMR (CDCl$_3$) δ: 1.32 (3H, t, J=7.2 Hz), 1.80 (4H, m), 2.56 (3H, d, J=1.4 Hz), 2.78 (4H, m), 4.21 (2H, q, J=7.2 Hz), 6.12 (1H, m), 7.07 (1H, d, J=7.6 Hz), 7.24 (2H, m).

(ii) Preparation of (E)-3-(5,6,7,8-tetrahydronaphthalen-2-yl)-2-buten-1-ol

A solution of diisobutylaluminum hydride in toluene (1.5M, 25 ml) was added dropwise to a solution of ethyl (E)-3-(5,6,7,8-tetrahydro-2-naphtyl)crotonate (3.72 g) in CH$_2$Cl$_2$ at −78° C. and the mixture was stirred at −78° C. for 15 minutes. The reaction mixture was washed with 1N HCl and brine, dried and concentrated to give the titled compound (2.65 g) as a colorless oil.

$^1$H-NMR (CDCl$_3$) δ: 1.78 (4H, m), 2.05 (3H, m), 2.76 (4H, m), 4.35 (2H, d, J=4.0 Hz), 5.94 (1H, m), 7.03 (1H, d, J=7.6 Hz), 7.16 (2H, m).

(iii) Preparation of 1-[(E)-3-(5,6,7,8-tetrahydronaphthalen-2-yl)-2-butenyl]-1H-imidazole Methanesulfonyl chloride (0.96 ml) was added to a mixture of ((E)-3-(5,6,7,8-tetrahydronaphthalen-2-yl)-2-buten-1-ol(1.97 g) and triethylamine (3.0 ml) in CH$_2$Cl$_2$ (40 ml) at 0° C. The mixture was stirred at room temperature for 8 hours, washed with water and brine, dried and concentrated. The residue was dissolved in DMF (20 ml) and cooled in ice bath. A mixture of NaH (60% oil dispersion, 0.427 g) and imidazole (0.814 g) in DMF (10 ml) was stirred for 10 minutes at room temperature, and was added to the solution. The resulting mixture was stirred for 30 minutes at 0° C. The reaction was quenched with water, the mixture was concentrated. The residue was extracted with ethyl acetate, washed with water and brine, dried and concentrated. Purification by silica gel chromatography (CH$_2$Cl$_2$—MeOH=9:1) gave the titled compound (0.465 g) as a colorless solid.

$^1$H-NMR (CDCl$_3$) δ: 1.80 (4H, m), 2.14 (3H, d, J=1.4 Hz), 2.76 (4H, m), 4.73 (2H, d, J=7.0 Hz), 5.86 (1H, m), 6.96 (1H, s), 7.10 (4H, m), 7.54 (1H, m).

Reference Example 1

Preparation of 1-(6-methoxy-2naphthyl)-1-ethanone n-BuLi (1.6M in hexane, 73 ml) was added dropwise to a solution of 2-bromo-6-methoxynaphthalene (25.29 g) at −78° C. and the mixture was stirred for 15 minutes. A solution of N-methoxy-N-methylacetamide (11.03 g) was added to the mixture and stirred for 1 hour at −78° C. 1N-HCl was added, and the whole was extracted with ethyl acetate. The extract was concentrated and crystallized from cyclohexane to give the titled compound (17.50 g) as a colorless powder.

$^1$H-NMR(CDCl$_3$) δ: 2.70 (3H, s), 3.95 (3H, s), 7.20 (2H, m), 7.77 (1H, d, J=8.7 Hz), 7.85 (1H, d, J=8.7 Hz), 8.02 (1H, dd, J=8.8, 1.8 Hz), 8.40 (1H, s).

IR (KBr): 1675, 1623, 1276, 1207, 859 cm$^{-1}$.

Reference Example 2

Preparation of ethyl (E)-3-(6-methoxy-2-naphthyl)crotonate

NaH (60% oil dispersion, 1.13 g) was washed with hexane and was suspended in THF (150 ml). Ethyl diethylphosphonoacetate (9.39 g) was added to the suspension under ice cooling. 1-(6-methoxy-2-naphthyl)-1-ethanone (7.23 g) was added to the mixture and stirred at room temperature for 12 hours. NaH(1.13 g) and ethyl diethylphosphonoacetate (9.39 g) were added to the mixture at 0° C. and the resulting mixture was stirred for 24 hours at room temperature. Water and ethyl acetate were added to the mixture, and the organic layer was washed with water and brine, dried and concentrated. The residue was purified by silica gel chromatography (hexane-ethyl acetate=30:1) followed by recrystallization from hexane to give titled compound (4.57 g) as a white solid $^1$H-NMR(CDCl$_3$) δ: 1.34 (3H, t, J=7.0 Hz), 2.68 (3H, d, J=1.3 Hz), 3.93 (3H, s), 4.24 (2H, q, J=7.0 Hz), 6.28 (H, d, J=1.3 Hz), 7.17 (2H, m), 7.58 (1H, dd, J=8.4, 1.8 Hz), 7.74 (2H, m), 7.89 (1H, d, J=1.8 Hz).

IR (KBr): 2960, 1712, 1621, 1253, 1158, 852 cm$^{-1}$.

Reference Example 3

Preparation of (E)-3-(6-methoxy-2-naphthyl)-2-buten-1-ol

A solution of diisobutylaluminum hydride in toluene (1.5M, 24 ml) was added dropwise to a solution of ethyl (E)-3-(6-methoxy-2-naphthyl) crotonate (4.0 g) in CH$_2$Cl$_2$ (50 ml) at −78° C. and the mixture was stirred at −78° C. for 30 minutes. The reaction mixture was washed with saturated aqueous solution of sodium potassium tartrate and brine, dried and concentrated. The residue was crystallized from CH$_2$Cl$_2$-hexane to give the titled compound (3.21 g) as a white solid.

$^1$H-NMR(CDCl$_3$) δ:2.17 (3H, s), 3.91 (3H, s), 4.40 (2H, m), 6.11 (1H, dt, J=1.4, 6.8 Hz), 7.13 (2H, m), 7.56 (1H, dd, J=2.0, 8.6 Hz), 7.70 (3H, m).

IR (KBr): 3251, 2964, 1463, 1029, 815 cm$^{-1}$.

EXAMPLE 7

Preparation of 1-[(E)-3-(6-methoxy-2-naphthyl)-2-buten-1-yl]-1H-imidazole

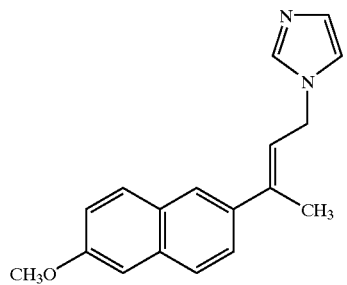

Methanesulfonyl chloride (1.2 ml) was added to a cooled (0° C.) mixture of (E)-3-(6-methoxy-2-naphthyl)-2-buten-1-ol (3.02 g), triethylamine (3.7 ml) in CH$_2$Cl$_2$ (60 ml). After being stirred at room temperature for 8 hours, the mixture was washed with water and brine, dried and concentrated. The residue was dissolved in DMF (20 ml) and cooled to 0° C., to which was added a mixture of imidazole (1.40 g)and NaH (60% oil dispersion, 0.81 g) in DMF (20 ml). The resulting mixture was stirred at 0° C. for 30 minutes. Water was added to the mixture and the whole was concentrated. The residue was diluted with ethyl acetate, washed with water and brine, dried and concentrated. The residue was chromatographed on silica gel (CH$_2$Cl$_2$—MeOH=9:1) followed by recrystallization from ethyl acetate to give the titled compound (0.687 g) as a colorless powder.

$^1$H-NMR(CDCl$_3$) δ: 2.27 (3H, s), 3.92 (3H, s), 4.79 (2H, d, J=7.0 Hz), 6.02 (1H, t, J=7.0 Hz), 6.96–7.20 (4H, m), 7.47–7.78 (5H, m).

IR (KBr): 2960, 1463, 1210, 1027, 854 cm$^{-1}$.

Reference Example 4

Preparation of ethyl (E)-3-(2-chloro-3-quinolinyl) acrylate

NaH (60% oil dispersion, 2.51 g) was washed with hexane and was suspended in THF (250 ml). Ethyl diethylphosphonoacetate (12.19 g) was added to the suspension at 0° C. 3-Chloroquinolincarboxaldehyde (10.12 g) was added to the mixture and stirred at room temperature for 14 hours. Water and ethyl acetate were added to the mixture, and the organic layer was washed with water and brine, dried and concentrated. The residue was purified by silica gel chromatography (hexane-ethyl acetate=10:1) followed by crystallization from hexane-MeOH to give the titled compound (9.89 g) as a white solid $^1$H-NMR(CDCl$_3$) δ: 1.38 (3H, t, J=7.1 Hz), 4.32 (2H, q, J=7.1 Hz), 6.57 (1H, d, J=15.9 Hz), 7.60 (1H, m), 7.81 (2H, m), 8.02 (1H, d, J=8.4 Hz), 8.09 (1H, d, J=15.9 Hz), 8.37 (1H, s).

IR (KBr): 1714, 1288, 1274, 1041 cm$^{-1}$.

Reference Example 5

Preparation of (E)-3-(2-chloro-3-quinolinyl)-2-propen-1-ol

A solution of diisobutylaluminum hydride in CH$_2$Cl$_2$ (1.0M, 85 ml) was added dropwise to a solution of ethyl (E)-3-(6-methoxy-2-naphthyl)acrylate (9.23 g)in CH$_2$Cl$_2$ (300 ml) at −78° C. and the mixture was stirred at −78° C. for 30 minutes. The reaction mixture was washed with saturated aqueous solution of sodium potassium tartrate and brine, dried and concentrated. The residue was crystallized from CH$_2$Cl$_2$-hexane to give the titled compound (6.12 g) as a white solid.

$^1$H-NMR(CDCl$_3$) δ: 1.84 (1H, t, J=5.9 Hz), 4.45 (2H, m), 6.49 (1H, dt, J=5.3, 15.7 Hz), 7.06 (1H, d, J=15.7 Hz), 7.55 (1H, m), 7.70 (1H, m), 7.76 (1H, d, J=8.0 Hz), 7.99 (1H, d, J=8.4 Hz), 8.24 (1H, s).

IR (KBr): 3255, 1650, 1585, 1486, 1095, 958 cm$^{-1}$.

Reference Example 6

Preparation of (E)-3-(2-methoxy-3-quinolinyl)-2-propen-1-ol

A mixture of (E)-3-(2-chloro-3-quinolinyl)-2-propen-1-ol (5.74 g) and sodium methoxide (28% in methanol; 10 ml) in MeOH (30 ml) was refluxed for 2 hours. The mixture was diluted with ethyl acetate, washed with water and brine, dried and concentrated. The residue was washed with cyclohexane-i-Pr$_2$O to give the titled compound (4.50 g; 80%) as a colorless solid.

$^1$H-NMR(CDCl$_3$) δ: 4.11 (3H, s), 4.37 (2H, m), 6.57 (1H, dt, J=5.5, 16.2 Hz), 6.89 (1H, d, J=16.2 Hz), 7.35 (1H, m), 7.58 (1H, m), 7.69 (1H, dd, J=1.0, 8.0 Hz), 7.82 (1H, d, J=8.0 Hz), 8.01 (1H, s).

IR (KBr): 3329, 1616, 1606, 1473, 1401, 1016 cm$^{-1}$.

EXAMPLE 8

Preparation of 1-[(E)-3-(2-methoxyquinoln-3-yl)-2-propen-1-yl]-1H-imidazole fumarate

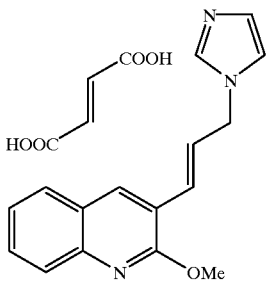

Methanesulfonyl chloride (3.9 ml) was added to a cooled (0° C.) mixture of (E)-3-(2-methoxy-3-quinolinyl)-2-propen-1-ol (4.39 g), triethylamine (5.7 ml) in CH$_2$Cl$_2$ (70 ml). After being stirred at room temperature for 8 hours, the mixture was washed with water and brine, dried and concentrated. The residue was dissolved in DMF (30 ml) and cooled to 0° C., to which was added a mixture of imidazole (1.44 g)and NaH (60% oil dispersion, 0.85 g) in DMF (20 ml). The resulting mixture was stirred at 0° C. for 30 minutes. Water was added to the mixture and the whole was concentrated. The residue was diluted with ethyl acetate, washed with water and brine, dried and concentrated. The residue was chromatographed on silica gel (CH$_2$Cl$_2$—MeOH=9:1) to give 1-[(E)-3-(2-methoxyquinoln-3-yl)-2-propen-1-yl]-1H-imidazole(2.42 g).

1-[(E)-3-(2-methoxyquinoln-3-yl)-2-propen-1-yl]-1H-imidazole (305 mg) was treated with fumaric acid (113 mg) to give the titled compound (294 mg; 67%) as a colorless powder.

$^1$H-NMR(DMSO-d$_6$) δ: 4.04 (3H, s), 4.87 (2H, d, J=5.2 Hz), 6.63 (2H, s), 6.72 (1H, m), 6.79 (1H, d, J=15.8 Hz), 6.98 (1H, s), 7.24 (1H, s), 7.41 (1H, t, J=7.3 Hz), 7.63 (1H, dt, J=1.6, 7.5 Hz), 7.80 (3H, m), 8.38 (1H, s).

R (KBr): 2950, 1700, 1473, 1446, 1264 cm$^{-1}$.

Reference Example 7

Preparation of ethyl (E)-3-(3-quinolinyl)acrylate

3-Quinolinecarbaldehyde (5.03 g) was added to a mixture of ethyl diethylphosphonoacetate (9.31 g) and NaH (60% oil dispersion,0.791 g) in THF under ice cooling. The mixture was stirred at room temperature for 14 hours. To the mixture were added water and ethyl acetate. The organic layer was washed with water and brine, dried and concentrated. The residue was chromatographed on silica gel (hexane-ethyl acetate=10:1) followed by crystallization from CH$_2$Cl$_2$-cyclohexane to give the titled compound (3.20 g) as a colorless solid.

$^1$H-NMR(CDCl$_3$) δ: 1.38 (3H, t, J=7.1 Hz), 4 .32 (2H, q, J=7.1 Hz), 6.68 (1H, d, J=16.2 Hz), 7.60 (1H, t, J=17.5 Hz), 7.77 (3H, m), 8.12 (1H, d, J=8.4 Hz), 8.25 (1H, d, J=2.2 Hz), 9.610 (H, d, J=2.2 Hz).

IR (KBr): 1706, 1635, 1185, 751 cm$^{-1}$.

Reference Example 8

Preparation of (E)-3-(3-quinolinyl)-2-propen-1-ol

A solution of diisobutylaluminum hydride in toluene (1.0M, 31 ml) was added dropwise to a solution of ethyl (E)-3-(3-quinolinyl)acrylate (2.94 g) in CH$_2$Cl$_2$ (50 ml) at −78° C. and the mixture was stirred at −78° C. for 30 minutes. The reaction mixture was washed with saturated aqueous solution of sodium potassium tartrate and brine, dried and concentrated. The residue was crystallized from CH$_2$Cl$_2$-ethyl acetate to give the titled compound (1.31 g) as a colorless solid.

$^1$H-NMR(CDCl$_3$) δ: 3.03 (3H, br), 4.40 (2H, d, J=74.6 Hz),, 6.75 (1H, dt, J=5.0, 16.1 Hz), 6.76 (1H, d, J=16.71 Hz), 7.52 (3H, t, J=7.3 Hz), 7.66 (1H, m), 7.76 (1H, d, J=8.0 Hz), 8.00 (1H, d, J=1.8 Hz), 8.07 (1H, d, J=8.4 Hz), 8.96 (1H, d, J=2.2 Hz).

IR (KBr): 3232, 1498, 1340, 1100, 782 cm$^{-1}$.

EXAMPLE 9

Preparation of 1-[(E)-3-(quinolyl)-2-propen-1-yl]-1H-imidazole

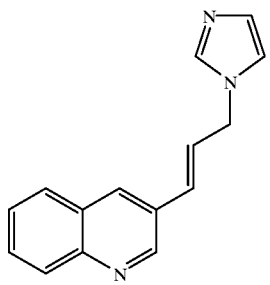

Methanesulfonyl chloride (0.65 ml) was added to a cooled (0° C.) mixture of (E)-3-(2-methoxy-3-quinolinyl)-2-propen-1-ol (1.20 g), triethylamine (1.8 ml) in CH$_2$Cl$_2$ (50 ml). After being stirred at room temperature for 8 hours, the mixture was washed with water and brine, dried and concentrated. The residue was dissolved in DMF (20 ml) and cooled to 0° C., to which was added a mixture of imidazole (0.493 g) and NaH (60% oil dispersion, 0.263 g) in DMF (20 ml). The resulting mixture was stirred at 0° C. for 30 minutes. Water was added to the mixture and the whole was concentrated. The residue was diluted with ethyl acetate, washed with water and brine, dried over and concentrated. The residue was chromatographed on silica gel (CH$_2$Cl$_2$—MeOH=9:1) followed by crystallization from ethyl acetate to give the titled compound (0.229 g) as a colorless solid.

$^1$H-NMR(CDCl$_3$) δ: 4.80 (2H, d, J=4.8 Hz), 6.50 (1H, m), 6.63 (1H, d, J=16.2 Hz), 7.01 (1H, s), 7.15 (1H, s), 7.55 (2H, m), 7.74 (2H, m), 8.05 (2H, m), 8.97 (1H, d, J=2.2 Hz).

IR (KBr): 3105, 1506, 1494, 1425, 1226, 807 cm$^{-1}$.

Reference Example 9

Preparation of ethyl (E)-3-(5,5,8,8,-tetramethyl-5,6,7,8-tetrahydronaphthalen-2-yl)crotonate 6-Acetyl-1,2,3,4-tetrahydro-1,1,4,4-tetramethylnaphthalene (5.07 g) was added to a cooled (0° C.) mixture of NaH (60% oil dispersion, 1.10 g) and ethyl diethylphosphonoacetate (6.49 g) in THF (50 ml). The mixture was stirred at room temperature for 14 hours. The reaction was quenched by the addition of water and the mixture was diluted with ethyl acetate. The organic layer was washed with water and brine, dried and concentrated to give the titled compound (6.50 g) as a colorless oil.

$^1$H-NMR (CDCl$_3$) δ: 1.14–1.40 (19H, m), 2.57 (3H, d, J=1.3 Hz), 4.22 (2H, q, J=7.2 Hz), 6.11 (1H, d, J=1.3 Hz), 7.24 (1H, dd, J=8.0, 1.6 Hz), 7.31 (1H, d, J=8.0 Hz), 7.41 (1H, d, J=1.6 Hz).

IR (KBr): 2961, 1715, 1626, 1165 cm$^{-1}$.

Reference Example 10

Preparation of (E)-3-(5,5,8,8-tetramethyl-5,6,7,8-tetrahydro-2-naphthalenyl)-2-buten-1-ol A solution of diisobutylaluminum hydride in toluene (1.5M, 50 ml) was added dropwise to a solution of ethyl (E)-3-(5,5,8,8,-tetramethyl-5,6,7,8-tetrahydronaphthalen-2-yl)crotonate (6.30 g) in THF (100 ml) at −78° C. and the mixture was stirred at −78 0° C. for 15 minutes. The mixture was washed with 1N HCl and brine, dried and concentrated. The residue was chromatographed on silica gel (hexane-ethyl acetate=10:1) to give the titled compound (4.33 g) as a colorless oil.

$^1$H-NMR (CDCl$_3$) δ: 1.20–1.35 (12H, m), 1.69 (4H, m), 2.08 (3H, d, J=0.8 Hz), 4.36 (2H, t, J=5.9 Hz), 5.96 (1H, m), 7.18 (1H, dd, J=2.0, 8.2 Hz), 7.27 (1H, d, J=8.2 Hz), 7.35 (1H, d, J=2.0 Hz).

IR (KBr): 3345. 2959, 1458, 1364 cm$^{-1}$.

EXAMPLE 10

Preparation of 1-[(E)-3-(5,5,8,8-tetramethyl-5,6,7,8-tetrahydro-2-naphthalenyl)-2-buten-1-yl]-1H-imidazole

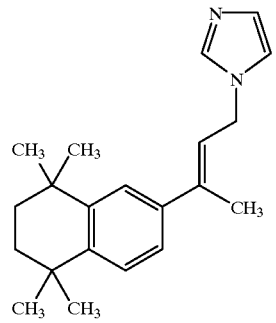

Methanesulfonyl chloride (3.6 ml) was added to a cooled (0° C.) mixture of (E)-3-(5,5,8,8-tetramethyl-5,6,7,8-tetrahydro-2-naphthalenyl)-2-buten-1-ol (4.03 g) and triethylamine (11 ml) in CH$_2$Cl$_2$ (20 ml). After being stirred at room temperature for 8 hours, the mixture was washed with water and brine, dried and concentrated. The residue was dissolved in DMF (20 ml) and cooled to 0° C. A mixture of imidazole (1.20 g) in DMF (1.20 g)and NaH (60% oil dispersion, 0.63 g) was added to the solution and the mixture was stirred at 0° C. for 30 minutes. After addition of water, the reaction mixture was concentrated and the residue was extracted with ethyl acetate. The extract was washed with water and brine, dried and concentrated. The residue was chromatographed on silica gel (CH$_2$Cl$_2$—MeOH=9:1) followed by recrystallization from ethyl acetate-hexane to give the titled compound (0.312 g) as a colorless solid.

$^1$H-NMR (CDCl$_3$) δ: 1.28 (6H, s), 1.29 (6H, s), 2.16 (3H, d, J=1.4 Hz), 4.74 (2H, d, J=7.0 Hz), 5.87 (1H, m), 6.96 (1H, t, J=1.4 Hz), 7.08 (1H, t, J=1.0 Hz), 7.17 (1H, dd, J=8.4, 2.0 Hz), 7.29 (1H, d, J=8.4 Hz), 7.32 (1H, d, J=2.0 Hz), 7.54 (1H, s).

IR (KBr): 2959, 1505, 1458, 1229 cm$^{-1}$.

Reference Example 11

Preparation of ethyl (E)-3-(6-methyl-2-naphthyl) crotonate

2-Acetyl-6-methylnaphthalene (5.08 g) was added to a cooled (0° C.) mixture of NaH (60% oil dispersion, 2.34 g)

in THF (150 ml) and ethyl diethylphosphonoacetate (14.12 g) and the mixture was stirred at room temperature for 14 hours. The reaction was quenched by the addition of water. The organic layer was washed with water and brine, dried and concentrated. Recrystallization of the residue from hexane gave the titled compound (3.25 g) as a colorless solid.

$^1$H-NMR (CDCl$_3$) δ: 1.34 (3H, t, J=7.1 Hz), 2.52 (3H, s), 2.68 (3H, d, J=2 Hz), 4.24 (2H, q, J=7.1 Hz), 6.28 (7H, m), 7.34 (1H, dd, J=1.6, 4.2 Hz), 7.58 (2H, m), 7.75 (2H, m), 7.91 (1H, m).

Reference Example 12

Preparation of (E)-3-(6-methyl-2-naphthyl)-2-buten-1-ol

A solution of diisobutylaluminum hydride in toluene (1.5M, 30 ml) was added dropwise to a solution of ethyl (E)-3-(6-methyl-2-naphthyl)crotonate (3.62 g) in THF (50 ml) at −78° C. and the mixture was stirred at −78° C. for 15 minutes. Saturated aqueous solution of NH$_4$Cl was added to the mixture and organic layer was washed with 1N HCl and brine, dried and concentrated. The residue was crystallized from hexane-cyclohexane gave the titled compound (2.54 g) as a colorless solid.

$^1$H-NMR (CDCl$_3$) δ: 2.18 (3H, s), 2.50 (3H, s), 4.42 (2H, d, J=6.7 Hz), 6.13 (H, dt, J=1.2, 6.7 Hz), 7.30 (1H, dd, J=8.4, 1.6 Hz), 7.56 (2H, m), 7.73 (3H, m).

IR (KBr): 3262, 2934, 1013, 889, 810 cm$^{-1}$.

EXAMPLE 11

Preparation of 1-[(E)-3-(6-methyl-2-naphthyl)-2-butenyl]-1H-imidazole

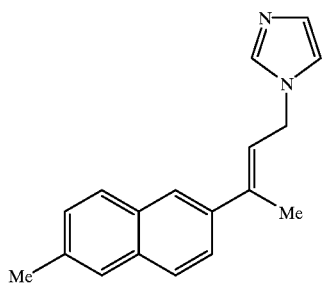

Methanesulfonyl chloride (1.8 ml) was added to a cooled (0° C.) mixture of (E)-3-(6-methyl-2-naphthyl)-2-buten-1-ol (2.45 g), triethylamine (4.8 ml) in THF (50 ml). After being stirred at room temperature for 8 hours, the mixture was washed with water and brine, dried and concentrated in vacuo. The residue was dissolved in DMF (20 ml) and cooled to 0° C. A mixture of imidazole (2.35 g) in DMF (20 ml) and NaH (60% oil dispersion, 1.43 g) was stirred at room temperature for 10 min, and added to the solution. The resulting mixture was stirred at 0° C. for 30 minutes. To the mixture was added water, and the whole was extracted with ethyl acetate. The extract was washed with water and brine, dried and concentrated. The residue was chromatographed on silica gel (CH$_2$Cl$_2$—MeOH=9:1) followed by recrystallization from CH$_2$Cl$_2$-cyclohexane to give the titled compound (0.651 g) as a colorless powder.

$^1$H-NMR (CDCl$_3$) δ: 2.27 (3H, s), 2.51 (3H, s), 4.79 (2H, d, J=7.0 Hz), 6.03 (1H, m), 6.99 (1H, s), 7.10 (1H, s), 7.32 (1H, dd, J=8.4, 1.6 Hz), 7.50 (1H, dd, J=8.4, 1.8 Hz), 7.57 (2H, m), 7.64–7.82 (3H, m)

IR (KBr): 1507, 1233, 885, 818 cm$^{-1}$.

Reference Example 13

Preparation of (E)-1-(2-naphthyl)-3-(1-trithyl-1H-imidazol-4-yl)-2-propen-1-one

A mixture of 2-acetylnaphthalene (0.55 g), 1-trithyl-4-formyl-1H-imidazole (1.02 g) and NaOH (0.30 g) in ethanol (50 ml) was stirred for 1 hour. Crystals were collected, washed with ethanol to give the titled compound (1.21 g) as a colorless solid.

$^1$H-NMR(CDCl$_3$) δ: 7.10–7.23 (7H, m), 7.30–7.43 (9H, m), 7.50–7.65 (3H, m), 7.73 (1H, d, J=15.2 Hz), 7.84–8.03 (4H, m), 8.15 (1H, dd, J=1.8, 8.6 Hz), 8.63 (1H, s).

IR (KBr): 1659, 1603, 1283, 1121, 702 cm$^{-1}$.

Reference Example 14

Preparation of 1-(2-naphthyl)-3-(1-trithyl-1H-imidazol-4-yl)propan-1-one

A mixture of (E)-1-(2-naphthyl)-3-(1-trithyl-1H-imidazol-4-yl)-2-propen-1-one (1.13 g) and palladium carbon (0.450 g) in ethyl acetate (30 ml) was stirred under hydrogen atmosphere for 6 hours. The catalyst was filtered off and the filtrate was concentrated in vacuo. The residue was chromatographed on silica gel (hexane:AcOEt=1:1) to give the titled compound (0.48 g) as a colorless solid.

$^1$H-NMR(CDCl$_3$) δ: 3.04 (2H, t, J=7.4 Hz), 3.50 (2H, t, J=7.4 Hz), 6.59 (1H, m), 7.04–7.14 (6H, m), 7.20–7.38 (10H, m), 7.48–7.64 (2H, m), 7.82–8.07 (4H, m), 8.49 (1H, s).

IR (KBr): 3059, 1680, 1445, 1184, 1123 cm$^{-1}$.

Reference Example 15

Preparation of 1-(2-naphthyl)-3-(1-trithyl-1H-imidazol-4-yl)propan-1-ol

To a solution of 1-(2-naphthyl)-3-(1-trithyl-1H-imidazol-4-yl)propan-1-one (0.435 g) in MeOH (50 ml) was added NaBH$_4$ (0.12 g) and the mixture was stirred at room temperature for 30 minutes.

After removal of the solvent, the residue was extracted with ethyl acetate. The extract was washed with water and brine, dried and concentrated to give the titled compound (0.40 g) as a white solid.

$^1$H-NMR(CDCl$_3$) δ: 2.16 (2H, m), 2.71 (2H, t, J=6.5 Hz), 4.99 (1H, t, J=5.9 Hz), 6.54 (1H, s), 7.06–7.20 (6H, m), 7.26–7.54 (14H, m), 7.75–7.88 (4H, m).

IR (KBr): 3056, 1493, 1447, 748, 702 cm$^{-1}$.

EXAMPLE 12

Preparation of 4-[(E)-3-(2-naphthyl)-2-propen-1-yl]-1H-imidazole

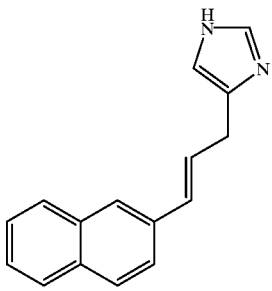

To a solution of 1-(2-naphthyl)-3-(1-trithyl-1H-imidazol-4-yl)propan-1-ol (0.391 g) in dimethoxyethane (40 ml) was added p-toluenesulfonic acid (0.51 g) and the mixture was refluxed for 15 hours. After removal of the solvent the residue was extracted with ethyl acetate. The extract was washed with aqueous saturated $NaHCO_3$ solution, water and brine, dried and concentrated. The residue was chromatographed on silica gel (ethyl acetate:MeOH:aq.$NH_3$=9:1:0.3) followed by washing with hexane-ethyl acetate to give the titled compound (0.116 g) as colorless solid.

$^1$H-NMR($CDCl_3$) δ: 3.60 (2H, d, J=6.3 Hz), 6.48 (1H, dt, J=6.3, 15.6 Hz), 6.65 (1H, d, J=15.6 Hz), 6.87 (1H, d, J=0.8 Hz), 7.36–7.50 (2H, m), 7.53–7.64 (2H, m), 7.68 (1H, s), 7.71–7.84 (3H, m).

IR (KBr): 3056, 1449, 968, 820, 745 cm$^{-1}$.

EXAMPLE 13

Preparation of 1-[(E)-3-(2-naphthyl)-2-propenyl]-1H-1,2,4-triazole

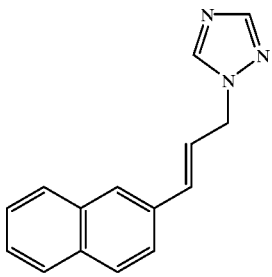

A mixture of (E)-1-chloro-3-(2-naphthyl)-2-propene (0.5 g), 1H-1,2,4-triazole (0.5 g) and $K_2CO_3$ (1.0 g) in DMF (20 ml) was stirred for 14 hours. The mixture was diluted with ethyl acetate and insolubles were filtered off. The filtrate was concentrated in vacuo and the residue was chromatographed on silica gel, eluting with ethyl acetate to give the titled compound (0.06 g) as colorless powder.

$^1$H-NMR($CDCl_3$) δ: 5.02 (2H, d, J=6.6 Hz), 6.47 (1H, dt, J=15.8 Hz, 6.6 Hz), 6.81 (1H, d, J=15.8 Hz), 7.42–7.55 (2H, m), 7.58 (1H, dd, J=8.4 Hz, 1.8 Hz), 7.70–7.90 (3H, m), 8.02 (1H, s), 8.20 (1H, d, J=5.6 Hz), 8.22 (1H, s).

IR (KBr): 3109, 1595, 1504, 1271 cm$^{-1}$.

Reference Example 16

Preparation of ethyl (Z)-2-fluoro-3-(2-naphthyl)acrylate

To a cooled (0° C.) solution of 2-hydroxymethylnaphthalene (5.19 g) in THF (50 ml) were added triethylamine (9.1 ml) and methanesulfonyl chloride (3.1 ml) successively. The mixture was stirred at room temperature for 1 hour, then washed with water and brine, dried and concentrated. The residue was dissolved in DMF (30 ml) and cooled to 0° C. To this mixture was added a mixture of ethyl 2-fluoro-2-(phenylsulfinyl)acetate (7.74 g) prepared by a manner shown in T. Allmendinger, Tetrahedron, 1991, Vol 47, 4905 and 60% NaH (1.69 g) in DMF (30 ml) and the resulting mixture was stirred at room temperature for 30 minutes and then at 95° C. for 1 hour. To the mixture was added water and the mixture was concentrated. The residue was extracted with ethyl acetate. The extract was washed with $H_2O$ and brine, dried and concentrated. The residue was chromatographed on silica gel (hexane:AcOEt=20:1) to give the titled compound (3.87 g) as a colorless solid.

$^1$H-NMR ($CDCl_3$) δ: 1.41 (3H, t, J=7.1 Hz), 4.48 (2H, q, J=7.1 Hz), 7.07 (1H, d, J=35 Hz), 7.46–7.60 (2H, m), 7.74–7.94 (4H, m), 8.10 (1H, s).

IR (KBr): 2984, 1728, 1661, 1254, 1100, 747 cm$^{-1}$.

Reference Example 17

Preparation of (Z)-2-fluoro-3-(2-naphthyl)-2-propen-1-ol

The reaction of ethyl (Z)-2-fluoro-3-(2-naphthyl)acrylate (3.77 g) with diisobutylaluminum hydride was carried out in a similar manner as described in Reference example 3 to give the titled compound (2.77 g) as a colorless solid.

$^1$H-NMR ($CDCl_3$) δ: 4.34 (2H, dd, J=6.4, 14.4 Hz), 5.95 (1H, d, J=39 Hz), 7.36–7.54 (2H, m), 7.62–7.87 (4H, m), 7.93 (1H, s).

IR (KBr): 3314, 1771, 1246, 1165, 1019, 909, 741 cm$^{-1}$.

EXAMPLE 14

Preparation of 1-[(Z)-2-fluoro-3-(2-naphthyl)-2-propenyl]-1H-imidazole

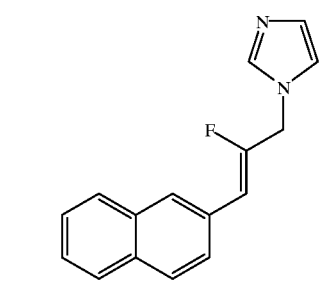

(Z)-2-Fluoro-3-(2-naphthyl)-2-propen-1-ol (2.02 g) was converted to the titled compound (1.68 g) in a manner similar to that described in Example 7.

$^1$H-NMR ($CDCl_3$) δ: 4.81 (2H, d, J=14.2 Hz), 7.85 (2H, d, J=38 Hz), 7.07 (1H, s), 7.15 (1H, s), 7.48 (2H, m), 7.63 (2H, m), 7.75–7.86 (3H, m), 7.90 (3H, m).

IR (KBr) 3092, 1690, 1505, 1233, 1154, 905, 824 cm$^{-1}$.

Reference Example 18

Preparation of 3-(2-naphthyl)-2-propyn-1-ol

A mixture of 2-bromonaphthalene (19.83 g), CuI (1.59 g), 2-propyn-1-ol (10 ml) and dichlorobis(triphenylphosphine)palladium (II) (2.00 g) in triethylamine (300 ml) was stirred under argon atmosphere at 50° C. for 72 hours. The catalyst was filtered off and the filtrate was concentrated in vacuo. The residue was extracted with ethyl acetate and the extract was washed with water and brine, dried over $Na_2SO_4$ and concentrated in vacuo. The residue was chromatographed on silica gel (hexane:ethyl acetate=5:2) followed by recrystallization from hexane-ethyl acetate to give the titled compound (14.92 g) as a colorless powder.

$^1$H-NMR (CDCl$_3$) δ: 1.74 (1H, t, J=6.2 Hz), 4.56 (2H, d, J=6.2 Hz), 7.50 (3H, m), 7.80 (3H, m), 7.97 (1H, s).

IR (KBr):3308, 1593, 1036, 821, 741 cm$^{-1}$.

EXAMPLE 15

Preparation of 1-[3-(2-naphthyl)-2-propynyl]-1H-imidazole

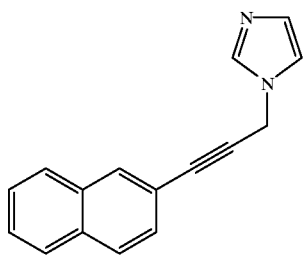

To a cooled (0° C.) solution of 3-(2-naphthyl)-2-propyn-1-ol (2.67 g) in THF (100 ml) were added triethylamine (4.1 ml) and methanesulfonyl chloride (1.7 ml) successively. The mixture was stirred at room temperature for 1 hours. Imidazole (3.02 g) and NaI (0.5 g) were added to the mixture and resulting mixture was stirred at 60° C. for 3 hours. To the mixture was added water, and the mixture was concentrated. The residue was extracted with ethyl acetate. The extract was washed with water and brine, dried and concentrated. The residue was chromatographed on silica gel, eluting with ethyl acetate, followed by crystallization from cyclohexane to give the titled compound (1.05 g) as a colorless solid.

$^1$H-NMR (CDCl$_3$) δ: 5.01 (2H, s), 7.14 (2H, m), 7.43–7.56 (3H, m), 7.70 (1H, s), 7.76–7.87 (3H, m), 7.98 (1H, s).

IR (KBr): 3102, 1597, 1505, 1281, 1073, 862 cm$^{-1}$.

Reference Example 19

Preparation of 4-hydroxy-1-(2-naphthyl)-1-butanone

To a cooled (−78° C.) solution of 2-bromonaphthalene (10.77 g) in THF (150 ml) was added n-BuLi in hexane (1.65M, 36 ml) and the mixture was stirred at −78° C. for 30 minutes. To the solution was added γ-butyrolactone (25 ml) and the mixture was stirred at −78° C. for 1 minute. Aqueous solution of NH$_4$Cl was added and the mixture was extracted with ethyl acetate. The extract was washed with aqueous NH$_4$Cl solution, water and brine, dried and concentrated. The residue was chromatographed on silica gel (hexane:ethyl acetate=3:1) followed by recrystallization from cyclohexane-ethyl acetate to give the titled compound (6.71 g) as a colorless solid.

$^1$H-NMR (CDCl$_3$) δ: 2.09 (2H, m), 3.28 (2H, t, J=6.9 Hz), 3.80 (2H, q, J=5.7 Hz), 7.50–7.63 (2H, m), 7.85–8.10 (4H, m), 8.51 (1H, s).

IR (KBr): 3349, 1680, 1372, 1184, 1059 cm$^{-1}$.

Reference Example 20

Preparation of 4-(1H-imidazol-1-yl)-1-(2-naphthyl)-1-butanone

To a cooled (0° C.) solution of 4-hydroxy-1-(2-naphthyl)-1-butanone (4.32 g) in THF (60 ml) were added triethylamine (5.6 ml) and methanesulfonyl chloride (2.4 ml) successively. The mixture was stirred at 0° for 1 hour. Imidazole (2.93 g) and NaI (0.02 g) were added to the mixture and resulting mixture was refluxed for 16 hours. Water was added and the mixture was concentrated. The residue was extracted with ethyl acetate and the extract was washed with water and brine, dried and concentrated. The residue was chromatographed on silica gel, eluting with ethyl acetate-methanol=20:1, followed by crystallization from ethyl acetate-CH$_2$Cl$_2$-cyclohexane to give the titled compound (1.21 g) as a colorless solid.

$^1$H-NMR (CDCl$_3$) δ: 2.30 (2H, quint, J=7.0 Hz), 3.08 (2H, t, J=7.0 Hz), 4.13 (2H, t, J=7.0 Hz), 6.96 (1H, s), 7.09 (1H, s), 7.48–7.70 (3H, m), 7.84–8.03 (4H, m), 8.40 (1H, s).

IR (KBr): 3110, 1680, 1508, 1229, 823 cm$^{-1}$.

Reference Example 21

Preparation of 4-(1H-imidazol-1-yl)-1-(2-naphthyl)-1-butanol

To a solution of 4-(1H-imidazol-1-yl)-1-(2-naphthyl)-1-butanone (0.793 g) in MeOH (5 ml) was added NaBH$_4$ (0.213 g) and the mixture was stirred at room temperature for 2 hours. Water was added and the whole was concentrated. The residue was extracted with ethyl acetate. The extract was washed with water and brine, dried and concentrated. The residue was chromatographed on silica gel (ethyl acetate-MeOH=20:1) followed by crystallization to give the titled compound (0.615 g) as a colorless solid.

$^1$H-NMR (CDCl$_3$) δ: 1.60–2.08 (4H, m), 3.94 (2H, t, J=6.4 Hz), 4.86 (1H, t, J=5.7 Hz), 6.86 (1H, s), 7.01 (1H, s), 7.37–7.54 (4H, m), 7.74–7.88 (4H, m).

IR (KBr) 3112, 1508, 1231, 1080, 822 cm$^{-1}$.

EXAMPLE 16

Preparation of 1-[(E)-4-(2-naphthyl)-3-buten-1-yl]-1H-imidazole

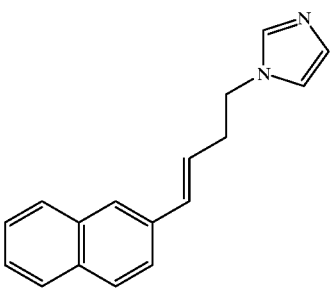

A mixture of 4-(1H-imidazol-1-yl)-1-(2-naphthyl)-1-butanol (0.450 g) and p-toluenesulfonic acid hydrate (0.589 g) in dimethoxyethane (20 ml) was refluxed for 16 hours. To the mixture was added water, then the whole was concentrated and extracted with ethyl acetate. The extract was washed with water and brine, dried and concentrated. The residue was chromatographed on silica gel (ethyl acetate-MeOH=20:1) followed by crystallization from ethyl acetate-hexane to give the titled compound (0.112 g) as a colorless powder.

¹H-NMR (CDCl₃) δ: 2.73 (2H, q, J=7.0 Hz), 4.11 (2H, t, J=7.0 Hz), 6.21 (1H, dt, J=16.0, 7.0 Hz), 6.58 (1H, d, J=16.0 Hz), 6.97 (1H, s), 7.08 (1H, s), 7.36–7.58 (4H, m), 7.65 (1H, s), 7.72–7.84 (3H, m).

IR (KBr): 3110, 1507, 1231, 966, 814, 745 cm⁻¹.

Reference Example 22

Preparation of 2-formyl-6-methoxynaphthalene n-BuLi in hexane (1.59M, 125 ml) was added dropwise to a solution of 2-bromo-6-methoxynaphthalene (42.27 g) in THF (600 ml) at −78° C. and was stirred at −78+ C. for 30 minutes. To the mixture was added DMF (28 ml), and the whole was allowed to warm to room temperature. The reaction mixture was acidified with HCl and extracted with ethyl acetate. The extract was dried and concentrated to give the titled compound (32.31 g) as a colorless solid.

¹H-NMR (CDCl₃) δ: 3.96 (3H, s), 7.15–7.30 (2H,m), 7.75–7.97(3H,m), 8.26 (1H,s), 10.10 (1H,s).

IR (KBr): 2841, 1688, 1624, 1480, 1269, 1028, 856 cm⁻¹.

Reference Example 23

Preparation of ethyl (E)-3-(6-methoxy-2-naphthyl) acrylate

2-Formyl-6-methoxynaphthalene (15.51 g) was treated in a manner similar to that described in Reference example 2 to give the titled compound (20.98 g) as a colorless solid.

¹H-NMR (CDCl₃) δ: 1.36 (3H, t, J=7.1 Hz), 3.93 (3H, s), 4.28 (2H, q, J=7.1 Hz), 6.50 (11H, d, J=16.0 Hz), 7.10–7.21 (2H, m), 7.58–7.89 (5H, m).

IR (KBr): 2980, 1703, 1626, 1308, 1175 cm⁻¹.

Reference Example 24

Preparation of (E)-3-(6-methoxy-2-naphthyl)-2-propen-1-ol

Ethyl (E)-3-(6-methoxy-2-naphthyl)acrylate (19.96 g) was treated in the manner as described in Reference example 3 to afford the titled compound (13.79 g) as a colorless powder.

¹H-NMR (CDCl₃) δ: 3.92 (3H, s), 4.36 (2H, t, J=4.8 Hz). 6.43 (1H, dt, J=15.8, 5.8 Hz), 6.74 (1H, d, J=15.8 Hz), 7.06–7.18 (2H, m), 7.51—7.73 (4H, m).

IR (KBr): 3293, 1626, 1601, 1483, 1242, 1032, 972 cm⁻¹.

EXAMPLE 17

Preparation of 1-[(E)-3-(6-methoxy-2-naphthyl)-2-propenyl]-1H-imidazole

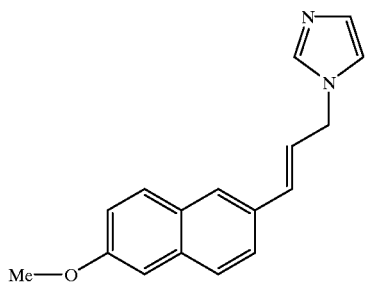

To a cooled (0° C.) solution of (E)-3-(6-methoxynaphthalen-2-y)-2-propen-1-ol (3.09 g), in THF (50 ml) was added thionyl chloride (2.1 ml) and the mixture was refluxed for 2 hours. After cooling, the mixture was concentrated in vacuo and the residue was dissolved in ethyl acetate. The solution was washed with water and brine, dried and concentrated. The residue was dissolved in DMF (30 ml) and cooled to 0° C. A mixture of imidazole (2.29 g) in DMF (20 ml) and NaH (60% oil dispersion, 0.98 g) was stirred at room temperature for 10 min, then added to the solution. The resulting mixture was stirred at 0° C. for 30 minutes and water was added. After removal of the solvent, the residue was extracted with ethyl acetate. The extract was washed with water and brine, dried and concentrated. The residue was chromatographed on silica gel (CH₂Cl₂—MeOH=9:1) followed by recrystallization from ethyl acetate-hexane to give the titled compound (2.29 g) as a colorless solid.

¹H-NMR (CDCl₃) δ: 3.92 (3H, s), 4.75 (2H, dd, J=1.4, 6.2 Hz), 6.34 (1H, dt, J=15.8, 6.2 Hz), 6.65 (1H, d, J=15.8 Hz), 7.00 (1H, s), 7.06–7.18 (3H, m), 7.47–7.61 (2H, m), 7.62–7.74 (3H, m).

IR (KBr): 3113, 1630, 1601, 1505, 1483, 1242, 1028, 855 cm⁻¹.

Reference Example 25

Preparation of ethyl (E)-3-(benzofuran-2-yl) crotonate

Benzofuran-2-yl methyl ketone (9.59 g) was converted to the titled compound (6.43 g, colorless solid) in a manner similar to that described in Reference Example 3.

¹H-NMR (CDCl₃) δ: 1.33 (3H, t, J=7.1 Hz), 2.55 (3H, d, J=1.4 Hz), 4.24 (2H,q, J=7.1 Hz), 6.65 (1H, m), 7.00 (1H, s), 7.30 (2H, m), 7.46 (1H, d, J=8.2 Hz), 7.58 (1H, m).

IR (KBr): 1704, 1623, 1448, 1166 cm⁻¹.

Reference Example 26

Preparation of (E)-3-(benzofuran-2-yl)-2-buten-1-ol

Ethyl (E)-3-(benzofuran-2-yl)crotonate (5.10 g) was converted to the titled compound (3.78 g, colorless solid) in a manner similar to that described in Reference Example 3.

¹H-NMR (CDCl₃) δ: 2.06 (3H, s), 4.42 (2H, m), 6.54 (1H, t, J=6.8 Hz), 6.65 (1H, s), 7.23 (2H, m), 7.48 (2H, m).

IR (KBr): 3234, 1556, 1452, 1259, 994 cm⁻¹.

EXAMPLE 18

Preparation of (E)-3-(benzofuran-2-yl)-2-buten-1-ol

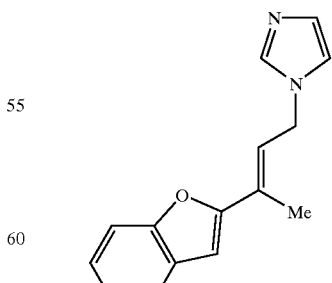

(E)-3-(benzofuran-2-yl)-2-buten-1-o (3.13 g) was converted to the titled compound (0.41 g, colorless solid) in a manner similar to that described in Example 7.

$^1$H-NMR (CDCl$_3$) δ: 2.15 (3H, s), 4.80 (2H, d, J=7.1 Hz), 6.48 (1H, t, J=7.1 Hz), 6.72 (1H, s), 6.99 (1H, s), 7.11 (1H, s), 7.16–7.33 (2H, m), 7.42 (1H, d, J=8.2 Hz), 7.54 (2H, m).

IR (KBr): 1554, 1450, 1239, 1168 cm$^{-1}$.

Reference Example 27

Preparation of 2-ethoxycarbonylbenzofurane

A mixture of salicylaldehyde (53.10 g), K$_2$CO$_3$ (97 g) and ethyl bromoacetate (73.30 g) in ethanol (200 ml) was refluxed for 6 hours. The reaction mixture was diluted with ethyl acetate, washed with water, 1N NaOH and brine, dried and concentrated to give the titled compound (27.40 g) as a colorless oil $^1$H-NMR (CDCl$_3$) δ: 1.43 (3H, t, J=7.1 Hz), 4.45 (2H, q, J=7.1 Hz), 7.20–7.73 (5H, m).

IR (KBr): 2982, 1732, 1574, 1298, 1182, 750 cm$^{-1}$.

Reference Example 28

Preparation of 2-hydroxymethylbenzofuran

The reaction of 2-ethoxycarbonylbenzofurane (27.40 g) with diisobutylaluminum hydride was carried out in the manner similar to that described in Reference Example 3 to give the titled compound (16.91 g) as a colorless oil. This compound was used without further purification.

$^1$H-NMR(CDCl$_3$) δ: 4.76 (2H, s), 6.65 (1H, s), 7.15–7.34 (2H, m), 7.40–7.63 (2H, m).

IR(KBr): 3299, 1605, 1454, 1254, 1009, 752 cm$^{-1}$.

Reference Example 29

Preparation of 2-formylbenzofuran

A mixture of 2-hydroxymethylbenzofuran (6.91 g) and MnO$_2$ (37.4 g) in CH$_2$Cl$_2$ (250 ml) was stirred at 30° C. for 3 days. Insoluble materials were filtered off and the filtrate was concentrated to give the titled compound (5.01 g) as colorless oil.

$^1$H-NMR (CDCl$_3$) δ: 7.35 (1H, dt, J=1.4, 7.4 Hz), 7.48–7.66 (3H, m), 7.76 (1H, dd, J=1.2, 8.0 Hz), 9.88 (1H, s).

IR (KBr): 1682, 1611, 1557, 1289, 1121, 833 cm$^{-1}$.

Reference Example 30

Preparation of ethyl (E)-3-(1-benzofuran-2-yl)acrylate

2-Formylbenzofuran (5.45 g) was converted to the titled compound (5.06 g, colorless solid) in the manner similar to that described in Reference Example 2.

$^1$H-NMR (CDCl$_3$) δ: 1.35 (3H, t, J=7.1 Hz), 4.28 (2H, q, J=7.1 Hz), 6.58 (1H, d, J=15.7 Hz), 6.93 (1H, s), 7.24 (1H, dt, J=1.4, 6.8 Hz), 7.36 (1H, dt, J=1.4, 7.6 Hz), 7.46 (1H, m), 7.55 (1H, d, J=15.7 Hz), 7.59 (1H, m).

IR (KBr): 2982, 1713, 1638, 1451, 1264, 1173 cm$^{-1}$.

Reference Example 31

Preparation of (E)-3-(1-benzofuran-2-yl)-2-propen-1-ol

Ethyl (E)-3-(1-benzofuran-2-yl)acrylate (4.37 g) was converted to the titled compound (3.06 g, colorless solid) in the manner similar to that described in Reference Example 3.

$^1$H-NMR (CDCl$_3$) δ: 4.38 (2H, d, J=2.2 Hz), 6.59 (3H, m), 7.14–7.32 (2H, m), 7.40–7.55 (2H, m).

IR (KBr): 3335, 1678, 1557, 1453, 1254, 955, 748 cm$^{-1}$.

EXAMPLE 19

Preparation of 1-[(E)-3-(1-benzofuran-2-yl)-2-propenyl]-1H-imidazole fumarate

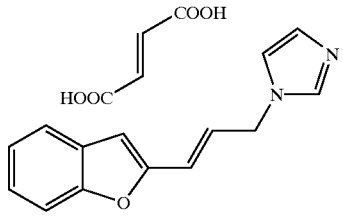

(E)-3-(1-Benzofuran-2-yl)-2-propen-1-ol (1.46 g) was converted to the titled compound (0.40 g, colorless solid) in a manner similar to that described in Example 8.

$^1$H-NMR (DMSO-d$_6$) δ: 4.86 (2H, d, J=4.4 Hz), 6.51 (2H, m), 6.63 (2H, s), 6.90 (1H, s), 6.99 (1H, m), 7.16–7.36 (3H, m), 7.46–7.64 (2H, m), 7.77 (1H, s).

IR (KBr): 3086, 1698, 1451, 1254, 1184, 754 cm$^{-1}$.

Reference Example 32

Preparation of 5-chlorobenzo[b]thiophene-2-carboxaldehyde

To a solution of 5-chlorobenzo[b]thiophene (6.14 g) in THF (120 ml) was added n-BuLi (1.6 M solution in hexane, 27.3 ml) at −78° C., and the mixture was stirred for 2 hours. To this mixture was added DMF (8.5 ml), and the mixture was stirred for 1 hour at −78° C. to −30° C. The reaction was quenched by the addition of water and allowed to warm to room temperature. The organic layer was separated, diluted with ethyl acetate, washed with 10% citric acid solution, brine, dried over MgSO$_4$, and concentrated. The residue was titurated with diisopropylether to give the titled compound as colorless crystals (5.92 g).

$^1$H-NMR (CDCl$_3$) δ: 7.48 (1dd, J=8.8, 2.0 Hz), 7.84 (1H, d, J=8.8 Hz), 7.94 (1H, d, J=2.0 Hz), 7.97 (1H, s), 10.12 (1H, s).

IR (KBr): 1678, 1516, 1140 cm$^{-1}$.

Reference Example 33

Preparation of ethyl 3-(5-chlorobenzo[b]thiophen-2-yl)acrylate

The titled compound (8.00 g) was prepared as colorless crystals from the compound obtained in Reference Example 32 (5.70 g) by the similar reaction and purification procedure as described in Reference Example 2.

$^1$H-NMR (CDCl$_3$) δ: 1.35 (3H, t, J=7.0 Hz), 4.28 (2H, q, J=7.0 Hz), 6.31 (1H, d, J=15.6 Hz), 7.33 (1H, dd, J=8.6, 2.0 Hz), 7.39 (1H, s), 7.70 (1H, d, J=8.6 Hz), 7.74 (1H, d,=2.0 Hz), 7.84 (1H, d, J=15.6 Hz).

IR (KBr):1711, 1630, 1319, 1173, 1152, 957, 795 cm$^{-1}$.

Reference Example 34

Preparation of (E)-3-(5-chlorobenzo[b]thiophen-2-yl)-2-propen-1-ol

The titled compound (5.54 g) was prepared as colorless crystals from the compound obtained in Reference Example 33 (7.90 g) by the similar reaction and purification procedure as described in Reference Example 3.

$^1$H-NMR (CDCl$_3$) δ: 4.33–4.38 (2H, brm), 6.30 (2H, dt, J=15.6, 5.4 Hz), 6.85 (1H, d, J=15.6 Hz), 7.08 (1H, s), 7.25 (1H, dd, J=8.6, 2.2 Hz), 7.65 (H, d, J=8.6 Hz), 7.65 (H, d, J=2.2 Hz).

IR (KBr): 3293, 1078, 1009, 806 cm$^1$.

EXAMPLE 20

Preparation of 1-[(E)-3-(5-chlorobenzo[b]thiophen-2-yl)-2-propen-1-yl]-1H-imidazole

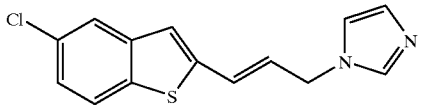

To a solution of the compound obtained in Reference Example 34 (4.73 g) in THF (60 ml) was added thionyl chloride (3.14 ml) at 0° C. The mixture was stirred at room temperature for 4 hours and concentrated. The residue was titurated with hexane and collected by filtration to give 5-chloro-2-(3-chloro-(E)-1-propen-1-yl)benzo[b]thiophene (4.70 g). This compound (4.48 g) was stirred with 1H-imidazole (4.43 g) in DMF (45 ml) at 50° C. for 9 hours. The mixture was diluted with water and extracted with ethyl acetate. The extract was washed with water and brine, dried over MgSO$_4$, and concentrated. The residue was chromatographed on silica gel using ethyl acetate-EtOH (10:1) as an eluent to give the titled compound as colorless crystals (3.73 g).

$^1$H-NMR (CDCl$_3$) δ: 4.74 (2H, d, J=5.8 Hz), 6.23 (1H, dt, J=15.8, 5.8 Hz), 6.65 (1H, d, J=15.8 Hz), 6.98 (1H, s), 7.09 (1H, s), 7.13 (1H, s), 7.27 (1H, dd, J=8.8, 2.0 Hz), 7.56 (1H, s), 7.66 (1H, d, J=8.8 Hz), 7.67 (1H, d, J=2.0 Hz).

IR (KBr): 3090, 1431, 1074, 949, 866, 843, 812, 756 cm$^{-1}$.

Reference Example 35

Preparation of 3-chloro-1-(5-fluoro-3-methylbenzo[b]thiophen-2-yl)propan-1-one

To a mixture of 5-fluoro-3-methylbenzo[b]thiophene (9.97 g) and 3-chloropropionyl chloride (7.45 ml) in carbon disulfide (100 ml) was added AlCl$_3$ (16.00 g) at 0° C. The mixture was stirred at room temperature for 2 hours, poured onto crushed ice, and diluted with ethyl acetate. The extract was washed with 1N HCl, water and brine, dried over MgSO$_4$, and concentrated. The residue was washed with ethanol and hexane to give the titled compound as colorless crystals (12.75 g).

$^1$H-NMR (CDCl$_3$) δ: 2.74 (3H, s), 3.42 (2H, t, J=6.6 Hz), 3.93 (2H, t, J=6.6 Hz), 7.28 (1H, dt, J=2.2, 8.8 Hz), 7.53 (1H, dd, J=9.4, 2.2 Hz), 7.79 (1H, dd, J=8.8, 4.8 Hz).

IR (KBr): 1649, 1518, 1368, 1289, 1179, 1152, 876, 820 cm$^{-1}$.

Reference Example 36

Preparation of 1-(5-fluoro-3-methylbenzo[b]thiophen-2-yl)-3-(1H-imidazol-1-yl)propan-1-one To a solution of the compound obtained in Reference Example 35 (10.97 g) in DMF (100 ml) was added 1H-imidazole (11.64 g). The mixture was stirred at room temperature for 1 hour, poured into water, and extracted with ethyl acetate. The extract was washed with water and brine, dried over MgSO$_4$, and concentrated. The residue was chromatographed on silica gel using ethyl acetate-ethanol (10:1) as an eluent to give the titled compound as colorless crystals (12.00 g).

$^1$H-NMR (CDCl$_3$) δ: 2.72 (3H, s), 3.39 (2H, t, J=6.4 Hz), 4.44 (2H, t, J=6.4 Hz), 7.00 (1H, s), 7.05 (1H, s), 7.28 (1H, dt, J=2.2, 8.8 Hz), 7.52 (1H, dd, J=9.4, 2.2 Hz), 7.58 (1H, s), 7.78 (1H, dd, J=8.8, 4.8 Hz).

IR (KBr): 1667, 1508, 1433, 1175, 1084, 853, 739, 662 cm$^{-1}$.

Reference Example 37

Preparation of 1-(5-fluoro-3-methylbenzo[b]thiophen-2-yl)-3 -(1H-imidazol-1-yl)propan-1-ol To a solution of the compound obtained in Reference Example 36 (9.00 g) in THF-methanol (1 :1, 120 ml) was added NaBH$_4$ (1.18 g) at 0° C. The mixture was stirred for 30 minutes, concentrated, diluted with water, and extracted with ethyl acetate. The extract was washed with brine, dried over MgSO$_4$, and concentrated to give the titled compound as colorless crystals (8.92 g).

$^1$H-NMR (CDCl$_3$) δ: 2.00–2.42 (2H, m), 2.17 (3H, s), 4.03–4.37 (2H, m), 4.87 (1H, dd, J=9.4, 2.4 Hz), 6.95 (1H, s), 7.02 (1H, s), 7.08 (1H, dt, J=2.6, 8.8 Hz), 7.28 (1H, dd, J=9.6, 2.6 Hz), 7.51 (1H, s), 7.72 (1H, dd, J=8.8, 5.2 Hz).

IR (KBr) 3144, 1445, 1179, 1078, 922, 745, 656 cm$^{-1}$.

EXAMPLE 21

Preparation of 1-[(E)-3-(5-fluoro-3-methylbenzo[b]thiophen-2-yl)-2-propen-1-yl]-1H-imidazole

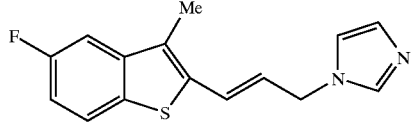

A mixture of the compound obtained in Reference Example 37 (5.00 g) and p-toluenesulfonic acid monohydrate (9.83 g) in toluene (150 ml) was heated at reflux for 3 hours. The mixture was concentrated, diluted with aqueous NaHCO$_3$, and extracted with ethyl acetate. The extract was washed with brine, dried over MgSO$_4$, and concentrated to give the titled compound as colorless crystals (4.65 g).

$^1$H-NMR (CDCl$_3$) δ: 2.34 (3H, s), 4.76 (2H, d J=6.2 Hz), 6.19 (1H, dt, J=15.4, 6.2 Hz), 6.80 (1H, d, J=15.4 Hz), 6.99 (1H, s), 7.08 (1H, dt, J=2.4, 8.8 Hz), 7.13 (1H, s), 7.29 (1H, dd, J=9.6, 2.4 Hz), 7.56 (1H, s), 7.65 (1H, dd, J=8.8, 4.8 Hz).

IR (KBr): 1443, 1225, 1169, 959, 860, 828, 797 cm$^{-1}$.

Reference Example 38

Preparation of 2-acetyl-5-fluoro-3-methylbenzo[b]thiophene

The titled compound (7.43 g) was prepared as colorless crystals from 5-fluoro-3-methylbenzo[b]thiophene (9.97 g) and acetyl chloride (5.55 ml) by the similar reaction and purification procedure as described in Reference Example 35.

$^1$H-NMR (CDCl$_3$) δ: 2.64 (3H, s), 2.72 (3H, s), 7.26 (1H, dt, J=2.2, 8.8 Hz), 7.52 (1H, dd, J=9.4, 2.2 Hz), 7.78 (1H, dd, J=8.8, 4.6 Hz).

IR (KBr): 1649, 1522, 1441, 1377, 1360, 1294, 1238, 1184, 845, 826 cm$^{-1}$.

Reference Example 39

Preparation of (E)-1l-(5-fluoro-3-methylbenzo[b]thiophen-2-yl)-3-(1-triphenylmethyl-1H-imidazol-4-yl)-2-propen-1-one To a mixture of the compound obtained in Reference Example 38 (7.13 g) and 1-triphenylmethyl-1H-imidazole-4-carboxaldehyde (12.18 g) in THF-methanol (1:1,240 ml) was added 6N NaOH (15 ml) at 0° C. The mixture was stirred at room temperature for 4 hours and poured into water. The precipitate was collected by filtration, and washed with ethanol and diisopropylether to give the titled compound as a colorless powder (18.00 g).

$^1$H-NMR (CDCl$_3$) δ: 2.77 (3H, s), 7.11–7.82 (22H, m).

IR (KBr): 1649, 1593, 1514, 1163, 1121, 702 cm$^{-1}$.

Reference Example 40

Preparation of 1-(5-fluoro-3-methylbenzo[b]thiophen-2-yl)-3-(1-triphenylmethyl-1H-imidazol-4-yl)propan-1-one A mixture of the compound obtained in Reference Example 39 (15.88 g) and 10% palladium-carbon (8.00 g) in THF (800 ml)-ethyl acetate (800 ml) was stirred at room temperature for 20 hours under hydrogen atmosphere. The catalyst was removed by filtration, and the filtrate was concentrated. The residue was titurated with diisopropylether to give the titled compound as colorless crystals (11.50 g).

$^1$H-NMR (CDCl$_3$) δ: 2.69 (3H, s), 3.01 (2H, t, J=7.0 Hz), 3.31 (2H, t, J=7.0 Hz), 6.60 (1H, d, J=1.4 Hz), 7.08–7.36 (17H, m), 7.51 (1H, dd, J=9.6, 2.0 Hz), 7.76 (1H, dd, J=8.8, 4.6 Hz).

IR (KBr): 1651, 1443, 1165, 752, 702 cm$^{-1}$.

Reference Example 41

Preparation of 1-(5-fluoro-3-methylbenzo[b]thiophen-2-yl)-3-(1-triphenylmethyl-1H-imidazol-4-yl)propan-1-ol The titled compound (9.78 g) was prepared as colorless crystals from the compound obtained in Reference Example 40 (9.75 g) by the similar reaction and purification procedure as described in Reference Example 37.

$^1$H-NMR (CDCl$_3$) δ: 2.11–2.20 (2H, m), 2.28 (3H, s), 2.79 (2H, q, J=6.0 Hz), 5.28 (1H, t, J=6.0 Hz), 6.58 (1H, s), 7.03 (1H, dt, J=2.4, 8.8 Hz), 7.11–7.42 (17H, m), 7.70 (1H, dd, J=8.8, 5.2 Hz).

IR (KBr): 3137, 1445, 748, 700 cm$^{-1}$.

EXAMPLE 22

Preparation of 4-[(E)-3-(5-fluoro-3-methylbenzo[b]thiophen-2-yl)-2-propen-1-yl]-1H-imidazole

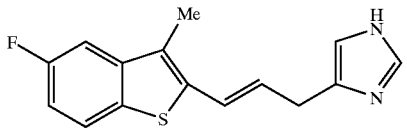

A mixture of the compound obtained in Reference Example 41 (7.90 g) and p-toluenesulfonic acid monohydrate (9.00 g) in 1,2-dimethoxyethane (150 ml) was heated at ref lux for 3 hours. The mixture was concentrated, diluted with aqueous NaHCO$_3$, and extracted with ethyl acetate. The extract was washed with brine, dried over MgSO$_4$, and concentrated. The residue was titurated with diisopropylether to give the titled compound as colorless crystals (3.21 g).

$^1$H-NMR (CDCl$_3$) δ: 2.32 (3H, s), 3.60 (2H, d, J=7.0 Hz), 6.27 (1H, dt, J=15.4, 7.0 Hz), 6.81 (1H, d, J=15.4 Hz), 6.87 (1H, s), 7.03 (1H, dt, J=2.4, 8.8 Hz), 7.25 (1H, dd, J=10.0, 2.4 Hz), 7.62 (1H, dd, J=8.8, 4.6 Hz), 7.63 (1H, s).

IR (KBr): 1599, 1445, 955, 810, 625 cm$^{-1}$.

Reference Example 42

Preparation of 5-methoxy-3-methylbenzo[b]thiophene-2-carboxaldehyde

The titled compound (4.20 g) was prepared as colorless crystals from 5-methoxy-3-methylbenzo[b]thiophene (6.00 g) by the similar reaction and purification procedure as described in Reference example 32.

$^1$H-NMR (CDCl$_3$) δ: 2.76 (3H, s), 3.91 (3H, s), 7.17 (1H, dd, J=8.8, 2.6 Hz), 7.25 (1H, d, J=2.6 Hz), 7.73 (1H, d, J=8.8 Hz).

IR (KBr): 1653, 1460, 1198, 829, 667 cm$^{-1}$.

Reference Example 43

Preparation of ethyl 3-(5-methoxy-3-methylbenzo[b]thiophen-2-yl)acrylate

The titled compound (3.28 g) was prepared as colorless crystals from the compound obtained in Reference Example 42 (2.50 g) by the similar reaction and purification procedure as described in Reference Example 2.

$^1$H-NMR (CDCl$_3$) δ: 1.35 (3H, t, J=7.0 Hz), 2.49 (3H, s), 3.89 (3H, s), 4.28 (2H, q, J=7.0 Hz), 6.26 (1H, d, J=15.6 Hz), 7.04 (1H, dd, J=8.8, 2.4 Hz), 7.12 (1H, d, J=2.4 Hz), 7.63 (1H, d, J=8.8 Hz), 8.03 (1H, d, J=15.6 Hz).

IR (KBr): 1709, 1628, 1460, 1308, 1171, 833 cm$^{-1}$.

Reference Example 44

Preparation of (E)-3-(5-methoxy-3-methylbenzo[b]thiophen-2-yl)-2-propen-1-ol

The titled compound (2.69 g) was prepared as colorless crystals from the compound obtained in Reference Example 43 (3.17 g) by the similar reaction and purification procedure as described in Reference Example 3.

$^1$H-NMR (CDCl$_3$) δ: 1.26 (1H, s), 2.37 (3H, s), 3.88 (3H, s), 4.36 (1H, dd, J=5.6, 1.4 Hz), 6.25 (1H, dt, J=15.6, 5.6

Hz), 6.92–7.02 (2H, m), 7.07 (1H, d, J=2.4 Hz), 7.60 (1H, d, J=8.8 Hz).

IR(KBr): 3376, 1597, 1458, 1229, 949, 837 cm$^{-1}$.

EXAMPLE 23

Preparation of 1-[(E)-3-(5-methoxy-3-methylbenzo[b]thiophen-2-yl)-2-propen-1-yl]-1H-imidazole

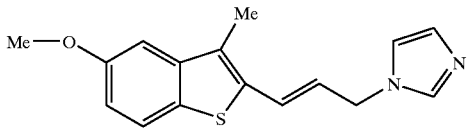

The titled compound (0.87 g) was prepared as colorless crystals from the compound obtained in Reference Example 44 (2.69 g) by the similar reaction and purification procedure as described in Example 20.

$^1$H-NMR (CDCl$_3$) δ: 2.34 (3H, s), 3.88 (3H, s), 4.75 (2H, dd, J=6.0, 1.4 Hz), 6.16 (1H, dt, J=15.6, 6.0 Hz), 6.81 (1H, dt, J=15.6, 1.4 Hz), 6.98 (1H, dd, J=8.8, 2.6 Hz), 6.99 (1H, s), 7.07 (1H, d, J=2.6 Hz), 7.12 (1H, s), 7.57 (1H, s), 7.60 (1H, d, J=8.8 Hz).

IR (KBr): 1595, 1458, 1427, 1227, 1202, 833, 665 cm$^{-1}$.

Reference Example 45

Preparation of ethyl 3-(benzo[b]thiophen-2-yl)acrylate

The titled compound (9.40 g) was prepared as colorless crystals from benzo[b]thiophen-2-carboxaldehyde (6.49 g) by the similar reaction and purification procedure as described in Reference example 2.

$^1$H-NMR (CDCl$_3$) δ: 1.35 (3H, t, J=7.2 Hz), 4.28 (2H, q, J=7.2 Hz), 6.30 (1H, d, J=15.6 Hz), 7.32–7.41 (2H, m), 7.46 (1H, s), 7.73–7.82 (2H, m), 7.87 (1H, d, J=15.6 Hz).

IR (KBr): 1701, 1630, 1269, 1167, 1038, 955, 824, 747, 727 cm$^{-1}$.

Reference Example 46

Preparation of (E)-3-(benzo[b]thiophen-2-yl)-2-propen-1-ol

The titled compound (6.86 g) was prepared as colorless crystals from the compound obtained in Reference Example 45 (8.75 g) by the similar reaction and purification procedure as described in Reference Example 3.

$^1$H-NMR (CDCl$_3$) δ: 4.35 (2H, dd, J=5.6, 1.6 Hz), 6.29 (1H, d, J=15.4, 5.6 Hz), 6.86 (1H, d, J=15.4 Hz), 7.15 (1H, s), 7.24–7.35 (2H, m), 7.65–7.78 (2H, m).

IR (KBr): 3281, 1088, 1005, 953, 741, 725 cm$^{-1}$.

EXAMPLE 24

Preparation of 1-[(E)-3-(benzo[b]thiophen-2-yl)-2-propen-1-yl]-1H-imidazole

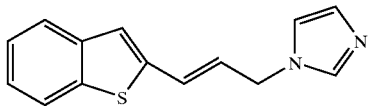

The titled compound (2.26 g) was prepared as colorless crystals from the compound obtained in Reference Example 46 (4.41 g) by the similar reaction and purification procedure as described in Example 20.

$^1$H-NMR (CDCl$_3$) δ: 4.74 (2H, d, J=6.0 Hz), 6.20 (1H, dt, J=15.4, 6.0 Hz), 6.68 (1H, d, J=15.4 Hz), 6.98 (1H, s), 7.13 (1H, s), 7.16 (1H, s), 7.29–7.36 (2H, m), 7.56 (1H, s), 7.67–7.78 (2H, m).

IR (KBr): 1503, 1433, 1223, 1074, 953, 758, 665 cm$^{-1}$.

Reference Example 47

Preparation of 3-chloro-1-(5-chloro-3-methylbenzo[b]thiophen-2-yl)propan-1-one

The titled compound (7.95 g) was prepared as colorless crystals from 5-chloro-3-methylbenzo[b]thiophene (9.13 g) by the similar reaction and purification procedure as described in Reference example 35.

$^1$H-NMR (CDCl$_3$) δ: 2.75 (3H, s), 3.42 (2H, t, J=6.6 Hz), 3.93 (2H, t, J=6.6 Hz), 7.47 (1H, dd, J=8.4, 2.2 Hz), 7.78 (1H, d, J=8.4 Hz), 7.87 (1H, d, J=2.2 Hz).

IR (KBr): 1667, 1510, 1346, 1179, 1080, 804 cm$^{-1}$.

Reference Example 48

Preparation of 1-(5-chloro-3-methylbenzo[b]thiophen-2-yl)-3-(1H-imidazol-1-yl)propan-1-one The titled compound (5.10 g) was prepared as colorless crystals from the compound obtained in Reference Example 47 (6.51 g) by the similar reaction and purification procedure as described in Reference Example 36.

$^1$H-NMR (CDCl$_3$) δ: 2.73 (3H, s), 3.39 (2H, t, J=6.4 Hz), 4.44 (2H, t, J=6.4 Hz), 6.99 (1H, s), 7.05 (1H, s), 7.47 (1H, dd, J=8.8, 1.8 Hz), 7.58 (1H, s), 7.76 (1H, d, J=8.8 Hz), 7.85 (1H, d, J=1.8 Hz).

IR (KBr): 1671, 1508, 1356, 1285, 1225, 1194, 1094, 1078, 804 cm$^{-1}$.

Reference Example 49

Preparation of 1-(5-chloro-3-methylbenzo[b]thiophen-2-yl)-3-(1H-imidazol-1-yl)propan-1-ol The titled compound (2.71 g) was prepared as colorless crystals from the compound obtained in Reference Example 48 (2.76 g) by the similar reaction and purification procedure as described in Reference Example 37.

$^1$H-NMR (CDCl$_3$) δ: 2.13 (3H, s), 2.04–2.40 (2H, m), 4.00–4.14 (1H, m), 4.25–4.40 (1H, m), 4.78 (1H, dd, J=9.6, 4.8 Hz), 6.93 (1H, s), 6.95 (1H, s), 7.27 (1H, dd, J=8.4, 2.0 Hz), 7.49 (1H, s), 7.58 (1H, d, J=2.0 Hz), 7.70 (1H, d, J=8.4 Hz).

IR (KBr): 3146, 1514, 1449, 1080, 802, 745 cm$^{-1}$.

EXAMPLE 25

Preparation of 1-[(E)-3-(5-chloro-3-methylbenzo[b]thiophen-2-yl)-2-propen-1-yl]-H-imidazole

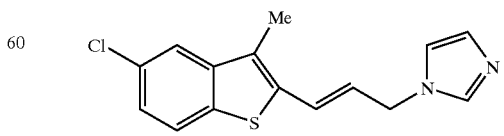

The titled compound (0.60 g) was prepared as colorless crystals from the compound obtained in Reference Example 49 (0.70 g) by the similar reaction and purification procedure as described in Example 21.

$^1$H-NMR (CDCl$_3$) δ: 2.34 (3H, s), 4.77 (2H, dd, J=6.0, 1.4 Hz), 6.19 (1H, dt, J=15.6, 6.0 Hz), 6.80 (1H, dt, J=15.6, 1.4 Hz), 7.00 (1H, s), 7.13 (1H, s), 7.29 (1H, dd, J=8.4, 2.2 Hz), 7.57 (1H, s), 7.61 (1H, d, J=2.2 Hz), 7.65 (1H, d, J=8.4 Hz).

IR (KBr): 3106, 1507, 1437, 1231, 1074, 951, 839, 804 cm$^{-1}$.

Reference Example 50

Preparation of ethyl 3-(benzo[b]thiophen-5-yl)acrylate

The titled compound (3.35 g) was prepared as a pale brown oil from benzo[b]thiophen-5-carboxaldehyde (2.30 g) by the similar reaction and purification procedure as described in Reference example 2.

$^1$H-NMR (CDCl$_3$) δ: 1.35 (3H, t, J=7.0 Hz), 4.28 (2H, q, J=7.0 Hz), 6.51 (1H, d, J=16.0 Hz), 7.36 (1H, d, J=5.2 Hz), 7.48–7.57 (2H, m), 7.78–7.95 (3H, m).

IR (KBr): 1713, 1636, 1283, 1181 cm$^{-1}$.

Reference Example 51

Preparation of (E)-3-(benzo[b]thiophen-5-yl)-2-propen-1-ol

The titled compound (2.21 g) was prepared as colorless crystals from the compound obtained in Reference Example 50 (3.35 g) by the similar reaction and purification procedure as described in Reference Example 3.

$^1$H-NMR (CDCl$_3$) δ: 4.36 (2H, d, J=5.6 Hz), 6.43 (1H, dt, J=15.8, 5.6 Hz), 6.74 (1H, d, J=15.8 Hz), 7.31 (1H, d, J=5.6 Hz), 7.41–7.45 (2H, m), 7.79–7.84 (2H, m).

IR (KBr): 3279, 1090, 1009, 970, 694 cm$^{-1}$.

EXAMPLE 26

Preparation of 1-[(E)-3-(benzo[b]thiophen-5-yl)-2-propen-1-yl]-1H-imidazole

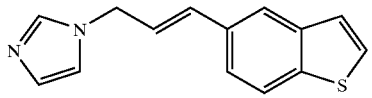

The titled compound (1.30 g) was prepared as colorless crystals from the compound obtained in Reference Example 51 (1.90 g) by the similar reaction and purification procedure as described in Example 21.

$^1$H-NMR (CDCl$_3$) δ: 4.75 (2H, d, J=6.2 Hz), 6.35 (1H, dt, J=15.8, 6.2 Hz), 6.65 (1H, d, J=15.8 Hz), 7.00 (1H, s), 7.11 (1H, s), 7.31 (1H, d, J=5.4 Hz), 7.40 (1H, dd, J=8.2, 1.2 Hz), 7.46 (1H, d, J=5.4 Hz), 7.57 (1H, s), 7.78 (1H, d, J=1.2 Hz), 7.83 (1H, d, J=8.2 Hz).

IR (KBr): 1503, 1225, 1086, 974, 808 cm$^{-1}$.

Reference Example 52

Preparation of 1-(5-fluorobenzo[b]thiophen-2-yl)-3-(1-triphenylmethyl-1H-imidazol-4-yl)-propan-1-ol To a solution of 5-fluorobenzo[b]thiophene (1.22 g) in THF (22 ml) was added n-BuLi (1.6 M solution in hexane, 5.0 ml) at −78° C., and the mixture was stirred for 1 hour. To this mixture was added a solution of 3-(1-triphenylmethyl-1H-imidazole-4-yl)propanal (2.93 g) in THF (10 ml), and the mixture was allowed to warm to −40° C. over 1 hour. The mixture was diluted with 10% aqueous ammonium chloride, warmed to room temperature, and extracted with ethyl acetate. The extract was washed with brine, dried over MgSO$_4$, and concentrated. The residue was chromatographed on silica gel using hexane-ethyl acetate (1:1) as an eluent to give the titled compound as colorless crystals (2.58 g).

$^1$H-NMR (CDCl$_3$) δ: 2.16–2.33 (2H, m), 2.65–2.90 (2H, m), 5.17 (1H, dd, J=6.6, 4.6 Hz), 6.56 (1H, d, J=1.2 Hz), 7.01 (1H, dt, J=2.6, 8.8 Hz), 7.11–7.18 (7H, m), 7.31–7.39 (11H, m), 7.70 (1H, dd, J=8.8, 4.8 Hz).

IR (KBr): 1447, 746, 704 cm$^{-1}$.

EXAMPLE 27

Preparation of 4-[(E)-3-(5-fluorobenzo[d]thiophen-2-yl)-2-propen-1-yl]-1H-imidazole

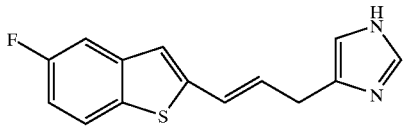

A mixture of the compound obtained in Reference Example 52 (2.58 g), p-toluenesulfonic acid monohydrate (3.00 g), and 1,2-dimethoxyethane (50 ml) was heated at reflux for 5 hours. The mixture was concentrated, diluted with aqueous NaHCO$_3$, and extracted with ethyl acetate. The extract was washed with brine, dried over MgSO$_4$, concentrated, and chromatographed on silica gel using CH$_2$Cl$_2$-methanol (40:1) as an eluent. The product was washed with ether to give the titled compound (0.28 g) as colorless crystals.

$^1$H-NMR (CDCl$_3$) δ: 3.58 (2H, d, J=6.8 Hz), 6.31 (1H, dt, J=15.8, 6.8 Hz), 6.68 (1H, d, J=15.8 Hz), 6.87 (1H, s), 7.02 (1H, dt, J=2.6, 8.8 Hz), 7.02 (1H, s), 7.31 (1H, dd, J=9.2, 2.6 Hz), 7.63 (1H, s), 7.64 (1H, dd, J=8.8, 5.2 Hz).

IR (KBr): 1441, 1175, 955, 868, 835, 806 cm$^{-1}$.

Reference Example 53

Preparation of 5,7-difluoro-3-methylbenzo[b]thiophene

To a mixture of 2,4-difluorothiophenol (4.95 g) and chloroacetone (2.8 ml) in DMF (30 ml) was added potassium carbonate (9.67 g) at 0° C. The mixture was stirred for 3 hours, poured into water, and extracted with ethyl acetate. The extract was washed with 10% aqueous citric acid, water, and brine, dried over MgSO$_4$, and concentrated to give 1-(2,4-difluorophenylthio)propan-2-one (6.80 g). This compound was dissolved in toluene and heated at reflux for 30 hours with polyphosphoric acid (24 g). The solvent was evaporated, and the mixture was heated at 150° C. for 1 hour, carefully neutralized with aqueous potassium carbonate with ice-cooling, and extracted with ethyl acetate. The extract was washed with water and brine, dried over MgSO$_4$, and concentrated. The residue was chromatographed on silica gel using hexane as an eluent to give the titled compound as colorless crystals (2.00 g).

$^1$H-NMR (CDCl$_3$) δ: 2.40 (3H, s), 6.88 (1H, dt, J=2.2, 9.2 Hz), 7.18 (1H, s), 7.21 (1H, dd, J=9.2, 2.2 Hz).

IR (KBr): 1624, 1576, 1418, 1111, 984, 839 cm$^{-1}$.

Reference Example 54

Preparation of 1-(5,7-difluoro-3-methylbenzo[b] thiophen-2-yl)-3-(1-triphenylmethyl-1H-imidazol-4-yl)propan-1-ol The titled compound (3.05 g) was prepared as colorless crystals from the compound obtained in Reference Example 53 (1.84 g) by the similar reaction and purification procedure as described in Reference Example 52.

$^1$H-NMR (CDCl$_3$) δ: 2.05–2.54 (2H, m), 2.37 (3H, s), 2.76 (2H, t, J=6.8 Hz), 5.28 (1H, dd, J=8.8, 4.8 Hz), 6.57 (1H,s), 7.10–7.40 (18H, m).

IR (KBr)$_x$: 3061, 1445, 1224, 748, 702 cm$^{-1}$.

EXAMPLE 28

Preparation of 4-[(E)-3-(5,7-difluoro-3-methylbenzo[b]thiophen-2-yl)-2-propen-1-yl]-1H-imidazole

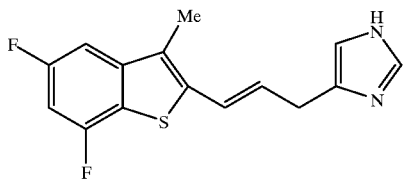

A mixture of the compound obtained in Reference Example 54 (3.04 g), p-toluenesulfonic acid monohydrate (4.18 g), 1,2-diethoxyethane (40 ml), and 1,2-dimethoxyethane (10 ml) was heated at reflux for 3 hours. The mixture was concentrated, diluted with aqueous NaHCO$_3$, and extracted with ethyl acetate. The extract was washed with brine, dried over MgSO$_4$, concentrated, and chromatographed on silica gel using ethyl acetate-ethanol (20:1) as an eluent. The product was washed with ether to give the titled compound (1.08 g) as colorless crystals.

$^1$H-NMR (CDCl$_3$) δ: 2.37 (3H, s), 3.63 (2H,.d, J=6.0 Hz), 6.58–6.79 (2H, m), 6.89 (1H, s), 7.12–7.21 (2H, m), 7.64 (1H, s).

IR (KBr): 3086, 2822, 2640, 1422, 972, 839, 818, 623 cm$^{-1}$.

Reference Example 55

Preparation of ethyl 6-fluorobenzo[b]thiophene-2-carboxylate

To a mixture of 2,4-difluorobenzaldehyde (50.17 g) and potassium carbonate (63.4 g) in DMF (500 ml) was added ethyl thioglycolate (38.7 ml) dropwise at 0° C. The mixture was stirred at room temperature for 18 hours, diluted with water, and extracted with ethyl acetate. The extract was washed with 10% aqueous citric acid, water, and brine, dried over MgSO$_4$, and concentrated. The residue was chromatographed on silica gel using hexane-ethyl acetate (20:1) as an eluent to give the titled compound as colorless crystals (16.61 g).

$^1$H-NMR (CDCl$_3$) δ: 1.42 (3H, t, J=7.0 Hz), 4.41 (2H, q, J=7.0 Hz), 7.17 (1H, dt, J=2.4, 8.8 Hz), 7.54 (1H, dd, J=8.8, 2.4 Hz), 7.83 (1H, dd, J=8.8, 5.2 Hz), 8.02 (1H, s).

IR (KBr): 1705, 1530, 1260, 1202, 878, 752 cm$^{-1}$.

Reference Example 56

Preparation of 6-fluorobenzo[b]thiophene-2-carboxylic acid

To a solution of the compound obtained in Reference Example 55 (6.10 g) in ethanol (60 ml) was added 2.5N sodium hydroxide (50 ml). The mixture was heated at reflux for 1 hour, concentrated, diluted with water, adjusted to pH 1 with 2N HCl, and extracted with ethyl acetate. The extract was washed with brine, dried over MgSO$_4$, and concentrated to give the titled compound as colorless crystals (5.27 g).

$^1$H-NMR (DMSO-d$_6$) δ: 7.35 (1H, dt, J=2.6, 9.0 Hz), 7.97 (1H, dd, J=9.6, 2.6 Hz), 8.05 (1H, dd, J=9.0, 5.4 Hz), 8.11 (1H, s).

IR (KBr): 1524, 1256, 1200, 918, 806, 756, 527 cm$^{-1}$.

Reference Example 57

Preparation of 6-fluorobenzo[b]thiophene

A mixture of the compound obtained in Reference Example 56 (4.90 g), powdered copper (0.50 g), and quinoline (26 ml) was heated at 180–190° C. for 1 hour. The reaction mixture was cooled, poured into ice-water, adjusted to pH 1 with concentrated HCl, and extracted with ethyl acetate. The extract was washed with 2N HCl and brine, dried over MgSO$_4$, and concentrated. The residue was chromatographed on silica gel using hexane as an eluent to give the titled compound as a pale brown oil (3.58 g).

$^1$H-NMR (CDCl$_3$) δ: 7.12 (1H, dt, J=2.6, 8.8 Hz), 7.30 (1H, d, J=5.4 Hz), 7.39 (1H, d, J=5.4 Hz), 7.56 (1H, dd, J=8.4, 2.6 Hz), 7.75 (1H, dd, J=8.8, 5.2 Hz).

IR (KBr):1470, 912 cm$^{-1}$.

Reference Example 58

Preparation of 1-(6-fluorobenzo[b]thiophen-2-yl)-3-(1-triphenylmethyl-1H-imidazol-4-yl)-propan-1-ol The titled compound (8.35 g) was prepared as colorless crystals from the compound obtained in Reference Example 57 (3.04 g) by the similar reaction and purification procedure as described in Reference Example 52.

$^1$H-NMR (CDCl$_3$) δ: 2.04–2.27 (2H, m), 2.65–2.81 (2H, m), 5.14 (1H, dd, J=6.6, 4.6 Hz), 6.56 (1H, s), 7.05 (1H, dt, J=2.2, 8.8 Hz), 7.10–7.15 (7H, m), 7.32–7.39 (1OH, m), 7.47 (1H, dd, J=8.8, 2.2 Hz), 7.60 (1H, dd, J=8.8, 5.6 Hz).

IR (KBr): 3167, 1466, 1449, 851, 748, 702 cm$^{-1}$.

EXAMPLE 29

Preparation of 4-[(E)-3-(6-fluorobenzo[b]thiophen-2-yl)-2-propen-1-yl]-1H-imidazole

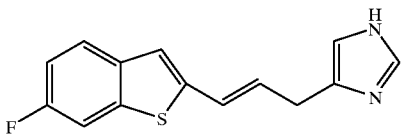

The titled compound (0.90 g) was prepared as colorless crystals from the compound obtained in Reference Example 58 (7.69 g) by the similar reaction and purification procedure as described in Example 28.

$^1$H-NMR (CDCl$_3$) δ: 3.56 (2H, d, J=6.6 Hz), 6.24 (1H, dt, J=15.6, 6.6 Hz), 6.65 (1H, d, J=15.6 Hz), 6.86 (1H, s), 7.01 (1H, s), 7.03 (1H, dt, J=2.2, 8.8 Hz), 7.40 (1H, dd, J=8.8, 2.2 Hz), 7.57 (1H, dd, J=8.8, 5.2 Hz), 7.61 (1H, s).

IR (KBr): 3069, 2830, 1566, 1468, 1250, 949, 856, 816 cm$^{-1}$.

Reference Example 59

Preparation of 6-fluorobenzo[b]thiophene-2-methanol

To a solution of the compound obtained in Reference Example 55 (5.00 g) in THF (100 ml) was added diisobutylaluminum hydride (0.96 M solution in hexane, 60.0 ml) dropwise at −78° C. The reaction mixture was allowed to warm to 0° C. over 3 hours and diluted with 1N HCl. The mixture was extracted with ethyl acetate. The extract was washed with 1N HCl, water, and brine, dried over MgSO$_4$, and concentrated to give the titled compound as colorless crystals (4.02 g).

$^1$H-NMR (CDCl$_3$) δ: 1.85–2.00 (1H, br), 4.92 (2H, brd, J=3.6 Hz), 7.10 (1H, dt, J=2.6, 8.8 Hz), 7.18 (1H, s), 7.50 (1H, dd, J=8.8, 2.6 Hz), 7.66 (1H, dd, J=8.8, 5.0 Hz).

IR (KBr) 3220, 1541, 1470, 1120, 1017, 851 cm$^{-1}$.

Reference Example 60

Preparation of 6-fluorobenzo[b]thiophene-2-carboxaldehyde

A mixture of the compound obtained in Reference Example 59 (3.88 g) and manganese (IV) oxide (23.0 g) in 1,2-dimethoxyethane (60 ml)-toluene (60 ml) was heated at reflux for 3 hours. The insolubles were filtered off and the filtrate was evaporated. The residue was chromatographed on silica gel using ethyl acetate as an eluent to give the titled compound as pale yellow crystals (1.95 g).

H-NMR (CDCl$_3$) δ: 7.21 (1H, dt, J=2.4, 8.8 Hz), 7.59 (1H, dd, J=8.8, 2.4 Hz), 7.92 (1H, dd, J=8.8, 5.0 Hz), 8.01 (1H, s), 10.08 (1H, s).

IR (KBr): 1667, 1601, 1518, 1258, 1190, 1130, 858, 660 cm$^{-1}$.

Reference Example 61

Preparation of ethyl 3-(6-fluorobenzo[b]thiophen-2-yl)acrylate

The titled compound (2.60 g) was prepared as colorless crystals from the compound obtained in Reference Example 60 (1.88 g) by the similar reaction and purification procedure as described in Reference Example 2.

$^1$H-NMR (CDCl$_3$) δ1.35 (3H, t, J=7.0 Hz), 4.27 (2H, q, J=7.0 Hz), 6.26 (1H, d, J=15.8 Hz), 7.11 (1H, dt, J=2.4, 8.8 Hz), 7.41 (1H, s), 7.48 (1H, dd, J=8.8, 2.4 Hz), 7.71 (1H, dd, J=8.8, 5.2 Hz), 7.84 (1H, d, J=15.8 Hz).

IR (KBr): 1711, 1634, 1267, 1169, 1146, 835 cm$^{-1}$.

Reference Example 62

Preparation of (E)-3-(6-fluorobenzo[b]thiophen-2-yl)-2-propen-1-ol

The titled compound (2.17 g) was prepared as colorless crystals from the compound obtained in Reference Example 61 (2.58 g) by the similar reaction and purification procedure as described in Reference Example 3.

$^1$H-NMR (CDCl$_3$) δ4.35 (2H, d, J=5.6 Hz), 6.24 (1H, dt, J=15.8, 5.6 Hz), 6.84 (1H, d, J=15.8 Hz), 7.06 (1H, dt, J=2.2, 8.8 Hz), 7.10 (1H, s), 7.44 (1H, dd, J=8.8, 2.2 Hz), 7.61 (1H, dd, J=8.8, 5.2 Hz).

IR (KBr): 3299, 1566, 1468, 1254, 1086, 951, 856, 588 cm$^{-1}$.

EXAMPLE 30

Preparation of 1-[(E)-3-(6-fluorobenzo[b]thiophen-2-yl)-2-propen-1-yl]-1H-imidazole

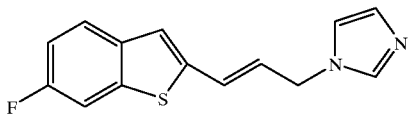

The titled compound (1.69 g) was prepared as colorless crystals from the compound obtained in Reference Example 62 (2.14 g) by the similar reaction and purification procedure as described in Example 20.

H-NMR (CDCl$_3$) δ: 4.74 (2H, d, J=6.0 Hz), 6.16 (1H, dt, J=15.8, 6.0 Hz), 6.64 (1H, d, J=15.8 Hz), 6.98 (1H, s), 7.02–7.13 (3H, m), 7.44 (1H, dd, J=8.8, 2.2 Hz), 7.56 (1H, s), 7.63 (1H, dd, J=8.8, 5.2 Hz).

IR(KBr): 1505, 1466, 1250, 1221, 1073, 955, 855, 820, 752, 665 cm$^{-1}$.

| Preparation 1 | |
|---|---|
| Capsules | |
| (1) Compound obtained in Example 2 | 10 mg |
| (2) lactose | 90 mg |
| (3) microcrystalline cellulose | 70 mg |
| (4) magnesium stearate | 10 mg |
| One capsule | 180 mg |

The above (1), (2) and (3) and 5 mg of (4) were mixed. The mixture was granulated. To the granules was added (4) remaining. The whole content was sealed in a gelatin capsule.

| Preparation 2 | |
|---|---|
| Tablets | |
| (1) Compound obtained in Example 2 | 10 mg |
| (2) lactose | 35 mg |
| (3) corn starch | 150 mg |
| (4) microcrystalline cellulose | 30 mg |
| (5) magnesium stearate | 5 mg |
| One tablet | 230 mg |

The above (1), (2) and (3), 20 mg of (4) and 2.5r mg of (5) were mixed. The mixture was granulated. To the granules was added remaining 10 mg of (4) and 2.5 mg of (5) were added, and the mixture was compressively molded to give a tablet.

Experiment 1

Assay of inhibitory activity on rat steroid C$_{17-20}$-lyase in vitro

Inhibitory activity was determined according to the method described in The Prostate, vol.26, 140–150(1995) with some modifications.

Testes excised from 13-week old, male SD rats were homogenized, and testicular microsomes were prepared by a series of centrifugation. The microsome protein (7 μg/10

μl) was added to 10 μl of 100 mM phosphate buffer (pH 7.4) in which 10 nM (final concentration) [1,2-³H]-17α-hydroxyprogesterone, NADPH, and test compounds were dissolved. The reaction mixture was incubated for 7 min at 37° C., terminated by addition of 40 μl of Ethyl acetate, and briefly centrifuged. The substrate and the products (testosterone and androstenedione) in the upper phase were separated by silica gel thin layer chromatography. Detection of the spots and measurement of the radioactivity were performed by a BAS 2000 Bioimage analyzer. The concentration of the test compounds necessary to reduce the concentration of the products by 50% (The concentration in the control group in which no test compound was added was taken as 100%) was calculated, and shown in Table 1.

TABLE 1

| Test compound | IC$_{50}$ (nM) |
| --- | --- |
| 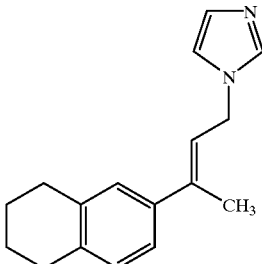 | 26 |
| 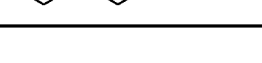 | 13 |
| 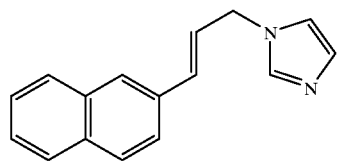 | 20 |
| 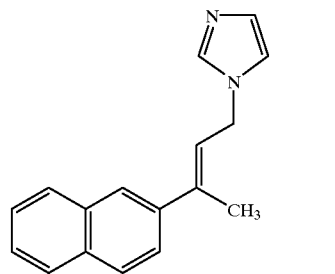 | 100 |
| 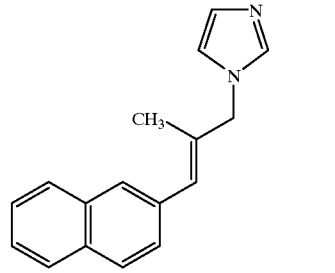 | 190 |

TABLE 1-continued

| Test compound | IC$_{50}$ (nM) |
| --- | --- |
| 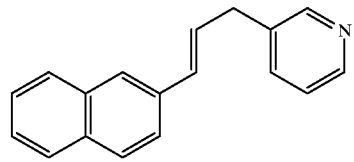 | 28 |

INDUSTRIAL APPLICABILITY

The compounds of the present invention and salts thereof have an inhibitory activity of steroid C$_{17,20}$-lyase and are useful for preventing and treating mammals suffering from, for example, primary tumor, its metastasis and recurrence thereof, and various symptoms accompanied with these cancers, various diseases such as prostatic hypertrophy, virilism, hirsutism, male pattern alopecia, precocious puberty, endometriosis, uterus myoma, mastopathy, polycystic ovary syndrome, etc.

What is claimed is:
1. A compound of the formula:

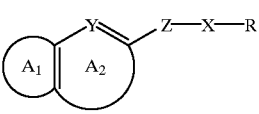

(I)

wherein
A$_1$ is
(1) a C$_6$ cycloalkene or (2) benzene, each of which is unsubstituted or substituted by one to three substituents selected from the group consisting of
1) a C$_{1-6}$ alkyl group,
2) a C$_{1-6}$ alkyl group substituted by a halogen, a C$_{1-3}$ alkoxy, hydroxyl, amino or an amino group substituted by a C$_{1-3}$ alkyl,
3) a C$_{1-6}$ alkoxy group,
4) a C$_{1-6}$ alkoxy group substituted by a halogen, a C$_{1-3}$ alkoxy, hydroxyl, amino or an amino group substituted by a C$_{1-3}$ alkyl,
5) a carboxyl group,
6) a C$_{1-6}$ alkoxy-carbonyl,
7) carbamoyl,
8) a carbamoyl group substituted by one or two of C$_{1-6}$ alkyl groups which is unsubstituted or substituted by 1 to 3 substituents selected from the group consisting of (1) a halogen, (2) an C$_{1-4}$ alkoxy group unsubstituted or substituted by 1 to 3 halogen atoms, (3) an C$_{1-4}$ alkyl group unsubstituted or substituted by 1 to 3 halogen atoms and (4) nitro,
9) thiocarbamoyl,
10) a thiocarbamoyl group substituted by one or two of C$_{1-6}$ alkyl groups which is unsubstituted or substituted by 1 to 3 substituents selected from the group consisting of (1) a halogen, (2) an C$_{1-4}$ alkoxy group unsubstituted or substituted by 1 to 3 halogen atoms, (3) an C$_{1-4}$ alkyl group unsubstituted or substituted by 1 to 3 halogen atoms and (4) nitro, 11) amino,
12) an amino group substituted by one or two of $C_{1-6}$ alkyl group which is unsubstituted or substituted by 1 to 3 substituents selected from the group consisting of (1) a halogen, (2) an $C_{1-4}$ alkoxy group unsubstituted or substituted by 1 to 3 halogen atoms, (3) an $C_{1-4}$ alkyl group unsubstituted or substituted by 1 to 3 halogen atoms and (4) nitro,
13) hydroxyl,
14) a hydroxyl substituted by a $C_{1-6}$ alkyl which may have 1 to 5 substituents selected from the group consisting of (1) a halogen, (2) an alkoxy group unsubstituted or substituted by 1 to 3 halogen atoms, (3) an alkyl group unsubstituted or substituted by 1 to 3 halogen atoms, (4) nitro, (5) amino and (6) cyano,
15) thiol (mercapto),
16) a thiol unsubstituted or substituted by a $C_{1-6}$ alkyl which may have 1 to 5 substituents selected from the group consisting of (1) a halogen, (2) an alkoxy group unsubstituted or substituted by 1 to 3 halogen atoms, (3) an alkyl group unsubstituted or substituted by 1 to 3 halogen atoms, (4) nitro, (5) amino and (6) cyano,
17) formyl,
18) a $C_{1-6}$ alkyl carbonyl group unsubstituted or substituted by 1 to 5 substituents selected from the group consisting of a halogen atom, a lower alkoxy group and a lower alkyl group,
19) a $C_{1-6}$ sulfinyl group unsubstituted or substituted by 1 to 5 substituents selected from the group consisting of a halogen atom, a lower alkoxy group and a lower alkyl group,
20) a $C_{1-6}$ sulfonyl group unsubstituted or substituted by 1 to 5 substituents selected from the group consisting of a halogen atom, a lower alkoxy group and a lower alkyl group,
21) a halogen atom,
22) a nitro group,
23) a cyano group and
24) an oxo group, $A_2$ is benzene, furan, thiophene or pyridine, each of which is unsubstituted or substituted by 1 to 3 substituents selected from the group consisting of
(1) a $C_{1-6}$ alkyl group,
(2) a $C_{1-6}$ alkyl group substituted by 1 to three substituents selected from the group consisting of a halogen, a ($C_{1-3}$)alkoxy, hydroxyl, amino, methylamino, dimethylamino and diethylamino,
(3) a $C_{1-6}$ alkoxy group,
(4) a $C_{1-6}$ alkoxy group substituted by 1 to three substituents selected from the group consisting of a halogen, a ($C_{1-3}$)alkoxy, hydroxyl, amino, methylamino, dimethylamino and diethylamino,
(5) a $C_{6-10}$ aryl group,
(6) a $C_{6-10}$ aryl group substituted by substituted by 1 to 5 substituents selected from the group consisting of (1) a halogen atom, (2) a $C_{1-3}$ alkyl group, (3) amino, (4) an amino group substituted by a $C_{1-3}$ alkyl, (5) a hydroxyl group, (6) a nitro group and (7) a cyano group,
(7) $C_{4-7}$ cycloalkyl group,
(8) $C_{4-7}$ cycloalkyl group substituted by substituted by 1 to 5 substituents selected from the group consisting of (1) a halogen atom, (2) a $C_{1-3}$ alkyl group, (3) amino, (4) an amino group substituted by a $C_{1-3}$ alkyl, (5) a hydroxyl group, (6) a nitro group and (7) a cyano group,
(9) a $C_{3-6}$ cycloalkenyl group,
(10) a $C_{3-6}$ cycloalkenyl group substituted by substituted by 1 to 5 substituents selected from the group consisting of (1) a halogen atom, (2) a $C_{1-3}$ alkyl group, (3) amino, (4) an amino group substituted by a $C_{1-3}$ alkyl, (5) a hydroxyl group, (6) a nitro group and (7) a cyano group,
(11) carboxyl,
(12) a $C_{1-6}$ alkoxy-carbonyl,
(13) a $C_{6-10}$ aryl-oxycarbonyl,
(14) a $C_{7-10}$ aralkyl-oxycarbonyl,
(15) carbamoyl,
(16) a carbamoyl group substituted by one or two substituents selected from the group consisting of
1) a $C_{1-6}$ alkyl unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
2) a $C_{3-6}$ cycloalkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
3) a $C_{6-10}$ aryl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
4) a $C_{7-12}$ aralkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group, and
5) a $C_{6-10}$ arylsulfonyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
(17) a cyclic amino-carbonyl whose cyclic amino is selected from the group consisting of 1-azetidinyl, 1-pyrrolidinyl, piperidino, morpholino, thiomorpholino and 1-piperazinyl,
(18) thiocarbamoyl,
(19) a thiocarbamoyl group substituted by one or two substituents selected from the group consisting of
1) a $C_{1-6}$ alkyl unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
2) a $C_{3-6}$ cycloalkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
3) a $C_{6-10}$ aryl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
4) a $C_{7-12}$ aralkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group, and
5) a $C_{6-10}$ arylsulfonyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
(20) a cyclic amino-thiocarbonyl whose cyclic amino is selected from the group consisting of 1-azetidinyl, 1-pyrrolidinyl, piperidino, morpholino, thiomorpholino and 1-piperazinyl,
(21) amino,
(22) an amino group substituted by one or two substituents selected from the group consisting of
1) a $C_{1-6}$ alkyl unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
2) a $C_{3-6}$ cycloalkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
3) a $C_{6-10}$ aryl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
4) a $C_{7-12}$ aralkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group, and
5) a $C_{6-10}$ arylsulfonyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
(23) a cyclic amino selected from the group consisting of 1-azetidinyl, 1-pyrrolidinyl, piperidino, morpholino, thiomorpholino and 1-piperazinyl,
(24) hydroxyl,
(25) a hydroxyl group substituted by
1) a $C_{1-6}$ alkyl unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano,
2) a $C_{3-6}$ cycloalkyl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano,
3) a $C_{6-10}$ aryl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano or
4) a $C_{7-12}$ aralkyl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano,
(26) thiol (mercapto),
(27) a thiol (mercapto) group substituted by
1) a $C_{1-6}$ alkyl unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano,
2) a $C_{3-6}$ cycloalkyl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano,
3) a $C_{6-10}$ aryl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano or
4) a $C_{7-12}$ aralkyl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano,
(28) formyl,
(29) a $C_{1-6}$ alkyl carbonyl group unsubstituted or substituted by 1 to 5 substituents selected from the group consisting of a halogen atom, a lower alkoxy group and a lower alkyl group,
(30) a $C_{1-6}$ sulfinyl group unsubstituted or substituted by 1 to 5 substituents selected from the group consisting of a halogen atom, a lower alkoxy group and a lower alkyl group,
(31) a $C_{1-6}$ sulfonyl group unsubstituted or substituted by 1 to 5 substituents selected from the group consisting of a halogen atom, a lower alkoxy group and a lower alkyl group,
(32) a halogen atom,
(33) nitro and
(34) cyano, X is an $C_{1-6}$ alkylene,
Y is a methine group,
Z is a group of the formula:

$$-CR^1=CR^2-$$

wherein each of $R^1$ and $R^2$ is selected from the group consisting of (1) a hydrogen atom,
(2) a fluorine atom,
(3) a $C_{1-6}$ alkyl group,
(4) a $C_{1-6}$ alkyl group substituted by 1 to three substituents selected from the group consisting of a halogen, a $(C_{1-3})$alkoxy, hydroxyl, amino, methylamino, dimethylamino and diethylamino,
(5) a $C_{1-6}$ alkoxy group,
(6) a $C_{1-6}$ alkoxy group substituted by 1 to three substituents selected from the group consisting of a halogen, a $(C_{1-3})$alkoxy, hydroxyl, amino, methylamino, dimethylamino and diethylamino,
(7) a $C_{6-10}$ aryl group,
(8) a $C_{6-10}$ aryl group substituted by 1 to 5 substituents selected from the group consisting of (1) a halogen atom, (2) a $C_{1-3}$ alkyl group, (3) amino, (4) an amino group substituted by a $C_{1-3}$ alkyl, (5) a hydroxyl group, (6) a nitro group and (7) a cyano group,
(9) a $C_{4-7}$ cycloalkyl group,
(10) a $C_{4-7}$ cycloalkyl group substituted by substituted by 1 to 5 substituents selected from the group consisting of (1) halogen atom, (2) a $C_{1-3}$ alkyl group, (3) amino, (4) an amino group substituted by a $C_{1-3}$ alkyl, (5) a hydroxyl group, (6) a nitro group and (7) a cyano group,
(11) a $C_{3-6}$ cycloalkenyl group,
(12) a $C_{3-6}$ cycloalkenyl group substituted by substituted by 1 to 5 substituents selected from the group consisting of (1) a halogen atom, (2) a $C_{1-3}$ alkyl group, (3) amino, (4) an amino group substituted by a $C_{1-3}$ alkyl, (5) a hydroxyl group, (6) a nitro group and (7) a cyano group,
(13) carboxyl,
(14) a $C_{1-6}$ alkoxy-carbonyl,
(15) a $C_{6-10}$ aryl-oxycarbonyl,
(16) a $C_{7-10}$ aralkyl-oxycarbonyl,
(17) carbamoyl,
(18) a carbamoyl group substituted by one or two substituents selected from the group consisting of
  1) a $C_{1-6}$ alkyl unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
  2) a $C_{3-6}$ cycloalkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
  3) a $C_{6-10}$ aryl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
  4) a $C_{7-12}$ aralkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group, and
  5) a $C_{6-10}$ arylsulfonyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
(19) a cyclic amino-carbonyl whose cyclic amino is selected from the group consisting of 1-azetidinyl, 1-pyrrolidinyl, piperidino, morpholino, thiomorpholino and 1-piperazinyl,
(20) thiocarbamoyl,
(21) a thiocarbamoyl group substituted by one or two substituents selected from the group consisting of
  1) a $C_{1-6}$ alkyl unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
  2) a $C_{3-6}$ cycloalkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
  3) a $C_{6-10}$ aryl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
  4) a $C_{7-12}$ aralkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group, and
  5) a $C_{6-10}$ arylsulfonyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
(22) a cyclic amino-thiocarbonyl whose cyclic amino is selected from the group consisting of 1-azetidinyl, 1-pyrrolidinyl, piperidino, morpholino, thiomorpholino and 1-piperazinyl,
(23) amino,
(24) an amino group substituted by one or two substituents selected from the group consisting of
  1) a $C_{1-6}$ alkyl unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
  2) a $C_{3-6}$ cycloalkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,
  3) a $C_{6-10}$ aryl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group, 4) a $C_{7-12}$ aralkyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group, and 5) a $C_{6-10}$ arylsulfonyl group unsubstituted or substituted by one to five substituents selected from the group consisting of (1) a halogen, (2) an alkoxy group unsubstituted or substituted by 1 to 3 halogen atoms, (3) an alkyl group unsubstituted or substituted by 1 to 3 halogen atoms and (4) a nitro group,

(25) a cyclic amino selected from the group consisting of 1-azetidinyl, 1-pyrrolidinyl, piperidino, morpholino, thiomorpholino and 1-piperazinyl,

(26) hydroxyl,

(27) a hydroxyl group substituted by
1) a $C_{1-6}$ alkyl unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano, 2) a $C_{3-6}$ cycloalkyl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano, 3) a $C_{6-10}$ aryl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano or 4) a $C_{7-12}$ aralkyl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano,

(28) thiol (mercapto),

(29) a thiol (mercapto) group substituted by
1) a $C_{1-6}$ alkyl unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano, 2) a $C_{3-6}$ cycloalkyl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano, 3) a $C_{6-10}$ aryl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano or 4) a $C_{7-12}$ aralkyl group unsubstituted or substituted by 1 to 5 substituents selected from the group consisting of (1) a halogen, (2) an alkoxy group unsubstituted or substituted by 1 to 3 halogen atoms, (3) an alkyl unsubstituted or substituted by 1 to 3 halogen atoms, (4) nitro, (5) amino and (6) cyano,

(30) formyl,

(31) a $C_{1-6}$ alkyl carbonyl group unsubstituted or substituted by 1 to 5 substituents selected from the group consisting of a halogen atom, a lower alkoxy group and a lower alkyl group,

(32) a $C_{1-6}$ sulfinyl group unsubstituted or substituted by 1 to 5 substituents selected from the group consisting of a halogen atom, a lower alkoxy group and a lower alkyl group,

(33) a $C_{1-6}$ sulfonyl group unsubstituted or substituted by 1 to 5 substituents selected from the group consisting of a halogen atom, a lower alkoxy group and a lower alkyl group,

(34) a halogen atom,

(35) nitro,

(36) cyano, and

R is an imidazolyl, a triazolyl or a pyridyl, each of which is unsubstituted or substituted by one to three substituents selected from the group consisting of 1) a $C_{1-4}$ alkoxy group unsubstituted or substituted by 1 to 3 halogen atoms, 2) a halogen atom, 3) a $C_{1-4}$ alkyl group unsubstituted or substituted by 1 to 3 halogen atoms, 4) an aryl group unsubstituted or substituted by a hydroxyl group, an amino group, a nitro group or a cyano group, and 5) nitro group, provided that 3,4-dihydro-6-[3-(1H-imidazol-1-yl)-1-propenyl]-2(1H)-quinolone and 2-[3-[5-ethyl-6-methyl-2-(benzyloxy)-3-pyridyl]-1-propenyl] benzoxazole are excluded, or a salt thereof.

2. A compound as claimed in claim 1, wherein the ring:

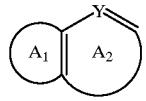

is naphthalen-2-yl, 5,6,7,8-tetrahydronaphthalen-2-yl, quinolin-3-yl, benzofuran-2-yl or benzothiophen-2-yl.

3. A compound as claimed in claim 1, wherein R is imidazolyl which is unsubstituted or substituted by one to three substituents selected from the group consisting of 1) a $C_{1-4}$ alkoxy group unsubstituted or substituted by 1 to 3 halogen atoms, 2) a halogen atom and 3) a $C_{1-4}$ alkyl group unsubstituted or substituted by 1 to 3 halogen atoms.

4. A compound as claimed in claim 1, wherein the ring:

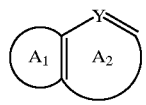

is naphthalene or tetraline.

5. A compound as claimed in claim 1, wherein the ring

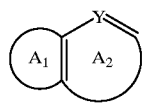

is benzothiophene or benzofuran.

6. A compound as claimed in claim 1, wherein the ring

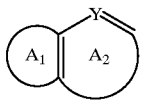

is benzothiophene.

7. A compound as claimed in claim 1, wherein Z is an ethenylene which may be substituted by methyl or fluorine.

8. A compound as claimed in claim 1, wherein Z is unsubstituted ethenylene.

9. A compound as claimed in claim 1, wherein X is unsubstituted methylene.

10. A compound as claimed in claim 1, which is 1-{(E)-3-(2-naphthyl)-2-propenyl}-1H-imidazole or a salt thereof.

11. A compound as claimed in claim 1, which is 1-{(E)-3-(2-naphthyl)-2-butene-1-yl}-1H-imidazole or a salt thereof.

12. A compound as claimed in claim 1, which is 1-{(E)-3-(5-fluoro-3-methylbenzo{b}thiophene-2-yl)-2-propene-1-yl}-1H-imidazole or a salt thereof.

13. A compound as claimed in claim 1, which is 4-{(E)-3-(5-fluoro-3-methylbenzo{b}thiophene-2-yl)-2-propene-1-yl}-1H-imidazole or a salt thereof.

14. A compound as claimed in claim which is 4-{(E)-3-(5-methoxy-3-methylbenzo{b}thiophene-2-yl)-2-propene-1-yl}-1H-imidazole or a salt thereof.

15. A pharmaceutical composition comprising a compound as claimed in claim 1, and a pharmaceutically acceptable carrier, diluent or excipient.

16. A method for treating a mammal suffering from a disease whose exacerbation factor is androgen or estrogen selected from the group consisting of a prostate cancer, prostatic hypertrophy, virilism, hirsutism, male pattern alopecia, precocious puberty, breast cancer, uterine cancer, mastopathy, uterus myoma, and endometriosis, which comprises administering an effective amount of a compound as claimed in claim 1.

17. A method for treating a mammal with breast cancer or prostate cancer comprising administering a tumor inhibiting amount of a compound of claim 1 to a mammal in need thereof.

18. A method for making an antitumor composition for treating a disease whose exacerbation factor is androgen or estrogen selected from the group consisting of a prostate cancer, prostatic hypertrophy, virilism, hirsutism, male pattern alopecia, precocious puberty, breast cancer, uterine cancer, mastopathy, uterus myoma, and endometriosis, comprising formulating the composition with an effective amount of the compound as claimed in claim 1.

19. A process for producing a compound according to claim 1, which comprises reacting a compound of the formula:

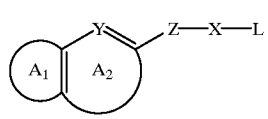

(I)

wherein L is a leaving group, and each of the other symbols has the meanings as defined in claim 1, or a salt thereof with a compound of the formula:

M—R       (III)

wherein M is a hydrogen atom or a metal atom, and R has the meanings as defined in claim 1, or a salt thereof.

* * * * *